US008052966B2

(12) United States Patent
Hall et al.

(10) Patent No.: US 8,052,966 B2
(45) Date of Patent: *Nov. 8, 2011

(54) METHODS AND COMPOSITIONS FOR TREATING METASTATIC CANCER

(75) Inventors: Frederick L. Hall, Glendale, CA (US); Erlinda M. Gordon, Glendale, CA (US)

(73) Assignee: University of Southern California, Los Angeles, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/829,926

(22) Filed: Apr. 21, 2004

(65) Prior Publication Data

US 2004/0253215 A1    Dec. 16, 2004

(51) Int. Cl.
*A01N 63/00* (2006.01)
*A61K 31/70* (2006.01)
*A01K 67/00* (2006.01)

(52) U.S. Cl. ................. 424/93.2; 514/44; 536/23.72

(58) Field of Classification Search .................. None
See application file for complete search history.

(56) References Cited

U.S. PATENT DOCUMENTS

| | | | |
|---|---|---|---|
| 5,328,470 A | 7/1994 | Nabel et al. | |
| 5,354,674 A | 10/1994 | Hodgson | |
| 5,512,421 A | 4/1996 | Burns et al. | |
| 5,591,624 A | 1/1997 | Barber et al. | |
| 5,643,770 A | 7/1997 | Mason et al. | |
| 5,661,023 A | 8/1997 | Hrinda et al. | |
| 5,670,488 A | 9/1997 | Gregory et al. | |
| 5,800,811 A | 9/1998 | Hall et al. | |
| 6,004,798 A | 12/1999 | Anderson et al. | |
| 6,281,010 B1 | 8/2001 | Gao et al. | |
| 6,818,439 B1 * | 11/2004 | Jolly et al. | 435/320.1 |
| 7,060,811 B2 * | 6/2006 | Aldaz et al. | 536/23.5 |
| 7,347,998 B2 * | 3/2008 | Hall et al. | 424/93.2 |
| 7,708,986 B2 * | 5/2010 | Gordon et al. | 424/93.2 |
| 2002/0177571 A1 | 11/2002 | Gordon et al. | |
| 2003/0027818 A1 | 2/2003 | Redmond et al. | |
| 2006/0251627 A1 | 11/2006 | Gordon | |
| 2007/0224188 A1 | 9/2007 | Allan et al. | |
| 2007/0225603 A1 | 9/2007 | Jackson | |
| 2008/0119572 A1 | 5/2008 | Owens et al. | |
| 2009/0123428 A1 | 5/2009 | Hall et al. | |

FOREIGN PATENT DOCUMENTS

| | | |
|---|---|---|
| CA | 2595915 | 8/1998 |
| EP | 0334 301 | 9/1998 |
| WO | WO 95/25789 A1 | 9/1995 |
| WO | WO 96/30504 | 10/1996 |
| WO | WO 96/39430 | 12/1996 |
| WO | WO-98-01582 A1 | 1/1998 |
| WO | WO 98/44938 | 10/1998 |
| WO | WO 98/51700 | 11/1998 |
| WO | 01/64870 | 9/2001 |

OTHER PUBLICATIONS

Dang et al. Gene therapy and translational cancer research. Clin. Cancer Res. 5:471-474,1999.*
Romano et al. Latest developments in gene transfer technology: Achievements, perspectives, and controversies over therapeutic applications. Stem Cells 18:19-39, 2000.*
Verma et al. Gene therapy: Twenty-first century medicine. Annu. Rev. Biochem. 74:711-738, 2005.*
Goncalves M. A concise peer into the background, initial thoughts and practices of human gene therapy. BioEssays 27:506-517, 2005.*
Gardlik et al. Vectors and delivery systems in gene therapy. Med. Sci. Monit. 11:RA110-121, 2005.*
Gordon et al. Inhibition of mestastatic tumor gowth in nude mice by portal vein infusions of matrix-targeted retroviral vectors bearing a cytocidal cyclin G1 cosntruct. Cancer Res. 3343-3347, 2000.*
Lenz et al. Tumor site-specific phase I/II evaluationof the safety and efficacy of hepatic arterial infusion of a matrix-targeted retroviral vector bearing a dominant negtive cyclin G1 (dnG1) construct as treatment for colorectal carcinoma metastatic to liver. Human Gene Therapy 12:1563-1565, Aug. 2001.*
Anderson W.F., "Human Gene Therapy," *Nature*, vol. 392 (supp), pp. 25-30, 1998.
Arap et al., "Cancer Treatment By Targeted Drug Delivery To Tumor Vasculature In A Mouse Model", *Science*, vol. 279, pp. 377-380, 1998.
Asher, et al., "Murine Tumor Cells Transduced with the Gene for Tumor Necrosis Factor-α", *The Journal of Immunology*, vol. 146, No. 9, pp. 3227-3234, May 1, 1991.
Blankenstein, et al., "Tumor Suppression after Tumor Cell-targeted Tumor Necrosis Factor α Gene Transfer", *The Journal of Experimental Medicine*, vol. 173, No. 5, pp. 1047-1052, May 1991.
Borrello, et al., "A Universal Granulocyte-Macrophage Colony-Stimulating Factor-Producing Bystander Cell Line for Use in the Formulation of Autologous Tumor Cell-Based Vaccines", *Human Gene Therapy*, vol. 10, No. 12, pp. 1983-1991, Aug. 10, 1999.
Cosset et al., "Retroviral Targeting by Envelopes Expressing an N-Terminal binding domain", *J Virol*, vol. 69, pp. 6314-6322, 1995.
Cosset et al., "Targeting Retrovirus Entry", *Gene Therapy*, vol. 3, pp. 946-956, 1996.
Coze, et al., "Characteristics and Immunomodulatory Properties of Human Neuroblastoma Cells after Retrovirus-Mediated Gene Transfer of the Cytokine Genes IL-2 and IFN-γ", *Transgenics*, vol. 1, No. 6, pp. 585-595, 1995.
Dranoff, et al., "Vaccination with irradiated tumor cells engineered to secrete murine granulocyte-macrophage colony-stimulating factor stimulates potent, specific, and long-lasting anti-tumor immunity", *Proceedings of the National Academy of Sciences*, vol. 90, No. 8, pp. 3539-3543, Apr. 15, 1993.
El Kamar et al., "Metastatic Pancreatic Cancer: Emerging Strategies in Chemotherapy and Palliative Care", *The Oncologist*, vol. 8, pp. 18-34, 2003.

(Continued)

Primary Examiner — Quang Nguyen
(74) Attorney, Agent, or Firm — Wilson Sonsini Goodrich & Rosati

(57) ABSTRACT

Methods and compositions for producing targeted delivery vectors are provided. Such vectors are useful for treating neoplastic disorders. Also provided are protocols for administering targeted delivery vectors in a clinical setting such that a therapeutic effect is achieved.

11 Claims, 25 Drawing Sheets

OTHER PUBLICATIONS

Fearon, et al., "Interleukin-2 Production by Tumor Cells Bypasses T Helper Function in the Generation of an Antitumor Response", *Cell*, vol. 60, No. 3, pp. 397-403, Feb. 9, 1990.

Fong, et al., "The Use and Development of Retroviral Vectors to Deliver Cytokine Genes for Cancer Therapy", *Critical Reviews in Therapeutic Drug Carrier Systems*, vol. 17, No. 1, pp. 1-60, 2000.

Foreman, et al., "Mechanisms of selective killing of neuroblastoma cells by natural killer cells and lymphokine activated killer cells. Potential for residual disease eradication", *British Journal of Cancer*, vol. 67, pp. 933-938, 1993.

Gansbacher, et al., "Retroviral lymphokine gene transfer induced secretion of Interleukin-2 (IL-2) or Interferon-gamma (IFN-γ) by human melanoma cells", Eighty-Second annual meeting of the American Association for Cancer Research Proceedings, Houston, Texas, vol. 32, 1514 (Abstract) May 15-18, 1991.

Gilboa, "Immunotherapy of Cancer with Genetically Modified Tumor Vaccines", Seminars in Oncology, vol. 23, No. 1, pp. 101-107, Feb. 1996.

Golumbek, "Treatment of Established Renal Cancer by Tumor Cells Engineered to Secrete Interleukin-4", *Science*, vol. 254, pp. 713-716, Nov. 1, 1991.

Gordon, et al., "Inhibition of Metastatic Tumor Growth in Nude Mice by Portal Vein Infusions of Matrix-targeted Retroviral Vectors Bearing a Cytocidal Cyclin G1 Construct", *Cancer Research*, vol. 60, No. 13, pp. 3343-3347, Jul. 1, 2000.

Gordon, E.M. et al., "Capture and expansion of bone marrow-derived mesenchymal progenitor cells with a transforming growth factor-β1—von Willebrand's factor fusion protein for retrovirus-mediated delivery of coagulation factor IX", Jul. 20, 1997, *Human Gene Therapy*, vol. 8, pp. 1385-1394.

Gordon, et al., "Systemic Administration of a Matrix-Targeted Retroviral Vector is Efficacious for Cancer Gene Therapy in Mice", *Human Gene Therapy*, vol. 12, No. 2, pp. 193-204, Jan. 20, 2001.

Gordon et al., "Genetic Engineering of Targeted Retroviral Vectors", Curiel DT, Douglass JT, eds. Vector Targeting Strategies for Therapeutic Gene Delivery, New York, NY Wiley-Liss, Inc., pp. 293-320, 2002.

Guinan, et al., "Pivotal Role of the B7:CD28 Pathway in Transplantation Tolerance and Tumor Immunity", *Blood*, vol. 84, No. 10., pp. 3261-3282, Nov. 15, 1994.

Hall et al., "Targeting Retroviral Vectors to Vascular Lesions by Genetic Engineering of the MoMuIV gp70 Envelope Protein", Human Gene Therapy 8, pp. 2183-2192, 1997.

Hall, et al., "Molecular Engineering of Matrix-Targeted Retroviral Vectors Incorporating a Surveillance Function Inherent in von Willebrand Factor", *Human Gene Therapy*, vol. 11. No. 7, pp. 983-993, May 1, 2000.

Handgretinger et al., "Interferon-Gamma Upregulates the Susceptibility of Human Neuroblastoma Cells to Interleukin-2-Activated Natural Killer Cells", *Natural Immunity and Cell Growth Regulation*, vol. 8, pp. 189-196, Jul./Aug. 1989.

Hock, et al., "Interleukin 7 Induces CD4+ T Cell-dependent Tumor Rejection", *The Journal of Experimental Medicine*, vol. 174, No. 6, pp. 1291-1298, Dec. 1, 1991.

Hu et al., "Design of Retroviral Vectors and Helper Cells for Gene Therapy", *Pharmacology Reviews*, vol. 52, No. 4, pp. 493-511, 2000.

Jaffee, "Immunotherapy of Cancer", Annals of the New York Academy of Sciences, vol. 886, pp.67-72.

Kasahara et al., "Tissue-Specific Targeting of Retroviral Vectors Through Ligand-Receptor interactions" *Science*, vol. 266, pp. 1373-1376, Nov. 1994.

Kay et al., "Evidence for gene transfer and expression of factor IX in Hemophillia B Patients", *Nature Genetics*, vol. 24, pp. 257-261, 2000.

Klagsbrun et al., Annual Review of Physiology, vol. 53, pp. 217-239, 1991.

Kim, et al., "Macrophage Colony-Stimulating Factor Can Modulate Immune Responses and Attract Dendritic Cells in Vivo", *Human Gene Therapy*, vol. 11, No. 2, pp. 305-321, Jan. 20, 2000.

Knobloch, et al., "T cell receptor diversity in severe combined immunodeficiency following HLA-haploidentical bone marrow transplantation", *Bone Marrow Transplantation*, vol. 8, No. 5, pp. 383-387, Nov. 1991.

Kotani et al., "Improved Methods of Retroviral Vector Transduction and production for Gene Therapy", *Human Gene Therapy* vol. 5, pp. 19-28, 1994.

Kurane, et al., "Cytokines as an Adjuvant to Tumor Vaccines: Efficacy of Local Methods of Delivery", *Annals of Surgical Oncology*, vol. 4, No. 7, pp. 579-585, 1997.

Kuvshinoff et al., "Treatment of Respectable and Locally Advanced Pancreatic Cancer", *Cancer Control*, vol. 7, pp. 428-436, 2000.

Lenz et al., "Tumor Site-Specific Phase I Evaluation of Safety of Hepatic Arterial Infusion of a matrix-Targeted Retroviral Vector Bearing a Dominant Negative Cyclin G1 Construct as Intervention for Colorectal Carcinoma Metastatic to the Liver", *Human Gene Therapy*, vol. 13, pp. 1515-1537, 2002.

Lieberman et al., "Innovative Treatments for Pancreatic Cancer", *Surg Clin North Am*, vol. 81, pp. 715-739, 2001.

Liu, et al., "Incorporation of Tumor Vasculature Targeting Motifs into Moloney Murine Leukemia Virus Env Escort Proteins Enhances Retrovirus Binding and Transduction of Human Endothelial Cells", *Journal of Virology*, vol. 74, No. 11, pp. 5320-5328, 2000.

Mackensen, et al., "Immunostimulatory Cytokines in Somatic Cells and Gene Therapy of Cancer", *Cytokine and Growth Factor Reviews*, vol. 8, No. 2, pp. 119-128, Jun. 1997.

Magovern et al., "Regional Angiogenesis Induced in Nonischemic Tissue by an Adenoviral Vector Expressing Vascular Endothelial Growth Factor," *Human Gene Therapy*, vol. 8:215-227 (Jan. 20, 1997).

Main, et al., "Human Neuroblastoma Cell Lines are Susceptible to Lysis by Natural Killer Cells But Not by Cytotoxic T Lymphocytes", *The Journal of Immunology*, vol. 135, No. 1, pp. 242-246, Jul. 1985.

Marin et al., "Targeted Infection of Human Cells Via Major Histocompatibility Complex Class 1 Molecules by Moloney Murine Leukemia Virus-Derived Viruses Displaying Single-Chain Antibody Fragment-Envelope Fusion Proteins", *Journal of Virology*, vol. 70, pp. 2957-2962, 1996.

Martin et al., "Retroviral Vector Targeting to Melanoma Cells by Single-Chain Antibody Incorporation in Envelope", *Human Gene Therapy*, vol. 9, 737-746, 1998.

Masood et al., "Retroviral Vectors Bearing IgG-binding Motifs for Antibody-Mediated Targeting of Vascular Endothelial Growth Factor Receptors", *Int'l J Mol Med*, vol. 8, pp. 335-343, 2001.

Mellstedt, et al., "Augmentation of the Immune response with granulocyte-macrophage colony-stimulating factor and other hematopoietic growth factors", *Current Opinion in Hematology*, vol. 6, pp. 169-175, 1999.

Mendiratta, et al., "Combination of Interleukin 12 and interferon α Gene therapy Induces a Synergistic Antitumor Response against Colon and Renal Cell Carcinoma", *Human Gene Therapy*, vol. 11, No. 13, pp. 1851-1862, Sep. 1, 2000.

Miller et al., "Improved Retroviral Vectors For Gene Transfer and Expression", *Biotechniques*,vol. 7, pp. 984-990, 1989.

Miller, et al., "Intratumoral Administration of Adenoviral Interleukin 7 Gene-Modified Dendritic Cells Augments Specific Antitumor Immunity and Achieves Tumor Eradication", *Human Gene Therapy*, vol. 11, No. 1, pp. 53-65, Jan. 1, 2000.

Morgan, et al., "Analysis of the Functional and Host Range-Determining Regions of the Murine Ecotropic and Amphotropic Retrovirus Envelope Proteins", *Journal of Virology*, vol. 67, No. 8, pp. 4712-4721, Aug. 1993.

Nabel, et al., "Direct gene transfer with DNA-liposome complexes in melanoma: Expression, biologic activity, and lack of toxicitiy in humans", *Proceedings of the National Academy of Sciences*, vol. 90, No. 23, pp. 11307-11311, Dec. 1, 1993.

Nagai, et al., "Irradiated tumor cells adenovirally engineered to secrete granculocyte/macrophage-colony-stimulating factor establish antitumor immunity and eliminate pre-existing tumors in syngeneic mice", *Cancer Immunology Immunotherapy*, vol. 47, pp. 72-80, 1998.

Neda et al. "Chemical Modification of an Ecotropic Murine Leukemia Virus Results in Redirection of Its Target Cell Specificity", *The Journal of Biological Chemistry*, vol. 266, No. 22, pp. 14143-14146, Aug. 5, 1991.

Nishi, N. et al., "Collagen-binding growth factors: Production and characterization of functional domain fusion proteins having a collagen-binding domain", Jun. 1998, *Proc. Natl. Acad. Sci. USA*, vol. 95, pp. 7018-7023.

O'Reilly et al., "Endostatin: An Endogenous Inhibitor of Angiogenesis and Tumor Growth", *Cell*, vol. 88, pp. 277-285, 1997.

Ohno et al., "Cell-Specific Targeting of Sindbis Virus Vectors Displaying IgG-binding domains of Protein", *A. Nat Biotechnol.*, vol. 15, pp. 763-767, 1997.

Peng, et al., "Viral Vector Targeting", *Curr Opin Biotechnol*, pp. 454-457, 1999.

Rosenberg et al., "Gene Transfer into Human-Immunotherapy of Patients With Advanced Melanoma, Using Tumor Infiltrating Lymphocytes Modified by Retroviral Gene Transduction", New England Journal of Medicine, 323, pp. 570-578, 1990.

Rosenberg, S.A., "Immunization of Cancer Patients Using Autologous Cancer Cells Modified by Insertion of the Gene for InterLeukin2", *Human Gene Therapy*, vol. 3, No. 1, pp. 75-90, Feb. 1992.

Rosemurgy et al., "New Directions in Systemic Therapy of Pancreatic Cancer", *Cancer Control*, vol. 7, pp. 437-444, 2000.

Russell, S.J. "Retroviral Vectors Displaying Functional Antibody Fragments", 21, *Nucl Acid Res*, vol. 21, p. 1081-1085, 1993.

Sadler, J.E. et al., "Cloning and characterization of two cDNAs coding for human von Willebrand factor", Oct. 1985, *Natl. Acad. Sci. USA*, vol. 82, pp. 6394-6398.

Skotzko, et al., "Retroviral Vector-mediated Gene Transfer of Antisense Cyclin G1 (CYCG1) Inhibits Proliferation of Human Osteogenic Sarcoma Cells", *Cancer Research*, vol. 55, No. 23, pp. 5493-5498, Dec. 1, 1995.

Somia et al., "Generation of Targeted Retroviral Vectors by Using Single-Chain Variable Fragment: An Approach to In Vivo Gene Delivery", *Proc Natl Acad Sci USA* vol. 92, pp. 7570-7574, 1995.

Soneoka, et al., "A transient three-plasmid expression system for the production of high titer retroviral vectors", *Nucleic Acids Research*, vol. 23, No. 4, pp. 628-633, Feb. 25, 1995.

Stromblad et al., "Cell Adhesion and Angiogenesis", *Trends Cell, Biol.*, vol. 64, pp. 462-467, 1996.

Suh, et al., "Treatment of Liver Metastases from Colon Carcinoma with Autologous Tumor Vaccine Expressing Granulocyte-Macrophage Colony-stimulating Factor", *Journal of Surgical Oncology*, vol. 72, No. 4, pp. 218-224, Dec. 1999.

Takagi et al., "A Collagen/Gelatin-Binding DecapeptideDerived from Bovine Propolypeptide of von Willebrand Factor" *Biochemistry*, vol. 31, pp. 8530-8534, 1992.

Takagi et al., "Collagen-Binding Domain Within Bovine Propolypeptide of Von Willebrand Factor", J. Biol Chem, vol. 266, pp. 5575-5579, 1991.

Tepper, et al., "Experimental and Clinical Studies of Cytokine Gene-Modified Tumor Cells", *Human Gene Therapy*, vol. 5, No. 2, pp. 153-164, Feb. 1994.

Tseng et al., "Gene Therapy for Pancreatic Cancer", *Surg Oncol Clin N. Am*, vol. 11, pp. 537-569, 2002.

Ucar, et al., "Sustained cytokine production and immunophenotypic changes in human neuroblastoma cell lines transduced with a human gamma interferon vector", *Cancer Gene Therapy*, vol. 2, No. 3, pp. 171-181, 1995.

Valsesia-Wittman et al., "Modification in the Binding Domain of Avian Retrovirus Envelope Protein to Redirect the Host Range of Retroviral Vectors", *Journal of Virology*, vol. 68, pp. 4609-4619, 1994.

Van Riel et al., "Pancreaticobiliary Cancer: The Future Aspects of Medical Oncology", Ann Oncol, vol. 10, Suppl 4, pp. 296-299, 1999.

Verma et al., "Gene Therapy: Promises, Problems and Prospects", *Nature*, vol. 389, pp. 239-242, 1997.

Warren, et al., "Uses of granulocyte-macrophage colony-stimulating factor in vaccine development", *Current Opinion in Hematology*, vol. 7, pp. 168-173, 2000.

Watanabe, et al., "Exogenous expression of mouse interferon γ cDNA in mouse neuroblastome C1300 cells results in reduced tumorigenicity by augmented anti-tumor immunity", *Proceedings of the National Academy of Sciences*, vol. 86, No. 23, pp. 9456-9459, Dec. 1989.

Wu et al., "Characterization of the Proline-Rich Region of Murine Leukemia Virus Envelope Protein", *Journal of Virology*, vol. 72, pp. 5383-5391, 1998.

Wu et al., "Molecular Cloning of the Human CYCG1 Gene Encoding a G-Type Cyclin: Overexpression in Human Osteosarcoma Cells", *Oncology Reports*, vol. 1, pp. 705-711, 1994.

Xie et al., "Elements within the First 17 Amino Acids of Human Osteonectin Are Responsible for Binding to Type V Collagen", *The Journal of Biological Chemistry*, vol. 271, No. 14, pp. 8121-8125, Apr. 5, 1996.

Xu et al., "Long Term Inhibition of Neointima Formation in Balloon-Injured Rat Arteriesby Intraluminal Instillation of a Matrix-Targeted Retroviral Vector Bearing an Improved Cytocidal Cyclin G1 Construct", *Intl J Mol Med*, vol. 8, pp. 19-30, 2001.

Yang et al., "Development of Novel Cell Surface CD34-Targeted Recombinant Adenoassociated Virus Vector for Gene Therapy", *Human Gene Therapy*, vol. 9, pp. 1929-1937, 1998.

Yang et al., "Generation of Retroviral Vector for Clinical Studies using Transient Transfection", *Human Gene Therapy*, vol. 10, pp. 123-132, 1999.

Zhao et al., "Identification of the Block in Targeted Retroviral-Mediated Gene Transfer", *Proc National Academy of Science USA*, vol. 96, pp. 4005-4010, 1999.

Zwiebel, J.A., "Cancer Gene and Oncolytic Virus Therapy", *Semin Oncol*, vol. 28, pp. 336-343, 2001.

Behrens, et al. Retroviral gene therapy vectors for prevention of excimer laser-induced corneal haze. Invest Ophthalmol Vis Sci. 2002;43(4):968-77.

Gordon, et al. First clinical experience using a 'pathotropic' injectable retroviral vector (Rexin-G) as intervention for stage IV pancreatic cancer. Int J Oncol. 2004; 24(1):177-85.

Gordon, et al. Le morte du tumour: histological features of tumor destruction in chemo-resistant cancers following intravenous infusions of pathotropic nanoparticles bearing therapeutic genes. Int J Oncol. 2007; 30(6):1297-307.

Gordon, et al. Lesion-targeted injectable vectors for vascular restenosis. Hum Gene Ther. 2001; 12(10):1277-87.

Gordon, et al. Pathotropic nanoparticles for cancer gene therapy Rexin-G IV: three-year clinical experience. Int J Oncol. 2006; 29(5):1053-64.

Song, et al. Phase I/II evaluation of safety and efficacy of a matrix-targeted retroviral vector bearing a dominant negative cyclin G1 construct (Md-dnG1) as adjunctive intervention for superficial corneal opacity/corneal scarring. Hum Gene Ther. 2003; 14(3):306-9.

Office Action dated Apr. 7, 2009 issued in U.S. Appl. No. 12/016,847.

James, et al. Measuring response in solid tumors: unidimensional versus bidimensional measurement. J Natl Cancer Inst. Mar. 17, 1999;91(6):523-528.

Langreth, et al. Researchers get dose of reality as logistics stymie gene therapy. The Wall Street Journal. Oct. 27, 1999 (5 pages).

Blackwell, et al. Retargeting to EGFR enhances adenovirus infection efficiency of squamous cell carcinoma. Arch Otolaryngol Head Neck Surg. Aug. 1999;125(8):856-63.

Chu, et al. Toward highly efficient cell-type-specific gene transfer with retroviral vectors displaying single-chain antibodies. J Virol. Jan. 1997;71(1):720-5.

Drapkin, et al. Targeting the urokinase plasminogen activator receptor enhances gene transfer to human airway epithelia. J Clin Invest. Mar. 2000;105(5):589-96.

Goldman, et al. Targeted gene delivery to Kaposi's sarcoma cells via the fibroblast growth factor receptor. Cancer Res. Apr. 15, 1997;57(8):1447-51.

Han, et al. Ligand-directed retroviral targeting of human breast cancer cells. Proc Natl Acad Sci U S A. Oct. 10, 1995;92(21):9747-51.

Kasono, et al. Selective gene delivery to head and neck cancer cells via an integrin targeted adenoviral vector. Clin Cancer Res. Sep. 1999;5(9):2571-9.

McDonald, et al. Efficient adenoviral gene transfer to kidney cortical vasculature utilizing a fiber modified vector. J Gene Med. Mar.-Apr. 1999;1(2):103-10. (Abstract only).

Nicklin, et al. Selective targeting of gene transfer to vascular endothelial cells by use of peptides isolated by phage display. Circulation. Jul. 11, 2000;102(2):231-7.

Ohno, et al. Retrovirus vectors displaying the IgG-binding domain of protein A. Biochem Mol Med. Oct. 1997;62(1):123-7.

Printz, et al. Fibroblast growth factor 2-retargeted adenoviral vectors exhibit a modified biolocalization pattern and display reduced toxicity relative to native adenoviral vectors. Hum Gene Ther. Jan. 1, 2000;11(1):191-204. (Abstract only).

Rancourt, et al. Basic fibroblast growth factor enhancement of adenovirus-mediated delivery of the herpes simplex virus thymidine kinase gene results in augmented therapeutic benefit in a murine model of ovarian cancer. Clin Cancer Res. Oct. 1998;4(10):2455-61.

Reynolds, et al. A targetable, injectable adenoviral vector for selective gene delivery to pulmonary endothelium in vivo. Mol Ther. Dec. 2000;2(6):562-78.

Romanczuk, et al. Modification of an adenoviral vector with biologically selected peptides: a novel strategy for gene delivery to cells of choice. Hum Gene Ther. Nov. 1, 1999;10(16):2615-26. (Abstract only).

Therasse, et al. New guidelines to evaluate the response to treatment in solid tumors. J Natl Cancer Inst. Feb. 2, 2000;92(3):205-16.

Van Beusechem, et al. Efficient and selective gene transfer into primary human brain tumors by using single-chain antibody-targeted adenoviral vectors with native tropism abolished. J Virol. Mar. 2002;76(6):2753-62.

Vanderkwaak, et al. An advanced generation of adenoviral vectors selectively enhances gene transfer for ovarian cancer gene therapy approaches. Gynecol Oncol. Aug. 1999;74(2):227-34. (Abstract only).

Wickham, et al. Targeting endothelium for gene therapy via receptors up-regulated during angiogenesis and inflammation. Cancer Immunol Immunother. Nov.-Dec. 1997;45(3-4):149-51. (Abstract only).

Pan and Whitley, "Closed hollow-fiber bioreactor: a new approach to retroviral vector production," J. Gene Med. 1(6):433-440 (1999).

Reeves and Cornetta, "Clinical retroviral vector production: step filtration using clinically approved filters improves titers," Gene Therapy 7:1993-1998 (2000).

Baum et al., "Side effects of retroviral gene transfer into hematopoietic stem cells," Blood 101:2099-2114 (2003).

Hacien-Bey-Abina et al., "LMO2-Associated Clonal T Cell Proliferation in Two Patients after Gene Therapy for SCID-X1," Science 302:415-419 (2003).

Kustikova et al., "Dose finding with retroviral vectors: correlation of retroviral vector copy numbers in single cells with gene transfer efficiency in a cell population," Blood 102:3934-3937 (2003).

Diehl et al., "A Dominant-Negative Cyclin D1 Mutant Prevents Nuclear Import of Cyclin-Dependent Kinase 4 (CDK4) and Its Phosphorylation by CDK-Activating Kinase," Mol. Cell Biol. 17(12):7362-7374 (1997).

Geddis et al., "Thrombopoietin: a pan-hematopoietic cytokine," Cytokine & Growth Factor Reviews 13:61-67 (2002).

Ghezzi et al., "Erythropoietin as an antiapoptotic, tissue-protective cytokine," Cell Death & Differentiation 11:537-544 (2004).

Hinds et al., "Function of a human cyclin gene as an oncogene," PNAS USA 91:709-713 (1994).

Addison et al., "Comparison of the human versus murine cytomegalovirus immediate early gene promoters for transgene expression by adenoviral vectors," J. Gen. Virol. 78:1653-1661 (1997).

Chen et al., "Combination suicide and cytokine gene therapy for hepatic metastases of colon carcinoma: Sustained antitumor immunity prolongs animal survival," Cancer Res. 46:3758-3762 (1996).

Kafri et al., "Sustained expression of genes delivered directly into liver and muscle by lentiviral vectors," Nature Genetics 17:314-317 (1997).

Rousculp et al., "Quantitative evaluation of retroviral gene transduction efficiency in human lung cancer cells," Human Gene Therapy 3:471-477 (1992).

Arnold et al., "Molecular Pathogenesis of Colorectal Cancer," Cancer 104:2035-2047 (2005).

Check, E., "A tragic setback," Nature 420:116-118 (2002).

Galanis et al., "Phase I Trial of a Pathotropic Retroviral Vector Expressing a Cytocidal Cyclin G1 Construct (Rexin-G) in Patients With Advanced Pancreatic Cancer," Mol Ther 16(5):979-984 (2008).

Hacein-Bey-Abina et al., "A Serious Adverse Event after Successful Gene Therapy for X-Linked Severe Combined Immunodeficiency," N Engl J Med 348(3):255 (2003).

Huang et al., "The structural and mechanical complexity of cell-growth control," Nature Cell Biol 1:E131-E138 (1999).

Liberman et al., "Breast cancer diagnosis by scintimammography: a meta-analysis and review of the literature," Breast Cancer Research and Treatment 80:115-126 (2003).

Lowenfels et al., "Epidemiology and Prevention of Pancreatic Cancer," Jpn J Clin Oncol 34(5):238-244 (2004).

Nagano et al., "Gene therapy eradicating distant disseminated micro-metastases by optimal cytokine expression in the primary lesion only: novel concepts for successful cytokine gene therapy," Intl J Onc 24:549-558 (2004).

Pollack, A., "F.D.A. Halts 27 Gene Therapy Trials After Illness," The New York Times, Jan. 15, 2003 http://query.nytimes.com/gst/fullpage.html?res=990DE6DD1031F936A25752C)A9659C printed out on Oct. 25, 2010.

Shidong, et al. "Dosimetric and Technical Considerations for Interstitial Adenoviral Gene Therapy as Applied to Prostate Cancer" Int. Journal Radiation Oncology Biol. Phys. 55(1):204-214 (2003).

\* cited by examiner

Figure 1
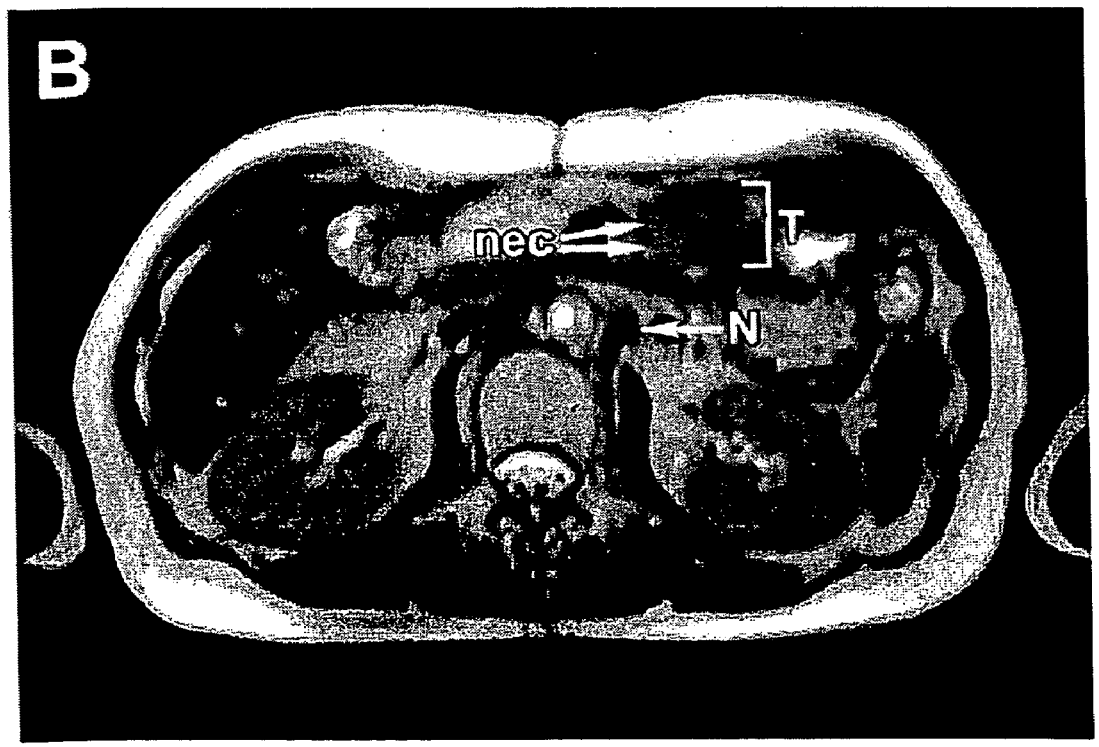

Figure 2
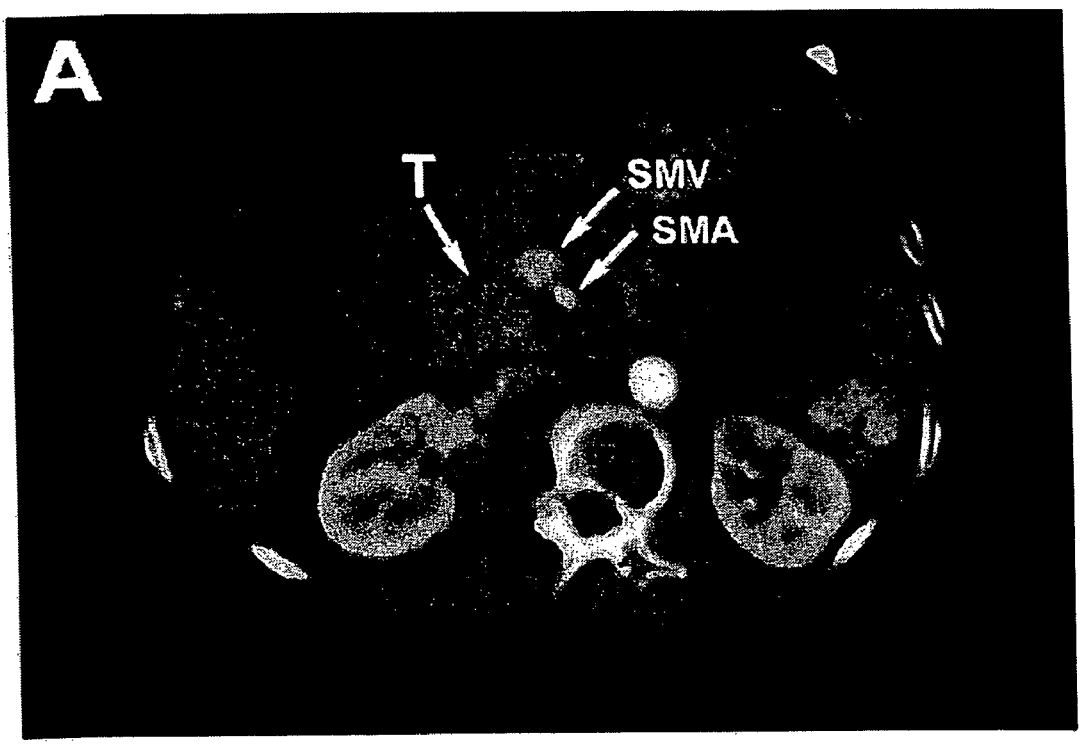
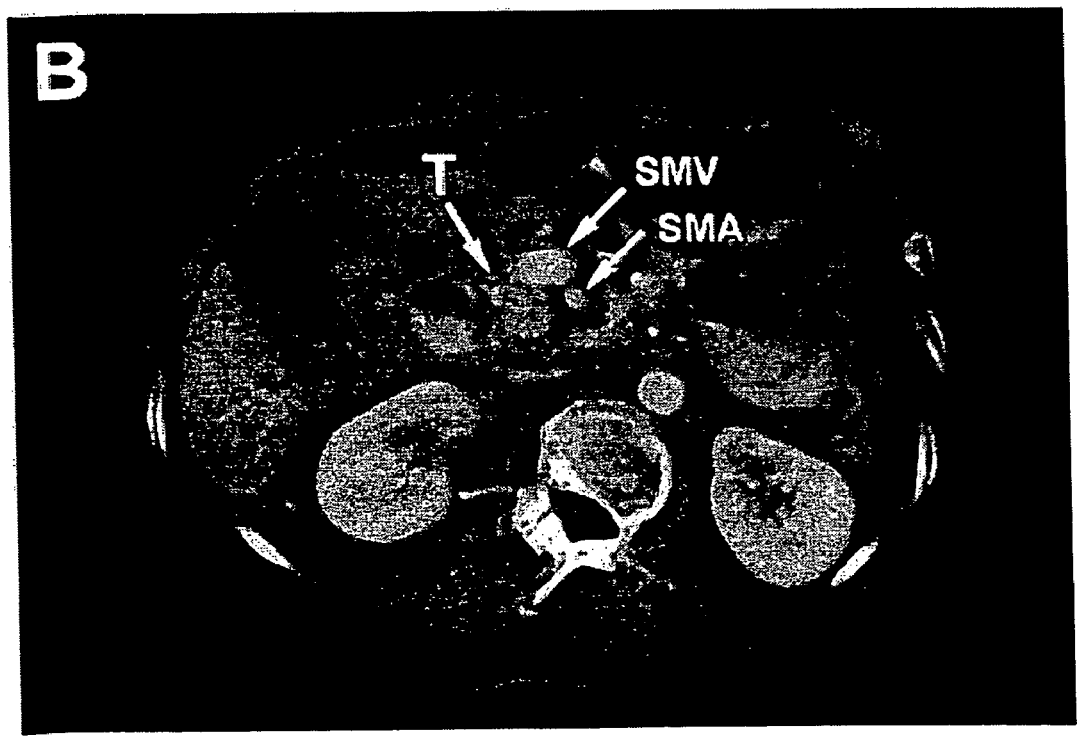

Figure 18

```
     SspI MscI                                             SspI    BsrDI
      |    |                                                |     MscI
      |    |                                                |      |
TCAATATTGGCCATTAGCCATATTATTCATTGGTTATATAGCATAAATCAATATTGGCTATTGGCCATTG
AGTTATAACCGGTAATCGGTATAATAAGTAACCAATATATCGTATTTAGTTATAACCGATAACCGGTAAC
      10        20        30        40        50        60        70

BsrGI                              Bgl I
                                |                                  |
CATACGTTGTATCTATATCATAATATGTACATTTATATTGGCTCATGTCCAATATGACCGCCATGTTGGC
GTATGCAACATAGATATAGTATTATACATGTAAATATAACCGAGTACAGGTTATACTGGCGGTACAACCG
      80        90       100       110       120       130       140

SpeI    AseI
        |       |
ATTGATTATTGACTAGTTATTAATAGTAATCAATTACGGGTCATTAGTTCATAGCCCATATATGGAGTT
TAACTAATAACTGATCAATAATTATCATTAGTTAATGCCCCAGTAATCAAGTATCGGGTATATACCTCAA
     150       160       170       180       190       200       210

Bgl I                       AatII
                                       |                           |
CCGCGTTACATAACTTACGGTAAATGGCCCGCCTGGCTGACCGCCCAACGACCCCCGCCCATTGACGTCA
GGCGCAATGTATTGAATGCCATTTACCGGGCGGACCGACTGGCGGGTTGCTGGGGGCGGGTAACTGCAGT
     220       230       240       250       260       270       280

AatII
                                                |
ATAATGACGTATGTTCCCATAGTAACGCCAATAGGGACTTTCCATTGACGTCAATGGGTGGAGTATTTAC
TATTACTGCATACAAGGGTATCATTGCGGTTATCCCTGAAAGGTAACTGCAGTTACCCACCTCATAAATG
     290       300       310       320       330       340       350

Bgl I               NdeI                              AatII
          |                   |                                 |
GGTAAACTGCCCACTTGGCAGTACATCAAGTGTATCATATGCCAAGTCCGCCCCCTATTGACGTCAATGA
CCATTTGACGGGTGAACCGTCATGTAGTTCACATAGTATACGGTTCAGGCGGGGGATAACTGCAGTTACT
     360       370       380       390       400       410       420

Bgl I
          |
CGGTAAATGGCCCGCCTGGCATTATGCCCAGTACATGACCTTACGGGACTTTCCTACTTGGCAGTACATC
GCCATTTACCGGGCGGACCGTAATACGGGTCATGTACTGGAATGCCCTGAAAGGATGAACCGTCATGTAG
     430       440       450       460       470       480       490

SnaBI            NcoI
    |                |
TACGTATTAGTCATCGCTATTACCATGGTGATGCGGTTTTGGCAGTACACCAATGGGCGTGGATAGCGGT
ATGCATAATCAGTAGCGATAATGGTACCACTACGCCAAAACCGTCATGTGGTTACCCGCACCTATCGCCA
     500       510       520       530       540       550       560

AatII
                                |
TTGACTCACGGGGATTTCCAAGTCTCCACCCCATTGACGTCAATGGGAGTTTGTTTTGGCACCAAAATCA
AACTGAGTGCCCCTAAAGGTTCAGAGGTGGGGTAACTGCAGTTACCCTCAAACAAAACCGTGGTTTTAGT
     570       580       590       600       610       620       630

SgfI
                           PvuI
                             |
ACGGGACTTTCCAAAATGTCGTAACAACTGCGATCGCCCGCCCCGTTGACGCAAATGGGCGGTAGGCGTG
TGCCCTGAAAGGTTTTACAGCATTGTTGACGCTAGCGGGCGGGGCAACTGCGTTTACCCGCCATCCGCAC
     640       650       660       670       680       690       700

SacI
                      Ecl136 II                       HindIII
                       | |                               |
TACGGTGGGAGGTCTATATAAGCAGAGCTCGTTTAGTGAACCGTCAGATCACTAGAAGCTTTATTGCGGT
ATGCCACCCTCCAGATATATTCGTCTCGAGCAAATCACTTGGCAGTCTAGTGATCTTCGAAATAACGCCA
     710       720       730       740       750       760       770
```

Figure 19B

| No. | Stedim P/N | Description | Material | Qty Ea. |
|---|---|---|---|---|
| | | Units of Measure: Components = each/ Tubing = feet | | |
| 1 | 100029 | Coupling Body, Female, 3/8" | POLYCARBNT | 2 |
| 2 | 100044 | Hose Barb, 3/8" to 3/8" | POLYCARBNT | 3 |
| 3 | 100045 | Hose Barb, Reducing, 1/4" 3/8" | POLYCARBNT | 1 |
| 4 | 100048 | Connector, Y, 3/8" 3/8" 3/8" | POLYCARBNT | 1 |
| 5 | 100061 | Additive Port (Latex Free) (TD | ABS/SP/PP | 2 |
| 6 | 100066 | Plug, Tubing, Clear 1/2x1/2 | ACRYLIC | 1 |
| 7 | 100090 | Pinch Clamp for 3/8 & 1/2 Tub. | POLYESTER | 5 |
| 8 | 100128 | Spike Port/ EVA | EVA | 60 |
| 9 | 100138 | Connector, 5-Way(TD00-261) | | 10 |
| 10 | 100143 | Plug, MPC, Male | POLYCARBNT | 2 |
| 11 | 100144 | Plug, Tubing, 5/32" | POLYPROPYL | 60 |
| 12 | 100162 | Connector, T, (3/16") | POLYPROPYL | 8 |
| 13 | 100164 | Connector, Y, (1/4") | POLYPROPYL | 1 |
| 14 | 100173 | Hose Barb, (5/32" to 1/4") | POLYPROPYL | 60 |
| 15 | 100216 | Connector, T, 3/8x 3/8x 3/8 | PVC/NORTON | 1 |
| 16 | 100321 | Hose Barb, 3/8" to 1/8" | POLYCARBNT | 2 |
| 17 | 100332 | Cable Tie, 7" I.D. (w/ Rat su | NYLON | 60 |
| 18 | 100347 | Cable Tie, Black,5.6" x .14" | NYLON 12 | 225 |
| 19 | 200002 | Tubing, 3/8" IDx3/32" Wall | SILICONE | 2 |
| 20 | 200004 | Tubing, Thick Wall, 3/8 x 1/8" | SILICONE | 11 |
| 21 | 200006 | Tubing, 3/16" ID x 1/16" WALL | SILICONE | 5 |
| 22 | 200039 | Tubing, 1/4" ID x 1/8" Wall | SILICONE | 4 |
| 23 | 200048 | Tubing,Tyg,Mod Gr 1/8"IDx1/16W | PVC | 0.5 |
| 24 | 200053 | Tubing,Tygon,Med Gr 5/32x1/32W | PVC | 30 |
| 25 | 200054 | Tubing,Tygon,Med Gr 5/32x1/16W | PVC | 10 |
| 26 | 400261 | Flexboy, 10L, 3 Bare Ports, NS | STEDIM 71 | 1 |
| 27 | 400263 | Flexboy, 50L, 3 Bare Ports, NS | STEDIM 71 | 1 |
| 28 | 400503 | Bag, FLEXBOY, 500ml, 3 Bare Po | STEDIM71 | 60 |
| 29 | 500004 | Bag, Poly 8"x 10" | PLASTIC | A/R |
| 30 | 500007 | Bag, Poly 3" x 5" | PLASTIC | A/R |
| 31 | 500009 | Adhesive, Loctite, 4011 | CYANOACRYL | A/R |
| 32 | 500010 | Primer, Loctite, 7701 | N-HEPTANE | A/R |
| 33 | 500016 | Radiation Indicator, W/ Print | PAPER | A/R |
| 34 | 800003 | Bag, Poly, (42" x 26" x 63") | POLY | 0.2 |
| 35 | 800005 | Bag, Poly, 24" x 36" (6 mil) | POLY | 1 |
| 36 | 800009 | Carton, Packing, MEDIUM | CARDBOARD | 0.2 |
| 37 | 800012 | Cable Tie, Beaded, 8" | NYLON | A/R |

SEQUENCE LISTING

```
<160> NUMBER OF SEQ ID NOS: 7

<210> SEQ ID NO 1
<211> LENGTH: 16
<212> TYPE: PRT
<213> ORGANISM: Homo sapiens

<400> SEQUENCE: 1

Gly His Val Gly Trp Arg Glu Pro Ser Phe Met Ala Leu Ser Ala Ala
1               5                   10                  15

<210> SEQ ID NO 2
<211> LENGTH: 770
<212> TYPE: DNA
<213> ORGANISM: Artificial Sequence
<220> FEATURE:
<223> OTHER INFORMATION: Description of Artificial Sequence: Synthetic
      promoter sequence

<400> SEQUENCE: 2
tcaatattgg ccattagcca tattattcat tggttatata gcataaatca atattggcta      60
ttggccattg catacgttgt atctatatca taatatgtac atttatattg gctcatgtcc     120
aatatgaccg ccatgttggc attgattatt gactagttat taatagtaat caattacggg     180
gtcattagtt catagcccat atatggagtt ccgcgttaca taacttacgg taaatggccc     240
gcctggctga ccgcccaacg accccgccc attgacgtca ataatgacgt atgttcccat     300
agtaacgcca tagggactt tccattgacg tcaatgggtg gagtatttac ggtaaactgc     360
ccacttggca gtacatcaag tgtatcatat gccaagtccg cccctattg acgtcaatga     420 cggtaaatgg cccgcctggc attatgccca gtacatgacc ttacgggact ttcctacttg     480
gcagtacatc tacgtattag tcatcgctat taccatggtg atgcggtttt ggcagtacac     540
caatgggcgt ggatagcggt ttgactcacg gggatttcca agtctccacc ccattgacgt     600
caatgggagt ttgttttggc accaaaatca acgggacttt ccaaaatgtc gtaacaactg     660
```

-continued

```
cgatcgcccg ccccgttgac gcaaatgggc ggtaggcgtg tacggtggga ggtctatata    720
agcagagctc gtttagtgaa ccgtcagatc actagaagct ttattgcggt               770
```

<210> SEQ ID NO 3
<211> LENGTH: 770
<212> TYPE: DNA
<213> ORGANISM: Artificial Sequence
<220> FEATURE:
<223> OTHER INFORMATION: Description of Artificial Sequence: Synthetic
      promoter sequence

<400> SEQUENCE: 3

```
accgcaataa agcttctagt gatctgacgg ttcactaaac gagctctgct tatatagacc     60
tcccaccgta cacgcctacc gcccatttgc gtcaacgggg cgggcgatcg cagttgttac    120
gacattttgg aaagtcccgt tgattttggt gccaaaacaa actcccattg acgtcaatgg    180
ggtggagact tggaaatccc cgtgagtcaa accgctatcc acgccattg gtgtactgcc     240 aaaaccgcat caccatggta atagcgatga ctaaatacgta gatgtactgc caagtaggaa    300
agtcccgtaa ggtcatgtac tgggcataat gccaggcggg ccatttaccg tcattgacgt    360
caataggggg cggacttggc atatgataca cttgatgtac tgccaagtgg cagtttacc     420 gtaaatactc cacccattga cgtcaatgga aagtccctat ggcgttact atgggaacat    480 acgtcattat tgacgtcaat gggcgggggt cgttgggcgg tcagccaggc gggccattta   540
ccgtaagtta tgtaacgcgg aactccatat atgggctatg aactaatgac cccgtaattg    600
attactatta ataactagtc aataatcaat gccaacatgg cggtcatatt ggacatgagc    660
caatataaat gtacatatta tgatatagat acaacgtatg caatggccaa tagccaatat    720
tgatttatgc tatataacca atgaataata tggctaatgg ccaatattga               770
```

<210> SEQ ID NO 4
<211> LENGTH: 10
<212> TYPE: PRT
<213> ORGANISM: Homo sapiens

<400> SEQUENCE: 4

Trp Arg Glu Pro Ser Phe Met Ala Leu Ser
1               5                   10

<210> SEQ ID NO 5
<211> LENGTH: 6
<212> TYPE: PRT
<213> ORGANISM: Moloney murine leukemia virus

<400> SEQUENCE: 5

Gly Gly Trp Ser His Trp
1               5

<210> SEQ ID NO 6
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(48)

<400> SEQUENCE: 6

```
gga cat gta gga tgg aga gaa cca tca ttc atg gct ctg tca gct gca      48
Gly His Val Gly Trp Arg Glu Pro Ser Phe Met Ala Leu Ser Ala Ala
1               5                   10                  15
```

-continued

```
<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly His Val Gly Trp Arg Glu Pro Ser Phe Met Ala Leu Ser Ala Ala
1               5                   10                  15
```

METHODS AND COMPOSITIONS FOR TREATING METASTATIC CANCER

CROSS REFERENCE TO RELATED APPLICATIONS

This application claims priority from U.S. Provisional Application Ser. No. 60/464,571, filed Apr. 21, 2003, which is incorporated herein by reference.

TECHNICAL FIELD

The present invention relates generally to methods and compositions for treating neoplastic disorders. Further, the invention relates to methods and systems for producing therapeutically effective vectors.

BACKGROUND

Approximately 70% of all gene therapy protocols are aimed at treating metastatic cancer. The majority of active protocols involve some form of cancer immunotherapy via cell-based gene transfer of cytokines or tumor antigens, while others involve the intratumoral delivery of oncolytic viruses or vectors bearing prodrugs, chemoprotective agents, antisense constructs, or tumor suppressor genes. However, the major unresolved problem that has hindered the development and deployment of effective cancer gene therapy is that of inefficient delivery to target cells in vivo, a problem that obviates and precludes many direct therapeutic approaches (Tseng and Mulligan, Surg. Oncol. Clin. N. Am. 11:537-569, 2002). In this regard, the advent of pathotropic targeting launches a new paradigm in cancer gene therapy. By targeting the histopathology of the lesion—rather than the cancer cells per se—to optimize the effective vector concentration at metastatic sites, the safety and the efficacy of the circulating gene therapy vector was increased dramatically in preclinical studies (Gordon et al., Cancer Res. 60:3343-3347, 2000; Gordon et al., Hum. Gene Ther. 12:193-204, 2001). Further enhanced by the inherent properties of the murine leukemia virus-based vector (which selectively transduces dividing cells) and the strategic specificity of a cell cycle control gene which exhibits tumoricidal and anti-angiogenic activities (Gordon et al., Hum. Gene Ther. 12:193-204, 2001), the preclinical and clinical performance of the pathotropic vector establishes the potential for systemic delivery of genetic medicine for the physiologic surveillance and treatment of primary, remote, metastatic, and occult cancers.

Improved vectors, systems for producing the improved vectors, and treatment regimens for administering such vectors, are desired so that targeted delivery systems can be employed in a clinical setting.

SUMMARY

This disclosure relates to "targeted" viral and non-viral particles, including retroviral vector particles, adenoviral vector particles, adeno-associated virus vector particles, Herpes Virus vector particles, and pseudotyped viruses such as with the vesicular stomatitis virus G-protein (VSV-G), and to non-viral vectors that contain a viral protein as part of a virosome or other proteoliposomal gene transfer vector.

Also provided are novel retroviral expression systems for the generation of targeted viral particles, the use of transiently transfected human producer cells to produce the particles, a manufacturing process for large scale production of the viral particles, and methods for collecting and storing targeted viral vectors.

In one embodiment, a method for producing a targeted delivery vector is provided. The method includes transiently transfecting a producer cell with 1) a first plasmid comprising a nucleic acid sequence encoding the 4070A amphotropic envelope protein modified to contain a collagen binding domain; 2) a second plasmid comprising i) a nucleic acid sequence operably linked to a promoter, wherein the sequence encodes a viral gag-pol polypeptide; ii) a nucleic acid sequence operably linked to a promoter, wherein the sequence encodes a polypeptide that confers drug resistance on the producer cell; and iii) an SV40 origin of replication; 3) a third plasmid comprising i) a heterologous nucleic acid sequence operably linked to a promoter, wherein the sequence encodes a diagnostic or therapeutic polypeptide; ii) 5' and 3' long terminal repeat sequences; iii) a Ψ retroviral packaging sequence; iv) a CMV promoter upstream of the 5' LTR; v) a nucleic acid sequence operably linked to a promoter, wherein the sequence encodes a polypeptide that confers drug resistance on the producer cell; vi) an SV40 origin of replication. The producer cell is a human cell that expresses SV40 large T antigen. In ones aspect, the producer cell is a 293T cell.

The method further includes culturing the transfected producer cells of under conditions that allow the targeted delivery vector to be produced in the supernatant of the culture and isolating and introducing the supernatant in to a closed loop manifold system for collecting the vector. An exemplary closed loop manifold system is set forth in FIG. 19A and FIG. 19B. In one embodiment, the targeted delivery vector is a viral particle. In another embodiment, the targeted delivery vector is a non-viral particle.

In one aspect, the first plasmid is the Bv1/pCAEP plasmid, the second plasmid is the pCgpn plasmid, and the third plasmid is the pdnG1/C-REX plasmid or the pdnG1/C-REX II plasmid.

The collected particles generally exhibit a viral titer of about $1 \times 10^7$ to $1 \times 10^{10}$ colony forming units per milliliter. In addition, the viral particles are generally about 50 nm to 150 nm in diameter.

In one embodiment, the collagen binding domain includes a peptide derived from the D2 domain of von Willebrand factor. Generally, the von Willebrand factor is derived from a mammal. The peptide includes the amino acid sequence Gly-His-Val-Gly-Trp-Arg-Glu-Pro-Ser-Phe Met-Ala-Leu-Ser-Ala-Ala (SEQ ID NO:1). In another embodiment, the peptide is contained in the gp70 portion of the 4070A amphotropic envelope protein.

In another embodiment, the therapeutic polypeptide is an N-terminal deletion mutant of cyclin G1, interleukin-2 (IL-2), granulocyte macrophage-colony stimulating factor (GM-CSF), or thymidine kinase.

Targeted delivery vectors disclosed herein generally contain nucleic acid sequences encoding diagnostic or therapeutic polypeptides. As described in greater detail in other portions of this specification, exemplary therapeutic proteins and polypeptides of the invention include, but are in no way limited to, those of the classes of suicidal proteins, apoptosis-inducing proteins, cytokines, interleukins, and TNF family proteins. Exemplary diagnostic proteins or peptides, include for example, a green fluorescent protein and luciferase.

In another embodiment, a method of treating a subject having a neoplastic disorder is provided. The method include a first phase protocol comprising contacting a subject with a viral particle described herein, wherein the subject is contacted with i) a first viral particle dose level of about $1 \times 10^9$ to $6 \times 10^9$ Units/day administered to the subject for 1 to about 6 days in succession; ii) a second viral particle dose level of about $7 \times 10^9$ to about $1 \times 10^{10}$ Units/day administered to the subject for 1 to about 3 days in succession and subsequent to administration of the first vector dose; and iii) a viral particle dose level of about $1 \times 10^{10}$ to about $5 \times 10^{10}$ Units/day administered to the subject for 1 to about 3 days in succession and subsequent to administration of the second vector dose. The method further includes a second phase protocol comprising contacting a subject with a viral particle produced as described herein, wherein the subject is contacted with a viral particle dose level of about $1 \times 10^9$ to about $5 \times 10^{10}$ Units/day administered to the subject for 1 to about 15 days in succession and subsequent to the first phase protocol. The method optionally includes administering a chemotherapeutic agent to the subject prior to, contemporaneously with, or subsequent to the phase one and phase two protocols. The first viral particle dose level can be about $4 \times 10^9$ to $5 \times 10^9$ Units/day. The second viral particle dose level can be about $9 \times 10^9$ to about $1 \times 10^{10}$ Units/day. The third viral particle dose level can be about $1 \times 10^{10}$ to about $2 \times 10^{10}$ Units/day. Generally the viral particles accumulate in the subject in areas of exposed collagen. Such areas of exposed collagen include neoplastic lesions, areas of active angiogenesis, neoplastic lesions, areas of vascular injury, surgical sites, inflammatory sites and areas of tissue destruction.

Targeted delivery vectors disclosed herein can be administered topically, intravenously, intra-arterially, intracolonically, intratracheally, intraperitoneally, intranasally, intravascularly, intrathecally, intracranially, intramarrowly, intrapleurally, intradermally, subcutaneously, intramuscularly, intraocularly, intraosseously and/or intrasynovially.

In another embodiment, a plasmid including a multiple cloning site functionally-linked to a promoter, wherein the promoter supports expression of a heterologous nucleic acid sequence; 5' and 3' long terminal repeat sequences; a Ψ retroviral packaging sequence; a CMV promoter positioned upstream of the 5' LTR; a nucleic acid sequence operably linked to a promoter, wherein the sequence encodes a polypeptide that confers drug resistance on a producer cell containing the plasmid; and an SV40 origin of replication. Exemplary plasmids include pC-REX II or pC-REX. Additional derivatives of the exemplary include those that contain a heterologous nucleic acid sequence encoding a therapeutic or diagnostic polypeptide.

In other embodiments, a kit for the production of targeted delivery vectors is provided. The kit generally includes containers containing plasmids disclosed herein for the production of, for example, viral particle. Such kits can further include a producer cell suitable for transfecting with the plasmids, and instructions for transiently transfecting the producer cell with the plasmids. The instructions can further include methods for culturing the transfected producer cell under conditions that allow targeted delivery vectors to be produced. For example, a kit for the production of targeted viral particles can include containers containing the Bv1/pCAEP plasmid, the pCgpn plasmid, and the pdnG1/C-REX plasmid or the pdnG1/C-REX II plasmid. Such a kit can further include 293T cells and instructions for transiently transfecting cells with the plasmids and culturing the transfected cell under conditions that allow targeted viral particles to be produced.

In another embodiment, a kit for treating a neoplastic disorder is provided. The kit includes a container containing a viral particle produced by a method described herein in a pharmaceutically acceptable carrier and instructions for administering the viral particle to a subject. The administration can be according to the exemplary treatment protocol provided in Table 1.

In another embodiment, a method for conducting a gene therapy business is provided. The method includes generating targeted delivery vectors and establishing a bank of vectors by harvesting and suspending the vector particles in a solution of suitable medium and storing the suspension. The method further includes providing the particles, and instructions for use of the particles, to a physician or health care provider for administration to a subject (patient) in need thereof. Such instructions for use of the vector can include the exemplary treatment regimen provided in Table 1. The method optionally includes billing the patient or the patient's insurance provider.

In yet another embodiment, a method for conducting a gene therapy business, including providing kits disclosed herein to a physician or health care provider, is provided.

These, and other aspects, embodiments, objects and features of the present invention, as well as the best mode of practicing the same, will be more fully appreciated when the following detailed description of the invention is read in conjunction with the accompanying drawings.

DESCRIPTION OF THE DRAWINGS

FIG. 1A depicts a representative MRI from Patient #1 one day after completion of treatment cycle #1 showing a large round recurrent tumor (T; bracketed area) in the region of the pancreas within the area of the surgical bed and an enlarged para-aortic lymph node (N) indicating metastasis.

FIG. 1B depicts a follow-up MRI from Patient #1 four days after completion of treatment cycle #2 showing an irregularity in the shape of the recurrent tumor (T; bracketed area) with a large area of central necrosis (nec) involving 40-50% of the tumor mass, and a significant decrease in the size of the para-aortic lymph node metastasis (N).

FIG. 2A provides a representative abdominal CT scan from Patient #2 obtained at the beginning of treatment cycle #1 revealing a 6.0 cm3 mass in the region of the pancreatic head (T) encroaching on the superior mesenteric vein (SMV) and the superior mesenteric artery (SMA).

FIG. 2B provides a follow-up abdominal CT scan from Patient #2 two days after completion of treatment cycle #2, revealing that the pancreatic tumor mass (T) has decreased in size and regressed away from the superior mesenteric vessels (SMV and SMA). The start of each treatment cycle is indicated by arrows.

FIG. 1B depicts a restriction map of the pdnG1/C-REX plasmid. The plasmid is identical to the pC-REX plasmid shown in FIG. 11A except that it contains a nucleic acid sequence encoding the 209 aa (630 bp) dominant negative mutant dnG1 (472-1098 nt; 41-249 aa; Accession #U47413) which was prepared by PCR to include Not 1 and Sal 1 overhangs.

FIG. 18 depicts the nucleic acid sequence of the CMV promoter sequence from pIRES. Figure discloses SEQ ID NOS 2-3, respectively, in order of appearance.

FIG. 19B provides information regarding the components of the closed-loop manifold system.

DETAILED DESCRIPTION

Figure 1C:
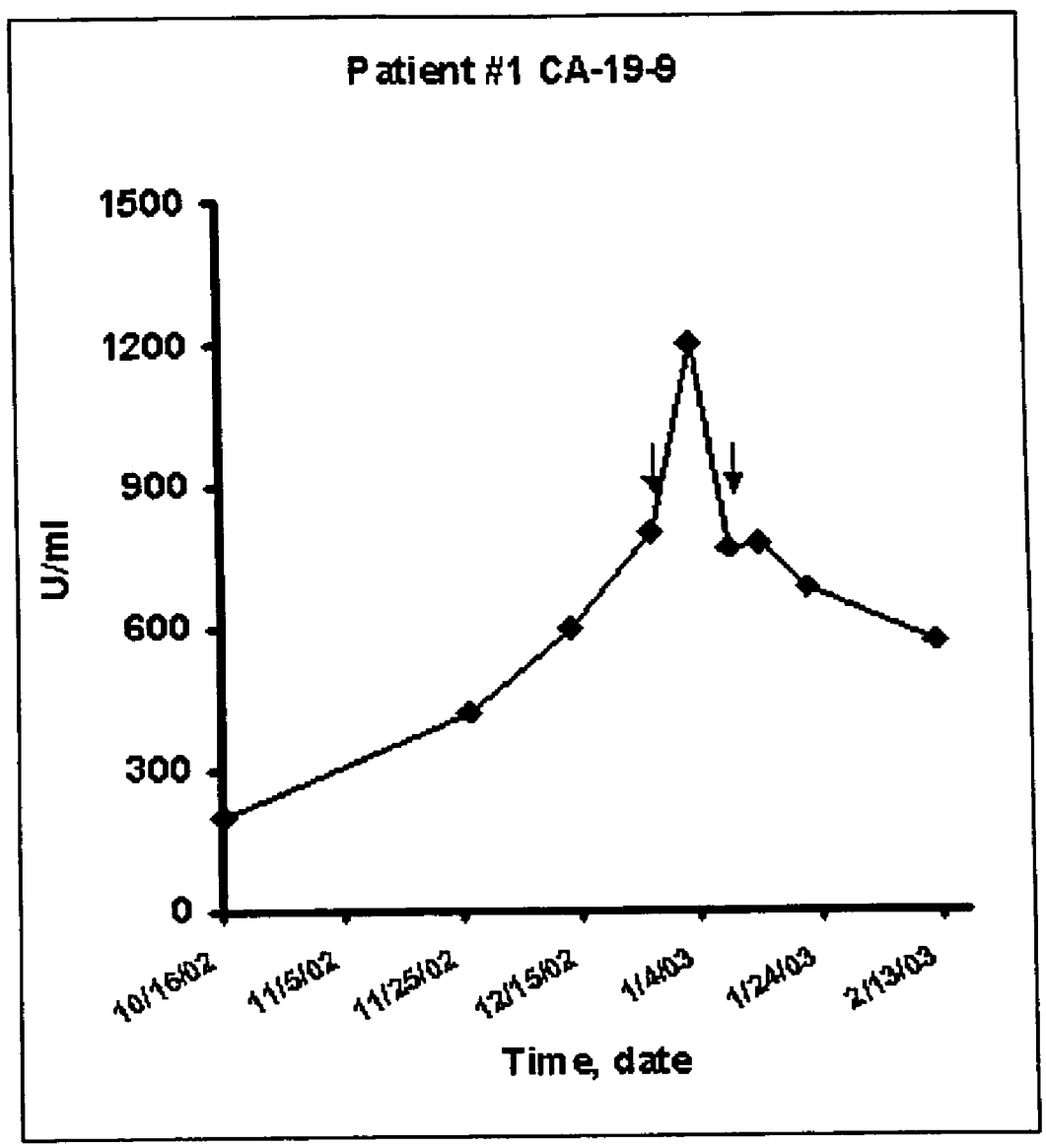
FIG. 1C is a graph showing that Rexin-G induces a reduction in CA19-9 serum level in Patient #1. Serum CA19-9 levels (U/ml), plotted on the vertical axis, are expressed as a function of time (date), plotted on the horizontal axis. The start of each treatment cycle is indicated by arrows.

The targeted delivery system targets retroviral vectors or any other viral or non-viral vector, protein or drug selectively to areas of pathology (i.e., pathotropic targeting), enabling preferential gene delivery to vascular (Hall et al., Hum Gene Ther, 8:2183-92, 1997; Hall et al., Hum Gene Ther, 11:983-93, 2000) or cancerous lesions (Gordon et al., Hum Gene Ther 12:193-204, 2001; Gordon et al., Curiel D T, Douglas J T, eds. *Vector Targeting Strategies for Therapeutic Gene Delivery*, New York, N.Y.: Wiley-Liss, Inc. 293-320, 2002), areas of active angiogenesis, and areas of tissue injury or inflammation with high efficiency in vivo.

The methods disclosed herein include the use of viral and non-viral particles that contain a modified surface protein for targeting the vector to the histopathology of a lesion—rather than the target cells per se—to optimize the effective vector concentration at areas of pathology. When injected intravenously, the pathotropic vector accumulates in cancerous lesions, areas of active angiogenesis, neoplastic lesions, metastatic sites, surgical sites, areas of vascular injury, inflammatory sites or any area of tissues destruction. This desired gain-of-function dramatically increases both the safety and the efficacy of the circulating gene therapy vector.

Definitions

Unless defined otherwise, all technical and scientific terms used herein have the same meaning as is commonly understood by one of skill in the art to which the invention(s) belong. All patents, patent applications, published applications and publications, Genbank sequences, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it understood that such identifiers can change and particular information on the internet can come and go, but equivalent information can be found by searching the internet. Reference thereto evidences the availability and public dissemination of such information.

As used herein, "nucleic acid" refers to a polynucleotide containing at least two covalently linked nucleotide or nucleotide analog subunits. A nucleic acid can be a deoxyribonucleic acid (DNA), a ribonucleic acid (RNA), or an analog of DNA or RNA. Nucleotide analogs are commercially available and methods of preparing polynucleotides containing such nucleotide analogs are known (Lin et al. (1994) Nucl. Acids Res. 22:5220-5234; Jellinek et al. (1995) Biochemistry 34:11363-11372; Pagratis et al. (1997) Nature Biotechnol. 15:68-73). The nucleic acid can be single-stranded, double-stranded, or a mixture thereof. For purposes herein, unless specified otherwise, the nucleic acid is double-stranded, or it is apparent from the context.

As used herein, DNA is meant to include all types and sizes of DNA molecules including cDNA, plasmids and DNA including modified nucleotides and nucleotide analogs.

As used herein, nucleotides include nucleoside mono-, di-, and triphosphates. Nucleotides also include modified nucleotides, such as, but are not limited to, phosphorothioate nucleotides and deazapurine nucleotides and other nucleotide analogs.

As used herein, the term "subject" refers to animals, plants, insects, and birds into which the large DNA molecules can be introduced. Included are higher organisms, such as mammals and birds, including humans, primates, rodents, cattle, pigs, rabbits, goats, sheep, mice, rats, guinea pigs, cats, dogs, horses, chicken and others.

As used herein, "administering to a subject" is a procedure by which one or more delivery agents and/or large nucleic acid molecules, together or separately, are introduced into or applied onto a subject such that target cells which are present in the subject are eventually contacted with the agent and/or the large nucleic acid molecules.

As used herein, "targeted delivery vector" or "targeted delivery vehicle" refers to both viral and non-viral particles that harbor and transport exogenous nucleic acid molecules to a target cell or tissue. Viral vehicles include, but are not limited to, retoviruses, adenoviruses and adeno-associated viruses. Non-viral vehicles include, but are not limited to, microparticles, nanoparticles, virosomes and liposomes. "Targeted," as used herein, refers to the use of ligands that are associated with the delivery vehicle and target the vehicle to a cell or tissue. Ligands include, but are not limited to, antibodies, receptors and collagen binding domains.

As used herein, "delivery," which is used interchangeably with "transduction," refers to the process by which exogenous nucleic acid molecules are transferred into a cell such that they are located inside the cell. Delivery of nucleic acids is a distinct process from expression of nucleic acids.

As used herein, a "multiple cloning site (MCS)" is a nucleic acid region in a plasmid that contains multiple restriction enzyme sites, any of which can be used in conjunction with standard recombinant technology to digest the vector. "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector.

As used herein, "origin of replication" (often termed "ori"), is a specific nucleic acid sequence at which replication is initiated. Alternatively an autonomously replicating sequence (ARS) can be employed if the host cell is yeast.

As used herein, "selectable or screenable markers" confer an identifiable change to a cell permitting easy identification of cells containing an expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is calorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

The term "transfection" is used to refer to the uptake of foreign DNA by a cell. A cell has been "transfected" when exogenous DNA has been introduced inside the cell membrane. A number of transfection techniques are generally known in the art. See, e.g., Graham et al., Virology 52:456 (1973); Sambrook et al., Molecular Cloning: A Laboratory Manual (1989); Davis et al., Basic Methods in Molecular Biology (1986); Chu et al., Gene 13:197 (1981). Such techniques can be used to introduce one or more exogenous DNA moieties, such as a nucleotide integration vector and other nucleic acid molecules, into suitable host cells. The term captures chemical, electrical, and viral-mediated transfection procedures.

As used herein, "expression" refers to the process by which nucleic acid is translated into peptides or is transcribed into RNA, which, for example, can be translated into peptides, polypeptides or proteins. If the nucleic acid is derived from genomic DNA, expression may, if an appropriate eukaryotic host cell or organism is selected, include splicing of the mRNA. For heterologous nucleic acid to be expressed in a host cell, it must initially be delivered into the cell and then, once in the cell, ultimately reside in the nucleus.

As used herein, "applying to a subject" is a procedure by which target cells present in the subject are eventually contacted with energy such as ultrasound or electrical energy. Application is by any process by which energy can be applied.

The term "host cell" denotes, for example, microorganisms, yeast cells, insect cells, and mammalian cells, that can be, or have been, used as recipients for multiple constructs for producing a targeted delivery vector. The term includes the progeny of the original cell which has been transfected. Thus, a "host cell" as used herein generally refers to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, "genetic therapy" involves the transfer of heterologous DNA to the certain cells, target cells, of a mammal, particularly a human, with a disorder or conditions for which therapy or diagnosis is sought. The DNA is introduced into the selected target cells in a manner such that the heterologous DNA is expressed and a therapeutic product encoded thereby is produced. Alternatively, the heterologous DNA may in some manner mediate expression of DNA that encodes the therapeutic product, it may encode a product, such as a peptide or RNA that in some manner mediates, directly or indirectly, expression of a therapeutic product. Genetic therapy may also be used to deliver nucleic acid encoding a gene product to replace a defective gene or supplement a gene product produced by the mammal or the cell in which it is introduced. The introduced nucleic acid may encode a therapeutic compound, such as a growth factor inhibitor thereof, or a tumor necrosis factor or inhibitor thereof, such as a receptor therefor, that is not normally produced in the mammalian host or that is not produced in therapeutically effective amounts or at a therapeutically useful time. The heterologous DNA encoding the therapeutic product may be modified prior to introduction into the cells of the afflicted host in order to enhance or otherwise alter the product or expression thereof.

As used herein, "heterologous nucleic acid sequence" is typically DNA that encodes RNA and proteins that are not normally produced in vivo by the cell in which it is expressed or that mediates or encodes mediators that alter expression of endogenous DNA by affecting transcription, translation, or other regulatable biochemical processes. A heterologous nucleic acid sequence may also be referred to as foreign DNA. Any DNA that one of skill in the art would recognize or consider as heterologous or foreign to the cell in which it is expressed is herein encompassed by heterologous DNA. Examples of heterologous DNA include, but are not limited to, DNA that encodes traceable marker proteins, such as a protein that confers drug resistance, DNA that encodes therapeutically effective substances, such as anti-cancer agents, enzymes and hormones, and DNA that encodes other types of proteins, such as antibodies. Antibodies that are encoded by heterologous DNA may be secreted or expressed on the surface of the cell in which the heterologous DNA has been introduced.

Plasmids

Plasmids disclosed herein are used to transfect and produce targeted delivery vectors for use in therapeutic and diagnostic procedures. In general, such plasmids provide nucleic acid sequences that encode components, viral or non-viral, of targeted vectors disclosed herein. Such plasmids include nucleic acid sequences that encode, for example the 4070A amphotropic envelope protein modified to contain a collagen binding domain. Additional plasmids can include a nucleic acid sequence operably linked to a promoter. The sequence generally encodes a viral gag-pol polypeptide. The plasmid further includes a nucleic acid sequence operably linked to a promoter, and the sequence encodes a polypeptide that confers drug resistance on the producer cell. An origin of replication is also included. Additional plasmids can include a heterologous nucleic acid sequence encoding a diagnostic or therapeutic polypeptide, 5' and 3' long terminal repeat sequences; a T retroviral packaging sequence, a CMV promoter upstream of the 5' LTR, a nucleic acid sequence operably linked to a promoter, and an SV40 origin of replication.

The heterologous nucleic acid sequence generally encodes a diagnostic or therapeutic polypeptide. In specific embodiments, the therapeutic polypeptide or protein is a "suicide protein" that causes cell death by itself or in the presence of other compounds. A representative example of such a suicide protein is thymidine kinase of the herpes simplex virus. Additional examples include thymidine kinase of varicella zoster virus, the bacterial gene cytosine deaminase (which converts 5-fluorocytosine to the highly toxic compound 5-fluorouracil), p450 oxidoreductase, carboxypeptidase G2, beta-glucuronidase, penicillin-V-amidase, penicillin-G-amidase, beta-lactamase, nitroreductase, carboxypeptidase A, linamarase (also referred to as .beta.-glucosidase), the *E. coli* gpt gene, and the *E. coli* Deo gene, although others are known in the art. In some embodiments, the suicide protein converts a prodrug into a toxic compound. As used herein, "prodrug" means any compound useful in the methods of the present invention that can be converted to a toxic product, i.e. toxic to tumor cells. The prodrug is converted to a toxic product by the suicide protein. Representative examples of such prodrugs include: ganciclovir, acyclovir, and FIAU (1-(2-deoxy-2-fluoro-.beta.-D-arabinofuranosyl)-5-iod-ouracil) for thymidine kinase; ifosfamide for oxidoreductase; 6-methoxypurine arabinoside for VZV-TK; 5-fluorocytosine for cytosine deaminase; doxorubicin for beta-glucuronidase; CB1954 and nitrofurazone for nitroreductase; and N-(Cyanoacetyl)-L-phenylalanine or N-(3-chloropropionyl)-L-phenylalanine for carboxypeptidase A. The prodrug may be administered readily by a person having ordinary skill in this art. A person with ordinary skill would readily be able to determine the most appropriate dose and route for the administration of the prodrug.

In some embodiments, a therapeutic protein or polypeptide, is a cancer suppressor, for example p53 or Rb, or a nucleic acid encoding such a protein or polypeptide. Of course, those of skill know of a wide variety of such cancer suppressors and how to obtain them and/or the nucleic acids encoding them.

Other examples of therapeutic proteins or polypeptides include pro-apoptotic therapeutic proteins and polypeptides, for example, p15, p16, or p21.sup.WAF-1.

Cytokines, and nucleic acid encoding them may also be used as therapeutic proteins and polypeptides. Examples include: GM-CSF (granulocyte macrophage colony stimulating factor); TNF-alpha (Tumor necrosis factor alpha); Interferons including, but not limited to, IFN-alpha and IFN-gamma; and Interleukins including, but not limited to, Interleukin-1 (IL1), Interleukin-Beta (IL-beta), Interleukin-2 (IL2), Interleukin-4 (IL4), Interleukin-5 (IL5), Interleukin-6 (IL6), Interleukin-8 (IL8), Interleukin-10 (IL10), Interleukin-12 (IL12), Interleukin-13 (IL13), Interleukin-14 (IL14), Interleukin-15 (IL15), Interleukin-16 (IL16), Interleukin-18 (IL18), Interleukin-23 (IL23), Interleukin-24 (IL24), although other embodiments are known in the art.

Additional examples of cytocidal genes includes, but is not limited to, mutated cyclin G1 genes. By way of example, the cytocidal gene may be a dominant negative mutation of the cyclin G1 protein (e.g., WO/01/64870).

Previously, retroviral vector (RV) constructs were generally produced by the cloning and fusion of two separate retroviral (RV) plasmids: one containing the retroviral LTRs, packaging sequences, and the respective gene(s) of interest; and another retroviral vector containing a strong promoter (e.g., CMV) as well as a host of extraneous functional sequences. The pC-REX II (e-REX) vector disclosed herein refers to an improved plasmid containing an insertion of a unique set of cloning sites in the primary plasmid to facilitate directional cloning of the experimental gene(s). The strong promoter (ex, CMV) is employed in the plasmid backbone to increase the amount of RNA message generated within the recipient producer cells but is not itself packaged into the retroviral particle, as it lies outside of the gene-flanking retroviral LTR's.

Figure 11A:
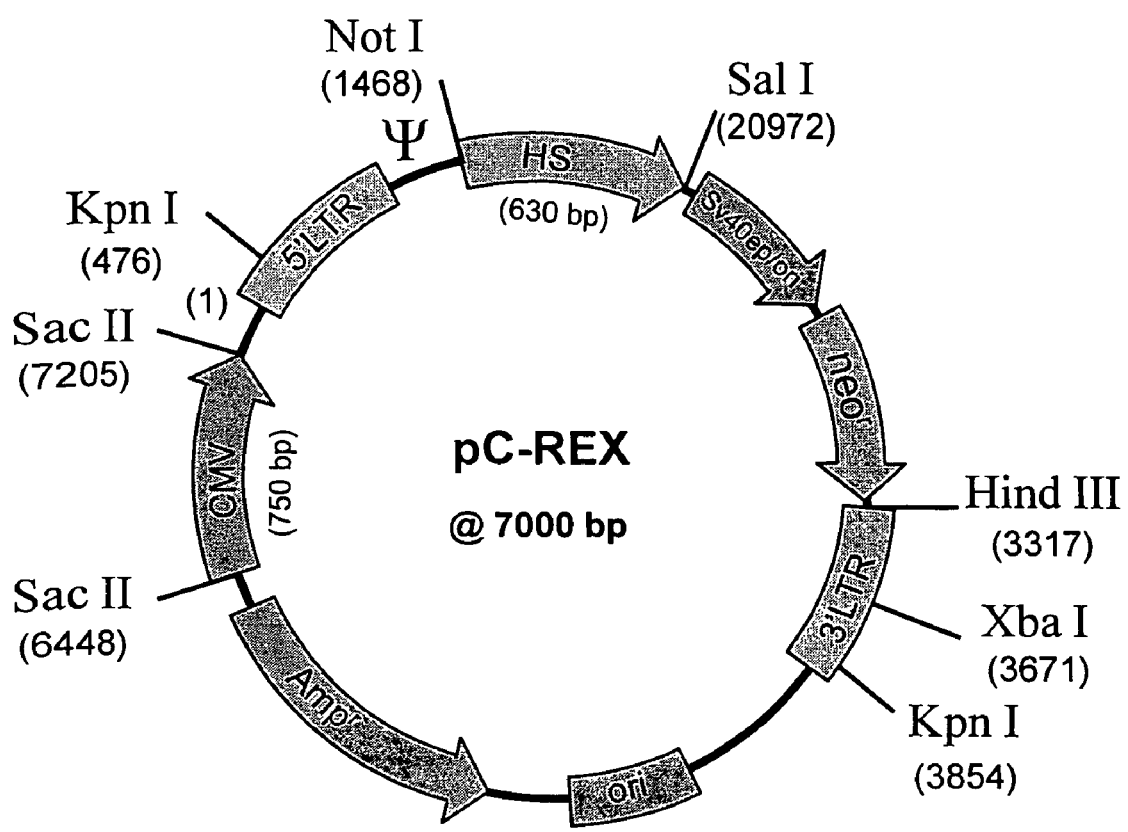
FIG. 11A depicts a restriction map of the pC-REX plasmid. The plasmid is derived from G1XSvNa (Genetic Therapy, Inc.), into which the CMV i.e. promoter enhancer was cloned at the unique Sac II site upstream of the 5' LTR. A heterologous nucleic acid sequence (HS) encoding a diagnostic or therapeutic polypeptide can be included between the Not 1 and Sal 1 restriction sites. The neo gene is driven by the SV40 e.p. with its nested ori. The resulting pC-REX plasmid was designed for high-titer vector production in 293T cells.
Figure 11:
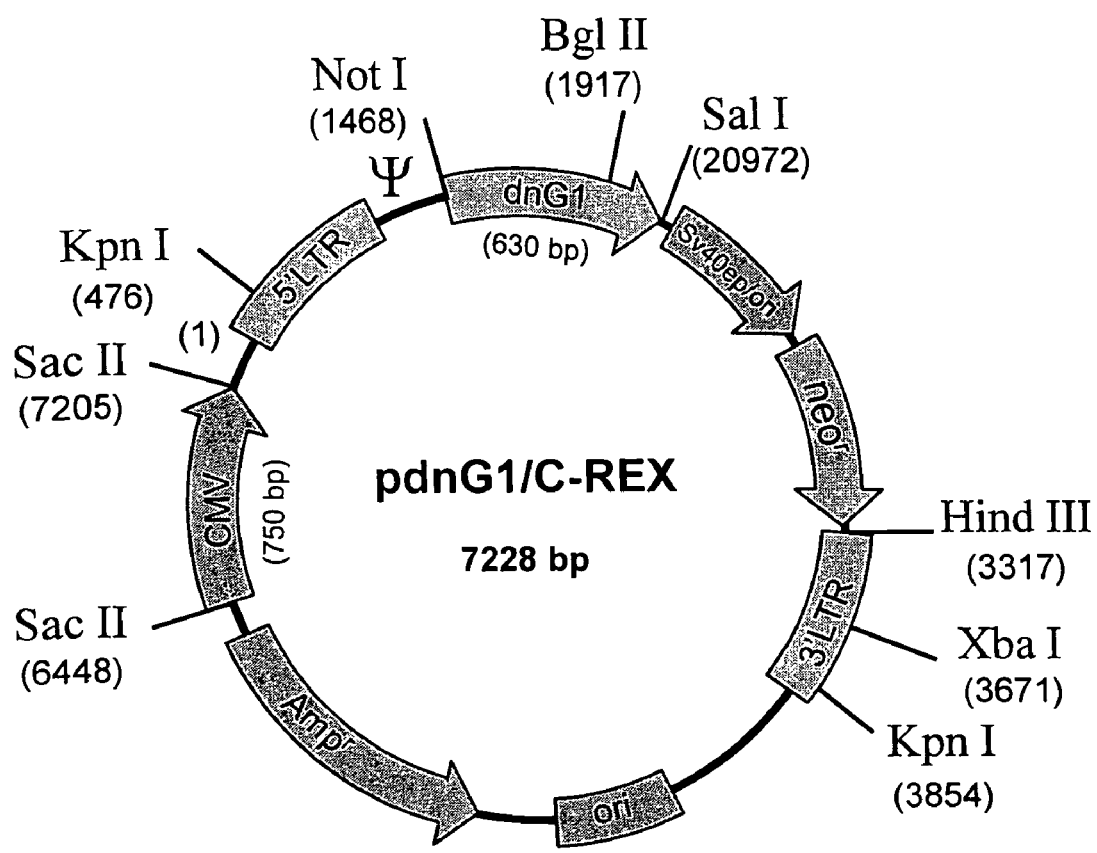
FIG. 11C depicts a restriction digest of pdnG1/C-REX.
Figure 11C:
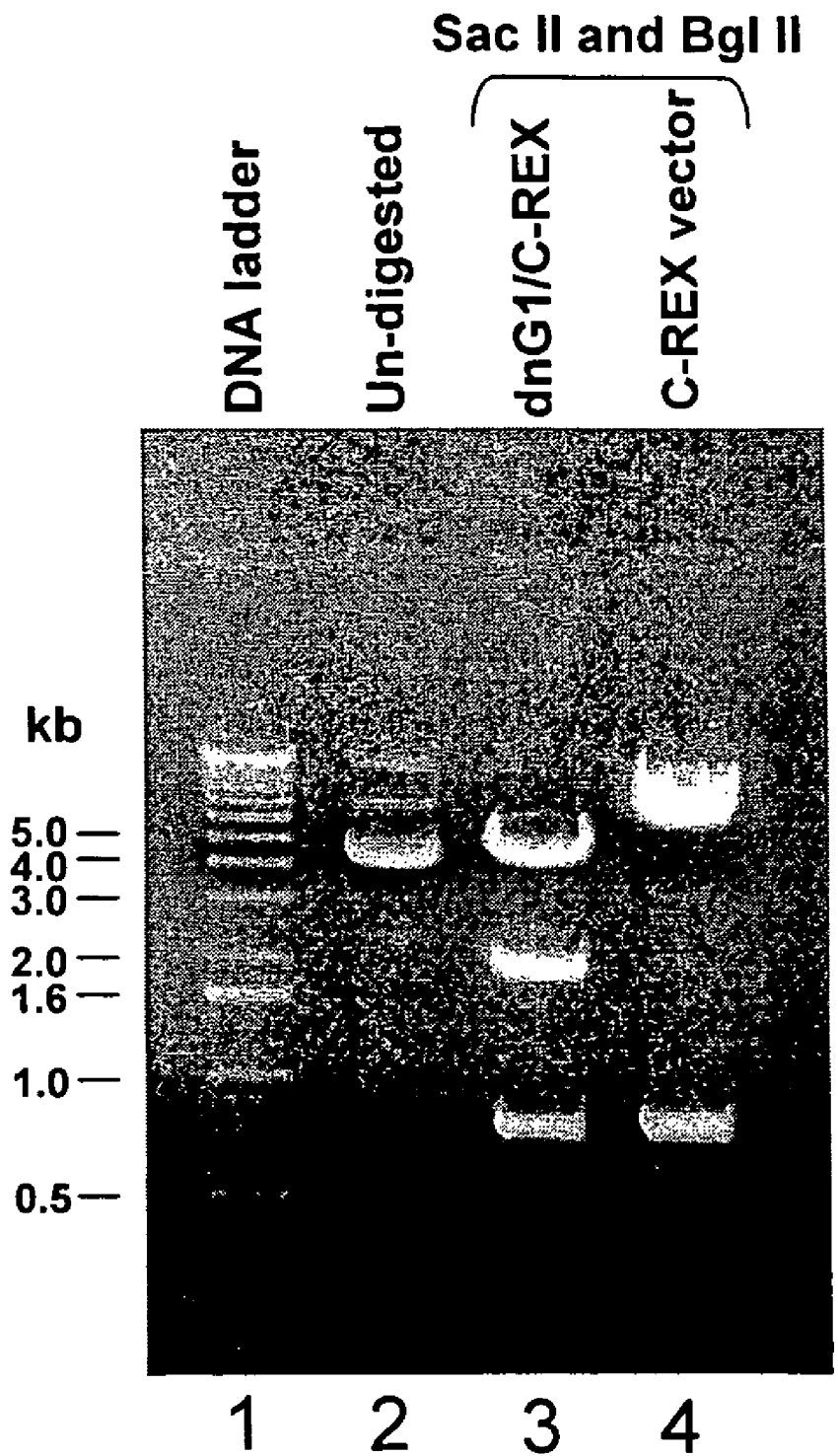
Figure 12A:
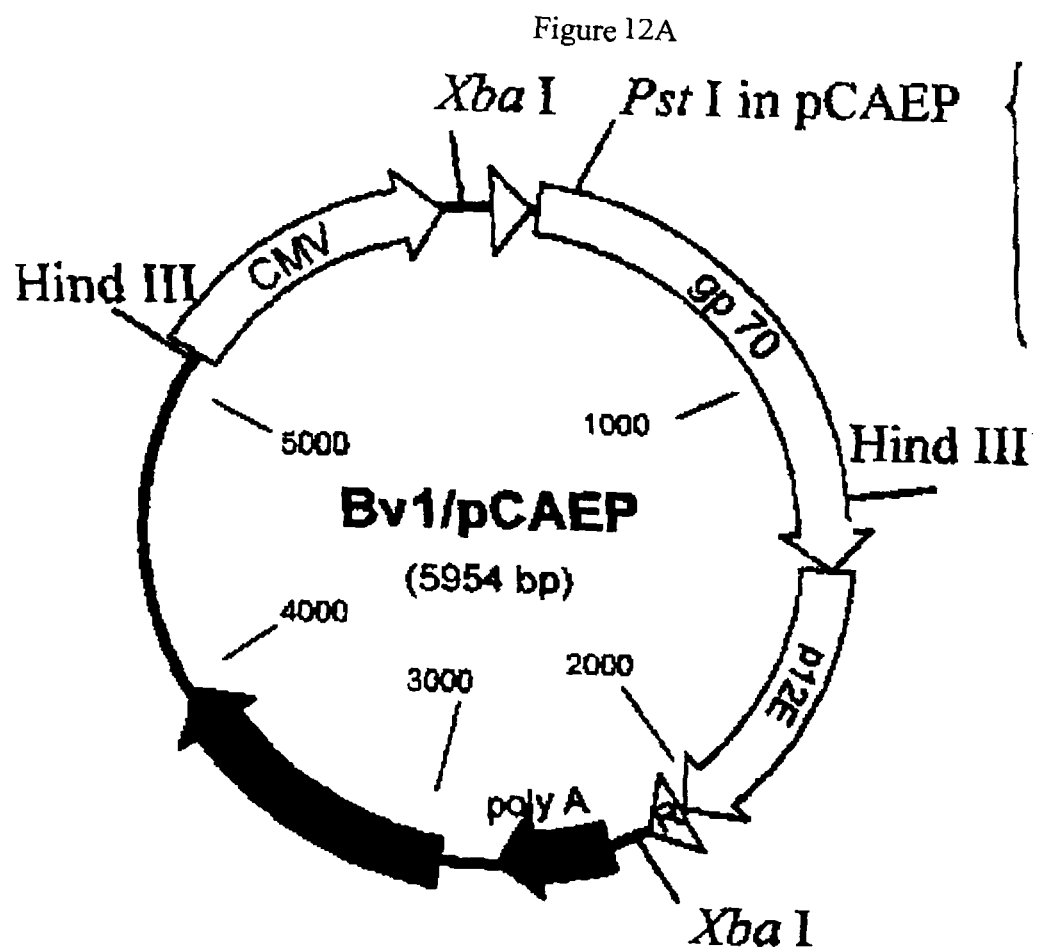
FIG. 12A depicts a restriction map of the Bv1/pCAEP plasmid. CAEP (P=Pst 1) was created by the addition of a unique Pst 1 site near the N-terminus of the CAE amphotropic envelope protein (4070A), between aa 6 and 7 of the mature gp70 polypeptide. Bv1 is a collagen-binding decapeptide derived from vWF, flanked by strategic linkers, and inserted as in-frame coding sequences into the Pst 1 site of PCAEP.
Figure 12B:
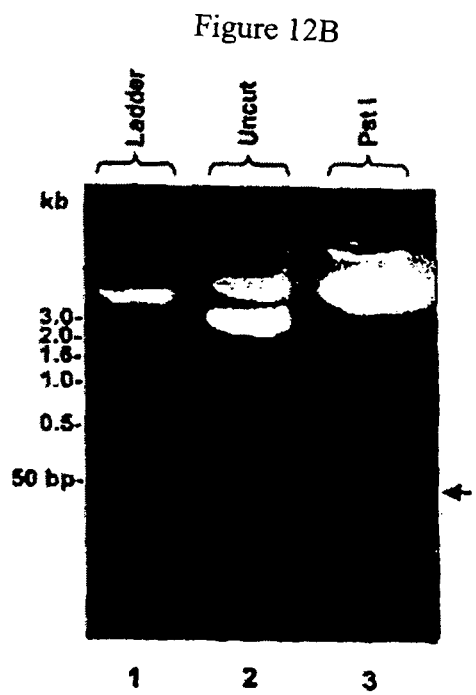
FIG. 12B depicts a restriction digest of Bv1/pCAEP.
Figure 13A:
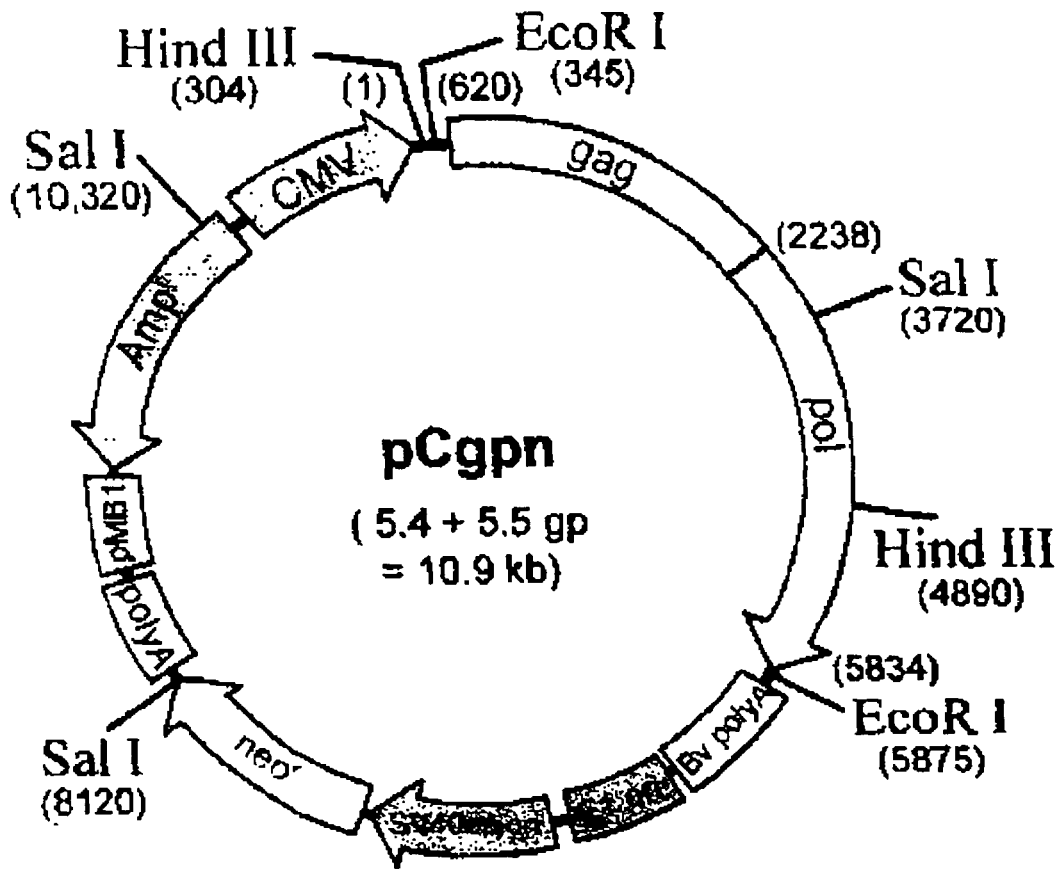
FIG. 13A depicts a restriction map of the pCgpn plasmid. This plasmid encodes the MoMuLv gag-pol driven by the CMV immediate-early promoter enhancer. The gag-pol coding sequence flanked by EcoR 1 cloning sites was derived from clone 3PO as pGag-pol-gpt (Moarkowitz et al., 1988). The vector backbone is pcDNA3.1+ (Invitrogen). Polyadenylation signal and transcription termination sequences from bovine growth hormone enhance RNA stability. An SV40 ori is featured along with the e.p. for episomal replication in cell lines that express SV40 large T antigen.
Figure 13B:
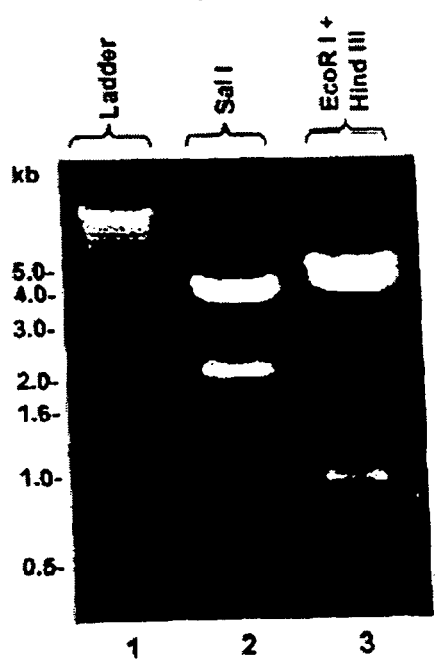
FIG. 13B depicts a restriction digest of pCgpn.
Figure 14:
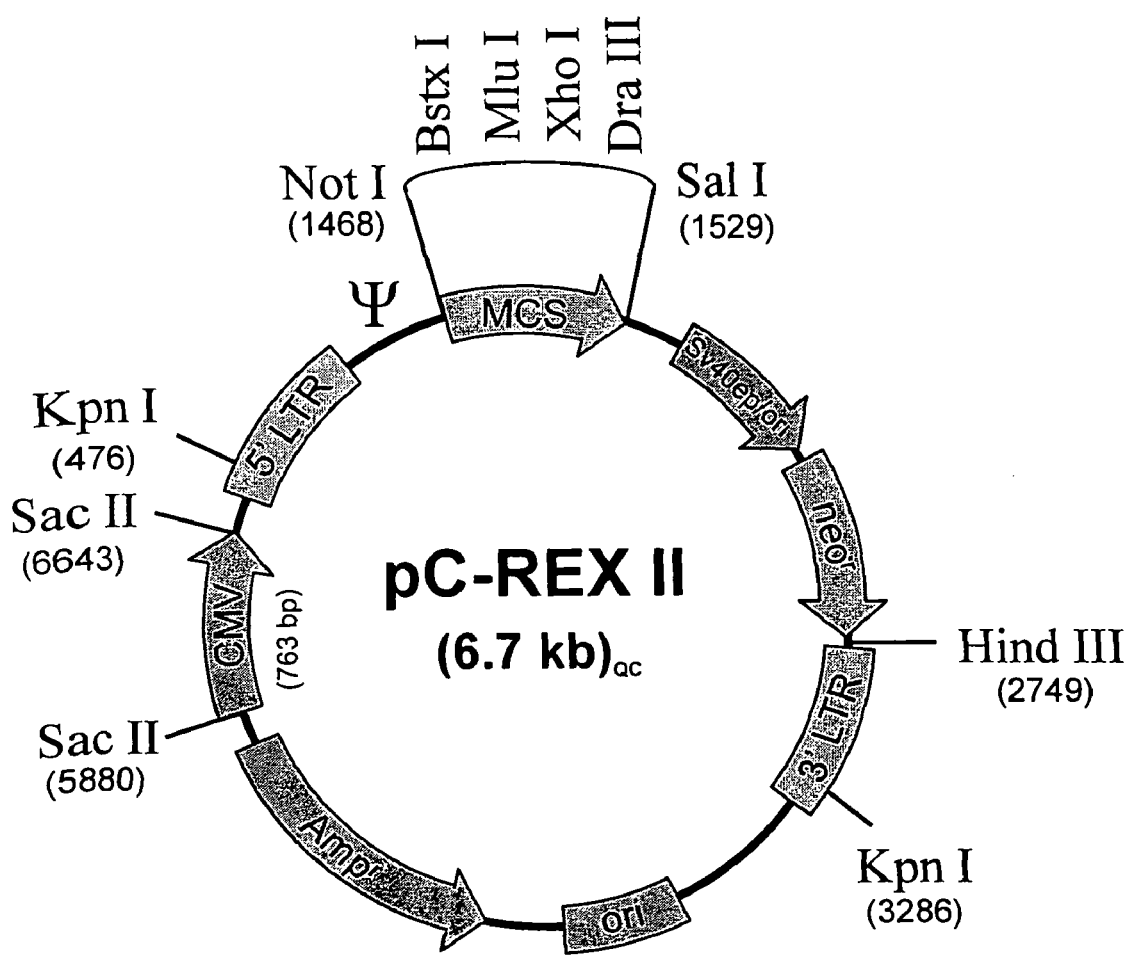
FIG. 14 depicts a map of the novel pC-REX II (i.e., EPEIUS-REX) plasmid.
Figure 15:
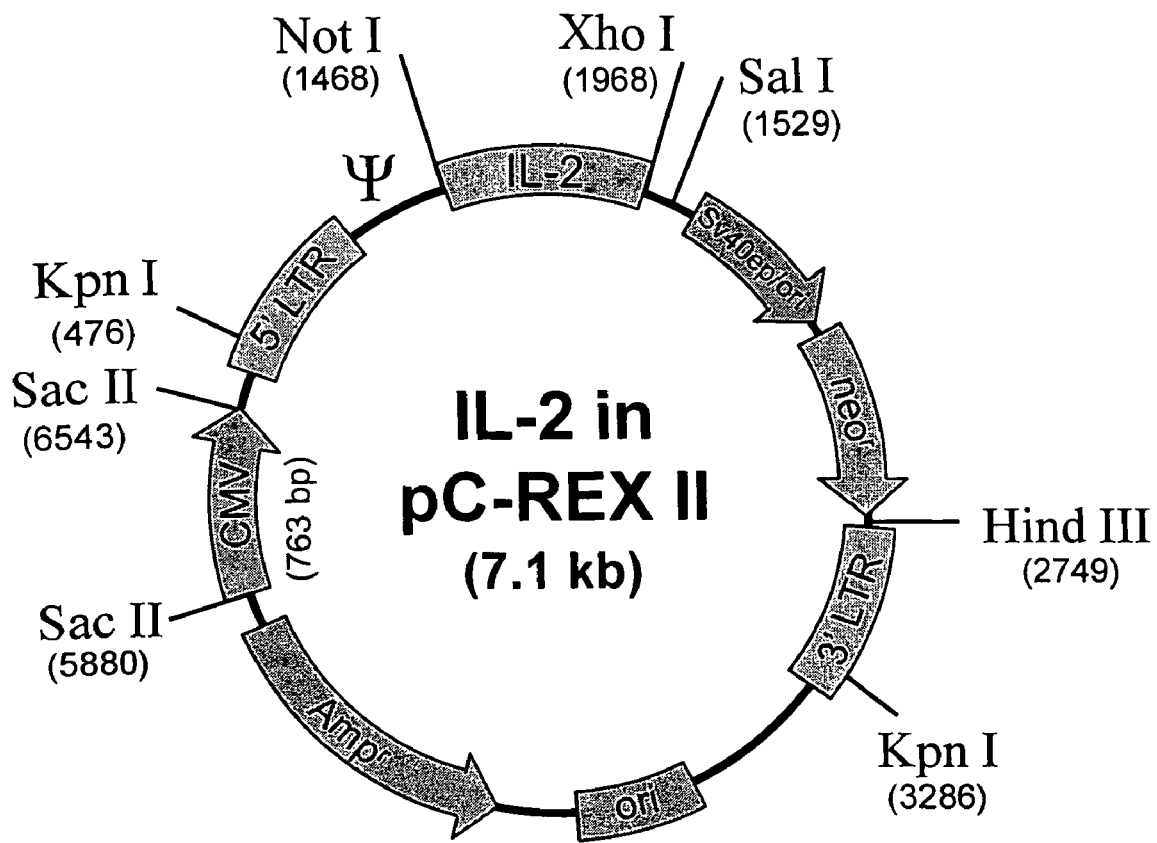
FIG. 15 depicts a map of the novel pC-REX II (i.e., EPEIUS-REX) plasmid with the therapeutic cytokine gene IL-2 inserted.
Figure 16:
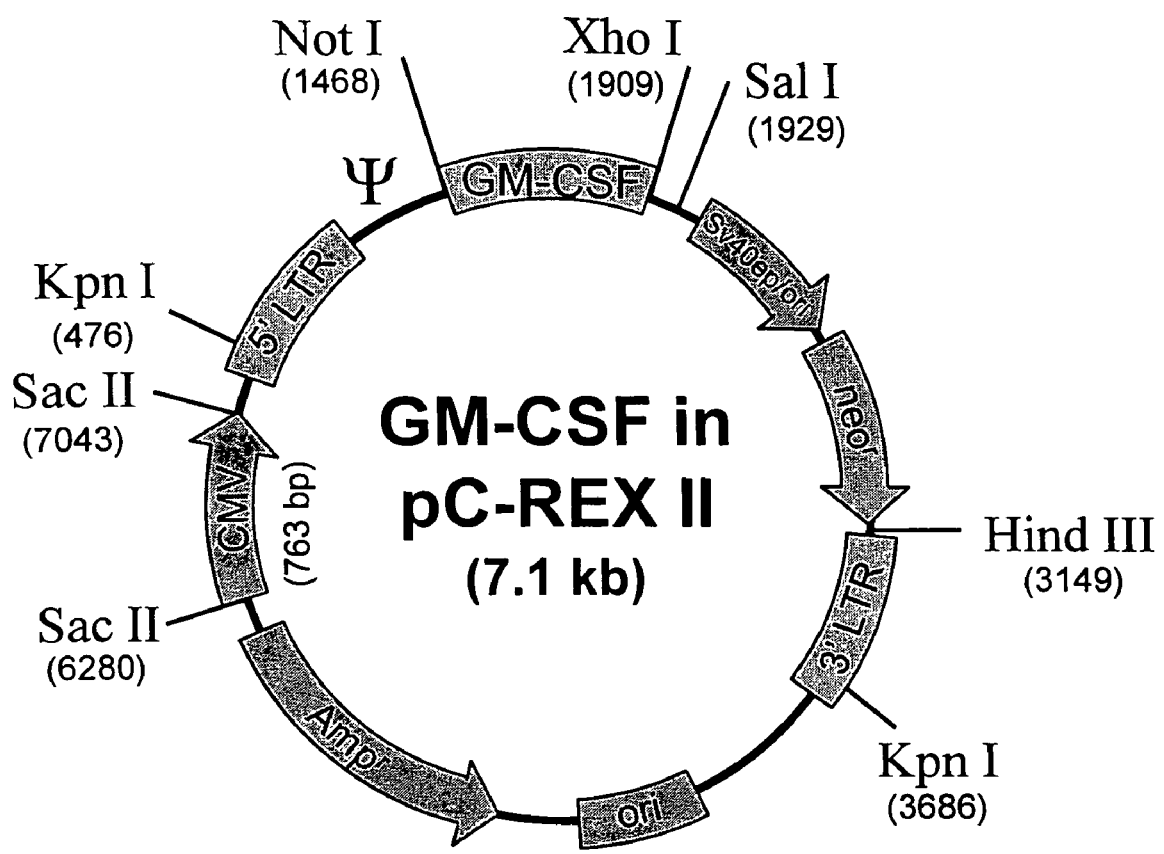
FIG. 16 depicts a map of the novel pC-REX II (i.e., EPEIUS-REX) plasmid with the therapeutic cytokine gene GM-CSF inserted.
Figure 17:
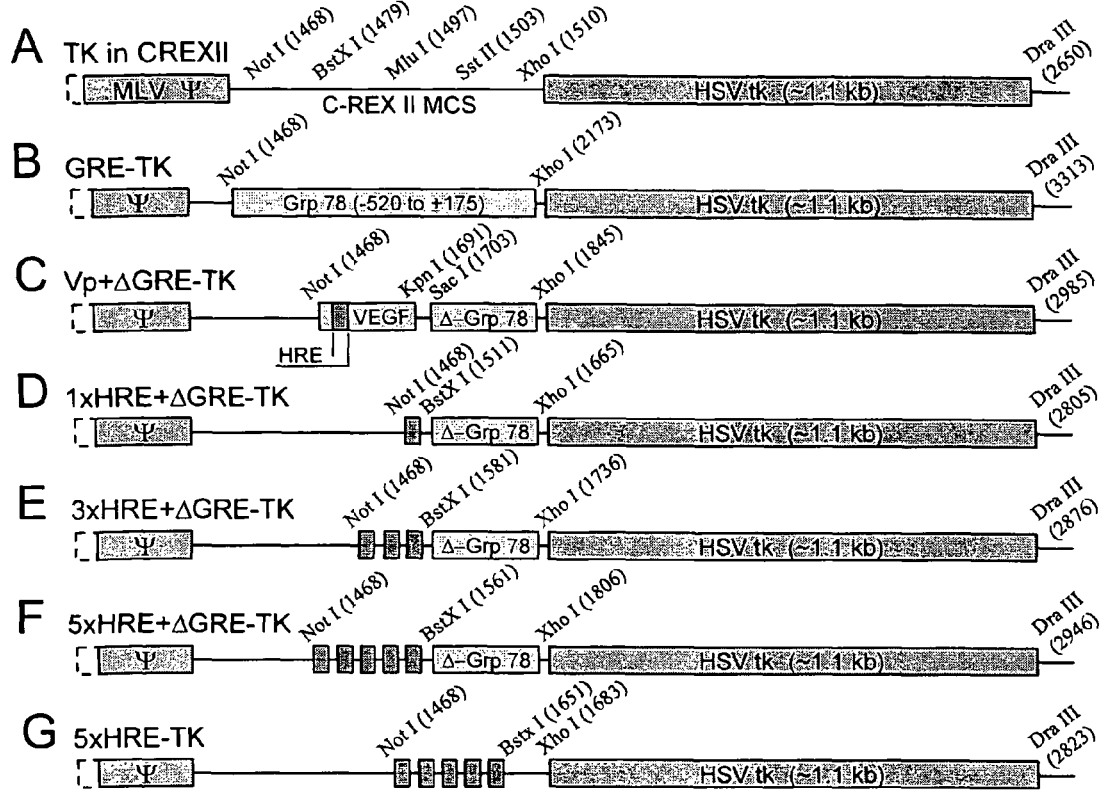
FIG. 17A-G depicts a complex series of auxiliary promoters proximal to the HStk (reporter) gene utilizing the MCS sites of pC-REX II.
FIG. 17H depicts a Western blot of differential gene expression in tumor cells from the auxiliary promoters shown in FIGS. 17A-G.
Figure 17H:
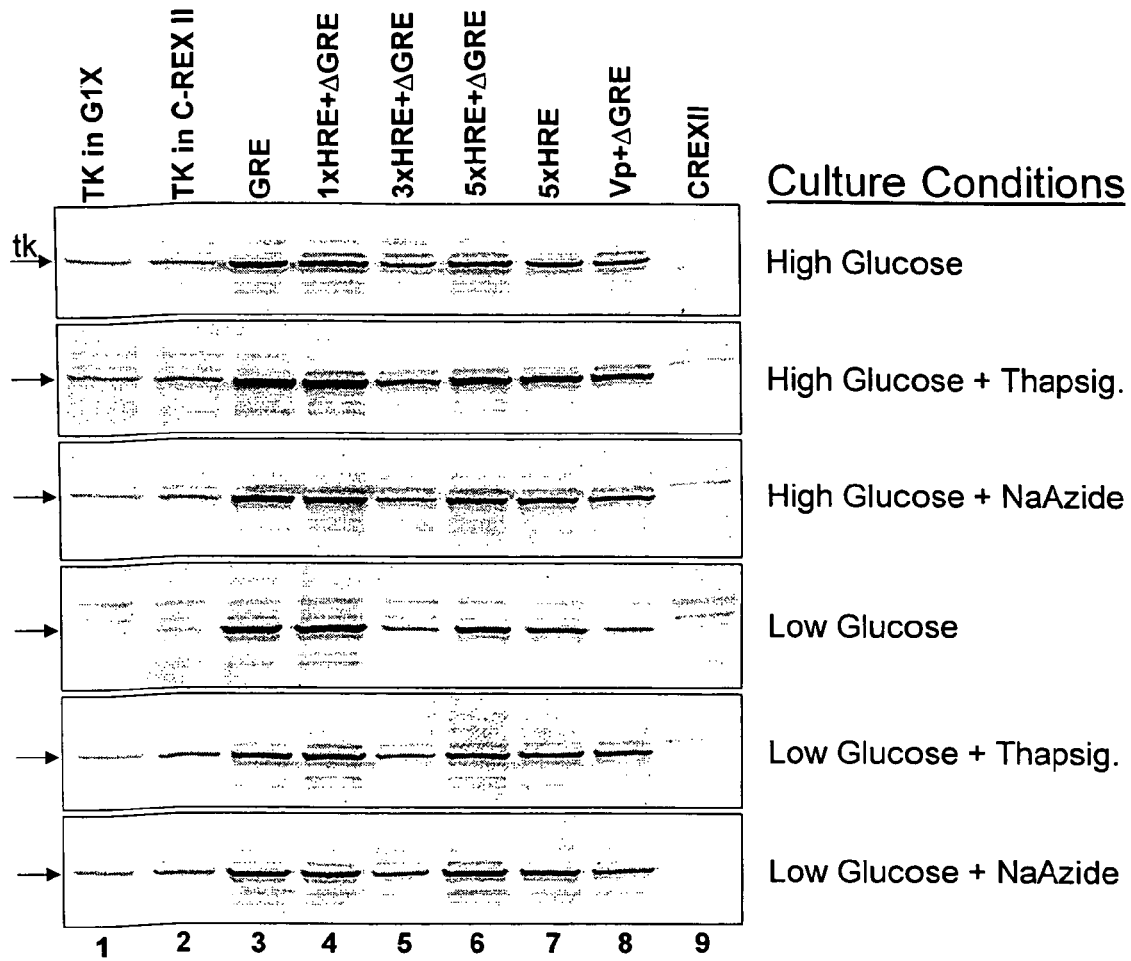

Therefore, an improved plasmid was designed which included the strong CMV promoter (obtained by PCR) into a strategic site within the G1xSvNa vector, which was previously approved for human use by the FDA, thus eliminating the plasmid size and sequence concerns of previously reported vectors. This streamlined construct was designated pC-REX. PC-REX was further modified to incorporate a series of unique cloning sites (see MCS in pC-REX II, FIG. 14), enabling directional cloning and/or the insertion of multiple genes as well as auxiliary functional domains. Thus, the new plasmids are designated pC-REX and pC-REX II (EPEIUS-REX or eREX). The pC-REX plasmid design (see FIG. 11A) outperformed that of pHIT-112/pREX in direct side-by-side comparisons. The new plasmid design was further modified to include the coding sequence of various therapeutically effective polypeptides. In one example, the dominant negative Cyclin G1 (dnG1) (see FIG. 11B) was included as the therapeutic gene. The tripartite viral particle (env, gag-pol, and dnG1 gene vector construct) has been referred to collectively as REXIN-GTM in published reports of the clinical trials. Thus, REXIN-G represents the targeted delivery vector dnG1/C-REX that is packaged, encapsidated, and enveloped in a targeted, injectable viral particle.

A targeting ligand is included in a plasimd disclosed herein. Generally, it is inserted between two consecutively numbered amino acid residues of the native (i.e., unmodified) receptor binding region of the retroviral envelope encoded by a nucleic acid sequence of a plasmid, such as in the modified amphotropic CAE envelope polypeptide, wherein the targeting polypeptide is inserted between amino acid residues 6 and 7. The polypeptide is a portion of a protein known as gp70, which is included in the amphotropic envelope of Moloney Murine Leukemia Virus. In general, the targeting polypeptide includes a binding region which binds to an extracellular matrix component, including, but not limited to, collagen (including collagen Type I and collagen Type IV), laminin, fibronectin, elastin, glycosaminoglycans, proteoglycans, and sequences which bind to fibronectin, such as arginine-glycine-aspartic acid, or RGD, sequences. Binding regions which may be included in the targeting polypeptide include, but are not limited to, polypeptide domains which are functional domains within von Willebrand Factor or derivatives thereof, wherein such polypeptide domains bind to collagen. In one embodiment, the binding region is a polypeptide having the following structural formula: Trp-Arg-Glu-Pro-Ser-Phe-Met-Ala-Leu-Ser (SEQ ID NO: 4).

Methods for Producing Targeted Vectors

This disclosure relates to the production of viral and non-viral vector particles, including retroviral vector particles, adenoviral vector particles, adeno-associated virus vector particles, Herpes Virus vector particles, pseudotyped viruses, and non-viral vectors having a modified, or targeted viral surface protein, such as, for example, a targeted viral envelope polypeptide, wherein such modified viral surface protein, such as a modified viral envelope polypeptide, includes a targeting polypeptide including a binding region which binds to an extracellular matrix component such as collagen. The targeting polypeptide may be placed between two consecutive amino acid residues of the viral surface protein, or may replace amino acid residues which have been removed from the viral surface protein.

One of the most frequently used delivery systems for achieving gene therapy involves viral vectors, most commonly adenoviral and retroviral vectors. Exemplary viral-based vehicles include, but are not limited to, recombinant retroviruses (see, e.g., WO 90/07936; WO 94/03622; WO 93/25698; WO 93/25234; U.S. Pat. No. 5,219,740; WO 93/11230; WO 93/10218; U.S. Pat. No. 4,777,127; GB Patent No. 2,200,651; EP 0 345 242; and WO 91/02805), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., WO 94/12649, WO 93/03769; WO 93/19191; WO 94/28938; WO 95/11984 and WO 95/00655). Administration of DNA linked to killed adenovirus as described in Curiel, Hum. Gene Ther. (1992) 3:147 can also be employed.

For gene delivery purposes, a viral particle can be developed from a virus that is native to a target cell or from a virus that is non-native to a target cell. In general, it is desirable to use a non-native virus vector rather than a native virus vector. While native virus vectors may possess a natural affinity for target cells, such viruses pose a greater hazard since they possess a greater potential for propagation in target cells. In this regard, animal virus vectors, wherein they are not naturally designed for propagation in human cells, can be useful for gene delivery to human cells. In order to obtain sufficient yields of such animal virus vectors for use in gene delivery, however, it is necessary to carry out production in a native animal packaging cell. Virus vectors produced in this way, however, normally lack any components either as part of the envelope or as part of the capsid that can provide tropism for human cells. For example, current practices for the production of non-human virus vectors, such as ecotropic mouse (murine) retroviruses like MMLV, are produced in a mouse packaging cell line. Another component required for human cell tropism must be provided.

In general, the propagation of a viral vector (without a helper virus) proceeds in a packaging cell in which a nucleic acid sequence for packaging components were stably integrated into the cellular genome and nucleic acid coding for viral nucleic acid is introduced in such a cell line. Packaging lines currently available yield producer clones of sufficient titer to transduce human cells for gene therapy applications and have led to the initiation of human clinical trials. However, there are two areas in which these lines are deficient.

First, design of the appropriate retroviral vectors for particular applications requires the construction and testing of several vector configurations. For example, Belmont et al., Molec. and Cell. Biol. 8(12):5116-5125 (1988), constructed stable producer lines from 16 retroviral vectors in order to identify the vector capable of producing both the highest titer producer and giving optimal expression. Some of the configurations examined included: (1) LTR driven expression vs. an internal promoter; (2) selection of an internal promoter derived from a viral or a cellular gene; and (3) whether a selectable marker was incorporated in the construct. A packaging system that would enable rapid, high-titer virus production without the need to generate stable producer lines would be highly advantageous in that it would save approximately two months required for the identification of high titer producer clones derived from several constructs.

Second, compared to NIH 3T3 cells, the infection efficiency of primary cultures of mammalian somatic cells with a high titer amphotropic retrovirus producer varies considerably. The transduction efficiency of mouse myoblasts (Dhawan et al., Science 254:1509-1512(1991) or rat capillary endothelial cells (Yao et. al., Proc. Natl. Acad. Sci. USA 88:8101-8105 (1991)) was shown to be approximately equal to that of NIH 3T3 cells, whereas the transduction efficiency of canine hepatocytes (Armentano et. al., Proc. Natl. Acad. Sci. USA 87:6141-6145 (1990)) was only 25% of that found in NIH 3T3 cells. Primary human tumor-infiltrating lymphocytes ("TILs"), human CD4+ and CD8+ T cells isolated from peripheral blood lymphocytes, and primate long-term reconstituting hematopoietic stem cells, represent an extreme example of low transduction efficiency compared to NIH 3T3 cells. Purified human CD4+ and CD8+ T Cells have been reported on one occasion to be infected to levels of 6%-9% with supernatants from stable producer clones (Morecki et al., Cancer Immunol. Immunother. 32:342-352 (1991)). If the retrovirus vector contains the neoR gene, populations that are highly enriched for transduced cells can be obtained by selection in G418. However, selectable marker expression has been shown to have deleterious effects on long-term gene expression in vivo in hematopoietic stem cells (Apperly et.al. Blood 78:310-317(1991)).

To overcome these limitations, methods and compositions for novel transient transfection packaging systems are provided. Improvements in the retroviral vector design enables the following: (1) the replacement of cumbersome plasmid cloning and fusion procedures which represent the prior art, (2) the provision of a single straightforward plasmid construct which avoids undue fusions and mutations in the parent constructs, which would compromise the reagent in terms of gaining regulatory (i.e. FDA) approval, (3) the elimination of redundant, inoperative, and/or undesirable sequences in the resultant retroviral vector (4) greater flexibility in the selection and directional cloning of therapeutic gene constructs into the retroviral vector, (5) facilitation of the molecular cloning of various auxiliary domains within the retroviral vector, (6) the introduction of strategic modifications which demonstrably increase the performance of the parent plasmid in the context of vector producer cells, and thus, increasing the resulting potency of the retroviral vector product (7) significant reduction in the over-all size of the retroviral vector construct to the extent that plasmid production is increased from a "low copy, low yield" reagent in biologic fermentations to one of intermediate yield. Taken together, these modifications retain the virtues (in terms of vector safety, gene incorporation and gene expression) of retroviral vectors currently in use, while providing significant improvements in the construction, validation, manufacture, and performance of prospective retroviral vectors for human gene therapy. This represents the second component of TDS includes a high performance retroviral expression vector, designated the C-REX vector.

Transient transfection has numerous advantages over the packaging cell method. In this regard, transient transfection avoids the longer time required to generate stable vector-producing cell lines and is used if the vector genome or retroviral packaging components are toxic to cells. If the vector genome encodes toxic genes or genes that interfere with the replication of the host cell, such as inhibitors of the cell cycle or genes that induce apoptosis, it may be difficult to generate stable vector-producing cell lines, but transient transfection can be used to produce the vector before the cells die. Also, cell lines have been developed using transient infection that produce vector titre levels that are comparable to the levels obtained from stable vector-producing cell lines (Pear et al 1993, PNAS 90:8392-8396).

A high efficiency manufacturing process for large scale production of retroviral vector stock bearing cytocidal gene constructs with high bulk titer and biologic activity is provided. The manufacturing process describes the use of transiently transfected 293T producer cells; an engineered method of producer cell scale up; and a transient transfection procedure that generates retroviral vectors that retains cytocidal gene expression with high fidelity.

In another embodiment, a fully validated 293T (human embryonic kidney cells transformed with SV40 large T) master cell bank for clinical retroviral vector production is provided. Although 293T cells have generated small amounts of moderate to high titer vector stocks for laboratory use, these producer cells have not been shown previously to be useful for large scale production of clinical vector stocks. The U.S. FDA severely regulates and restricts the use of vectors that could transfer intact oncogenes in the clinical product. The manufacturing process incorporates a method of DNA degradation in the final steps of vector harvest and collection that does not result in any loss of vector potency. In another embodiment, a method for concentrating retroviral vector stocks for consistent generation of clinical vector products approaching $10^9$ cfu/ml is provided. The final formulation of the clinical product consisting of a chemically defined serum-free solution for harvest, collection and storage of high titer clinical vector stocks.

Figure 19A:
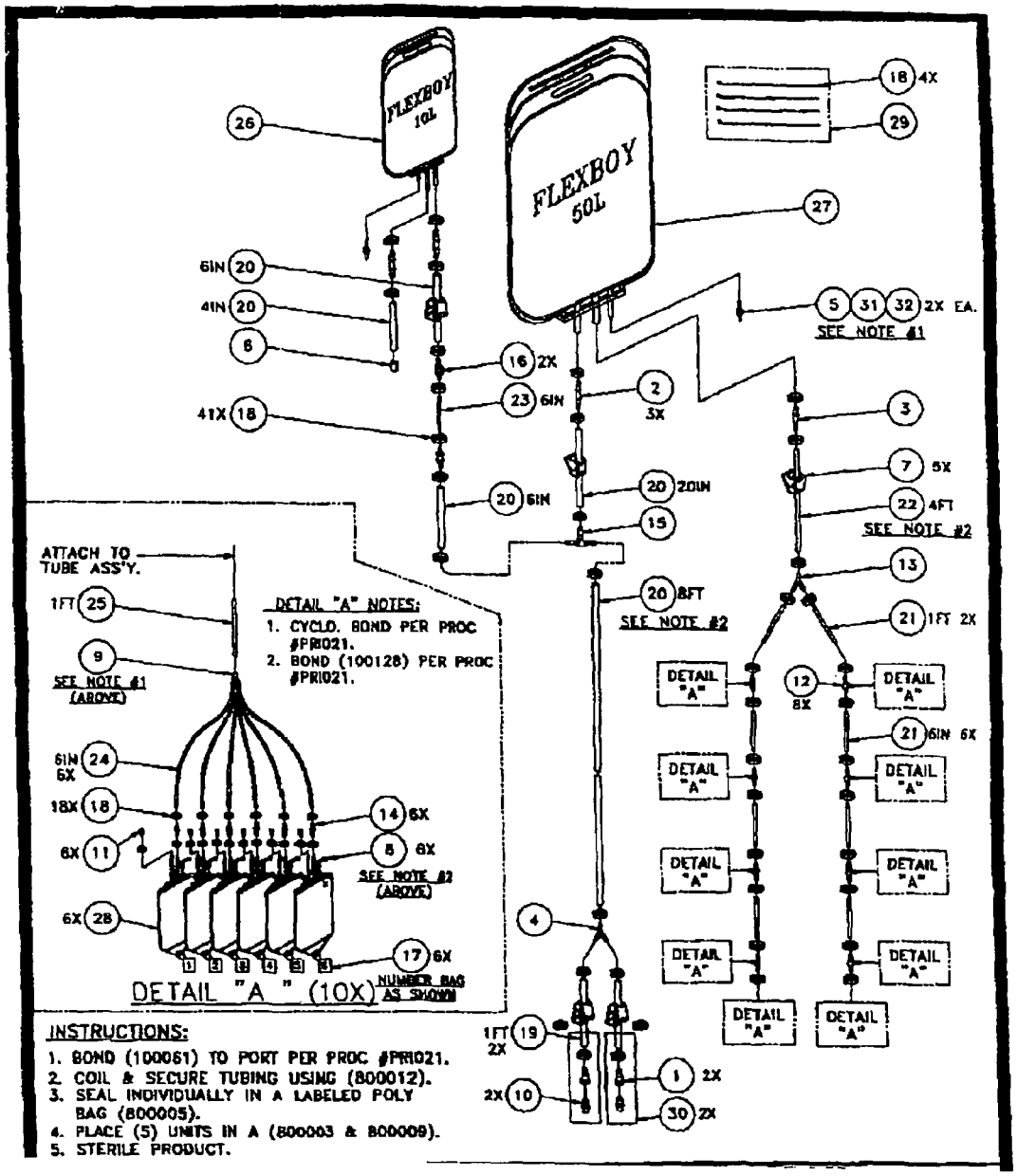
FIG. 19A depicts a closed-loop manifold system for producing targeted vectors.

In another embodiment, a method of collection of the clinical vector using a closed loop manifold system for maintenance of sterility, sampling of quality control specimens and facilitation of final fill, is provided. The closed-loop manifold assembly (see FIGS. 19A and 19B) is designed to meet the specifications required for collection of clinical product, i.e., maintenance of sterility during sampling, harvest, concentration and final fill, and is not available as a product for sale. The closed loop manifold assembly for harvest, concentration and storage of viral particles disclosed herein comprises a flexboy bag and manifold system made of Stedim 71 film; a 3 layer coextruded film consisting of a fluid contact layer of Ethyl Vinyl Acetate (EVA), a gas barrier of Ethyl Vinyl Alcohol (EVOH) and an outer layer of EVA. The total film thickness is 300 mm. EVA is an inert non-PVC-based film, which does not require the addition of plasticizers, thereby keeping extractables to a minimum. Stem has conducted extensive biocompatibility trials and has established a Drug Master File with the FDA for this product. The film and port tubes meet USP Class VI requirements. All bag customization takes place in Stedim's class 10,000-controlled manufacturing environment. The film, tubing and all components used are gamma compatible to 45 kGy. Gamma irradiation is performed at a minimum exposure of 25 kGy to a maximum of 45 kGy. Product certificates of conformance are provided from both Stedim and their contract sterilizers.

The clinical vector was stored in volumes of 150 ml in 500 ml cryobags at −80° C. The fully validated product exhibits a viral titer of $3\times10^7$ colony forming units (Units) per milliliter, a biologic potency of 65-70% growth inhibitory activity in human breast, colon and pancreatic cancer cells, a uniform particle size of ~100 nm with no viral aggregation, less than 550 bp residual DNA indicating absence of intact oncogenes, no detectable E1A or SV40 large T antigen, and no detectable replication competent retrovirus (RCR) in 5 passages on mus Dunni and human 293 cells. The product is sterile with an endotoxin level of <0.3 EU/ml, and the end of production cells are free of mycoplasma and other adventitious viruses.

The viral envelope includes a targeting ligand which include, but are not limited to, the arginine-glycine-aspartic acid, or RGD, sequence, which binds fibronectin, and a polypeptide having the sequence Gly-Gly-Trp-Ser-His-Trp (SEQ ID NO: 5), which also binds to fibronectin. In addition to the binding region, the targeting polypeptide may further include linker sequences of one or more amino acid residues, placed at the N-terminal and/or C-terminal of the binding region, whereby such linkers increase rotational flexibility and/or minimize steric hindrance of the modified envelope polypeptide. The polynucleotides may be constructed by genetic engineering techniques known to those skilled in the art.

Thus, a targeted delivery vector made in accordance with this invention contains associated therewith a ligand that facilitates the vector accumulation at a target site, i.e. a target-specific ligand. The ligand is a chemical moiety, such as a molecule, a functional group, or fragment thereof, which is specifically reactive with the target of choice while being less reactive with other targets thus giving the targeted delivery vector an advantage of transferring nucleic acids encoding therapeutic or diagnostic polypeptides, selectively into the cells in proximity to the target of choice. By being "reactive" it is meant having binding affinity to a cell or tissue, or being capable of internalizing into a cell wherein binding affinity is detectable by any means known in the art, for example, by any standard in vitro assay such as ELISA, flow cytometry, immunocytochemistry, surface plasmon resonance, etc. Usually a ligand binds to a particular molecular moiety—an epitope, such as a molecule, a functional group, or a molecular complex associated with a cell or tissue, forming a binding pair of two members. It is recognized that in a binding pair, any member may be a ligand, while the other being an epitope. Such binding pairs are known in the art. Exemplary binding pairs are antibody-antigen, hormone-receptor, enzyme-substrate, nutrient (e.g. vitamin)-transport protein, growth factor-growth factor receptor, carbohydrate-lectin, and two polynucleotides having complementary sequences. Fragments of the ligands are to be considered a ligand and may be used for the present invention so long as the fragment retains the ability to bind to the appropriate cell surface epitope. Preferably, the ligands are proteins and peptides comprising antigen-binding sequences of an immunoglobulin. More preferably, the ligands are antigen-binding antibody fragments lacking Fc sequences. Such preferred ligands are Fab fragments of an immunoglobulin, $F(ab)_2$ fragments of immunoglobulin, Fv antibody fragments, or single-chain Fv antibody fragments. These fragments can be enzymatically derived or produced recombinantly. In their functional aspect, the ligands are preferably internalizable ligands, i.e. the ligands that are internalized by the cell of choice for example, by the process of endocytosis. Likewise, ligands with substitutions or other alterations, but which retain the epitope binding ability, may be used. The ligands are advantageously selected to recognize pathological cells, for example, malignant cells or infectious agents. Ligands that bind to exposed collagen, for example, can target the vector to an area of a subject that comprises malignant tissue. In general, cells that have metastasized to another area of a body do so by invading and disrupting healthy tissue. This invasion results in exposed collagen which can be targeted by the vectors provided herein.

An additional group of ligands that can be used to target a vector are those that form a binding pair with the tyrosine kinase growth factor receptors which are overexpressed on the cell surfaces in many tumors. Exemplary tyrosine kinase growth factors are VEGF receptor, FGF receptor, PDGF receptor, IGF receptor, EGF receptor, TGF-alpha receptor, TGF-beta receptor, HB-EGF receptor, ErbB2 receptor, ErbB3 receptor, and ErbB4 receptor. EGF receptor vIII and ErbB2 (HEr2) receptors are especially preferred in the context of cancer treatment using INSERTS as these receptors are more specific to malignant cells, while scarce on normal ones. Alternatively, the ligands are selected to recognize the cells in need of genetic correction, or genetic alteration by introduction of a beneficial gene, such as: liver cells, epithelial cells, endocrine cells in genetically deficient organisms, in vitro embryonic cells, germ cells, stem cells, reproductive cells, hybrid cells, plant cells, or any cells used in an industrial process.

The ligand may be expressed on the surface of a viral particle or attached to a non-viral particle by any suitable method available in the art. The attachment may be covalent or non-covalent, such as by adsorption or complex formation. The attachment preferably involves a lipophilic molecular moiety capable of conjugating to the ligand by forming a covalent or non-covalent bond, and referred to as an "anchor". An anchor has affinity to lipophilic environments such as lipid micelles, bilayers, and other condensed phases, and thereby attaches the ligand to a lipid-nucleic acid microparticle. Methods of the ligand attachment via a lipophilic anchor are known in the art. (see, for example, F. Schuber, "Chemistry of ligand-coupling to liposomes", in: Liposomes as Tools for Basic Research and Industry, ed. by J. R. Philippot and F. Schuber, CRC Press, Boca Raton, 1995, p.21-37).

It is recognized that the targeted delivery vectors disclosed herein include viral and non-viral particles. Non-viral particles include encapsulated nucleoproteins, including wholly or partially assembled viral particles, in lipid bilayers. Methods for encapsulating viruses into lipid bilayers are known in the art. They include passive entrapment into lipid bilayer-enclosed vesicles (liposomes), and incubation of virions with liposomes (U.S. Pat. No. 5,962,429; Fasbender, et al., J. Biol. Chem. 272:6479-6489; Hodgson and Solaiman, Nature Biotechnology 14:339-342 (1996)). Without being limited by a theory, we assume that acidic proteins exposed on the surface of a virion provide an interface for complexation with the cationic lipid/cationic polymer component of the targeted delivery vector and serve as a "scaffold" for the bilayer formation by the neutral lipid component. Exemplary types of viruses are adenoviruses, retroviruses, herpesviruses, lentiviruses, and bacteriophages.

Non-viral delivery systems, such as microparticles or nanoparticles including, for example, cationic liposomes and polycations, provide alternative methods for delivery systems and are encompassed by the present disclosure.

Examples of non-viral delivery systems include, for example, Wheeler et al., U.S. Pat. Nos. 5,976,567 and 5,981,501. These patents disclose preparation of serum-stable plasmid-lipid particles by contacting an aqueous solution of a plasmid with an organic solution containing cationic and non-cationic lipids. Thierry et al., U.S. Pat. No. 6,096,335 disclose preparing of a complex comprising a globally anionic biologically active substance, a cationic constituent, and an anionic constituent. Allen and Stuart, PCT/US98/12937 (WO 98/58630) disclose forming polynucleotide-cationic lipid particles in a lipid solvent suitable for solubilization of the cationic lipid, adding neutral vesicle-forming lipid to the solvent containing the particles, and evaporating the lipid solvent to form liposomes having the polynucleotide entrapped within. Allen and Stuart, U.S. Pat. No. 6,120,798, disclose forming polynucleotide-lipid microparticles by dissolving a polynucleotide in a first, e.g. aqueous, solvent, dissolving a lipid in a second, e.g. organic, solvent immiscible with said first solvent, adding a third solvent to effect formation of a single phase, and further adding an amount of the first and second solvents to effect formation of two liquid phases. Bally et al. U.S. Pat. No. 5,705,385, and Zhang et al. U.S. Pat. No. 6,110,745 disclose a method for preparing a lipid-nucleic acid particle by contacting a nucleic acid with a solution containing a non-cationic lipid and a cationic lipid to form a lipid-nucleic acid mixture. Maurer et al., PCT/CA00/00843 (WO 01/06574) disclose a method for preparing fully lipid-encapsulated therapeutic agent particles of a charged therapeutic agent including combining preformed lipid vesicles, a charged therapeutic agent, and a destabilizing agent to form a mixture thereof in a destabilizing solvent that destabilizes, but does not disrupt, the vesicles, and subsequently removing the destabilizing agent.

A Particle-Forming Component ("PFC") typically comprises a lipid, such as a cationic lipid, optionally in combination with a PFC other than a cationic lipid. A cationic lipid is a lipid whose molecule is capable of electrolytic dissociation producing net positive ionic charge in the range of pH from about 3 to about 10, preferably in the physiological pH range from about 4 to about 9. Such cationic lipids encompass, for example, cationic detergents such as cationic amphiphiles having a single hydrocarbon chain. Patent and scientific literature describes numerous cationic lipids having nucleic acid transfection-enhancing properties. These transfection-enhancing cationic lipids include, for example: 1,2-dioleyloxy-3-(N,N,N-trimethylammonio)propane chloride-, DOTMA (U.S. Pat. No. 4,897,355); DOSPA (see Hawley-Nelson, et al., Focus 15(3):73 (1993)); N,N-distearyl-N,N-dimethyl-ammonium bromide, or DDAB (U.S. Pat. No. 5,279,833); 1,2-dioleoyloxy-3-(N,N,N-trimethylammonio) propane chloride-DOTAP (Stamatatos, et al., Biochemistry 27: 3917-3925 (1988)); glycerol based lipids (see Leventis, et al., Biochem. Biophys. Acta 1023:124 (1990); arginyl-PE (U.S. Pat. No. 5,980,935); lysinyl-PE (Puyal, et al. J. Biochem. 228:697 (1995)), lipopolyamines (U.S. Pat. No. 5,171,678) and cholesterol based lipids (WO 93/05162, U.S. Pat. No. 5,283,185); CHIM (1-(3-cholesteryl)-oxycarbonyl-aminomethylimidazole); and the like. Cationic lipids for transfection are reviewed, for example, in: Behr, Bioconjugate Chemistry, 5:382-389 (1994). Preferable cationic lipids are DDAB, CHIM, or combinations thereof. Examples of cationic lipids that are cationic detergents include (C12-C18)-alkyl- and (C12-C18)-alkenyl-trimethylammonium salts, N—(C12-C18)-alkyl- and N—(C12-C18)-alkenyl-pyridinium salts, and the like.

The size of a targeted delivery vector formed in accordance with this invention is within the range of about 40 to about 1500 nm, preferably in the range of about 50-500 nm, and most preferably, in the range of about 20-150 nm. This size selection advantageously aids the targeted delivery vector, when it is administered to the body, to penetrate from the blood vessels into the diseased tissues such as malignant tumors, and transfer a therapeutic nucleic acid therein. It is also a characteristic and advantageous property of the targeted delivery vector that its size, as measured for example, by dynamic light scattering method, does not substantially increase in the presence of extracellular biological fluids such as in vitro cell culture media or blood plasma.

Alternatively, as described in Culver et al (1992) Science 256, 1550-1552, cells which produce retroviruses can be injected into a tumor. The retrovirus-producing cells so introduced are engineered to actively produce a targeted delivery vector, such as a viral vector particle, so that continuous productions of the vector occurred within the tumor mass in situ. Thus, proliferating tumor cells can be successfully transduced in vivo if mixed with retroviral vector-producing cells.

Methods of Treatment

The targeted vectors of the present invention can also be used as a part of a gene therapy protocol to deliver nucleic acids encoding a therapeutic agent, such a mutant cyclin-G polypeptide. Thus, another aspect of the invention features expression vectors for in vivo or in vitro transfection of a therapeutic agent to areas of a subject comprising cell types associated with metastasized neoplastic disorders. The targeted vectors provided herein are intended for use as vectors for gene therapy. The mutant cyclin-G polypeptide and nucleic acid molecules can be used to replace the corresponding gene in other targeted vectors. Alternatively, a targeted vector disclosed herein (e.g., one comprising a collagen binding domain) can contain nucleic acid encoding any therapeutically agent (e.g., thymidine kinase). Of interest are those therapeutic agents useful for treating neoplastic disorders.

The present studies provide data generated from in vivo human clinical trials. Nevertheless, additional toxicity and therapeutic efficacy of a targeted vectors disclosed herein can be determined by standard pharmaceutical procedures in cell cultures or experimental animals, e.g., for determining the $LDS_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Doses that exhibit large therapeutic indices are preferred. In the present invention, doses that would normally exhibit toxic side effects may be used because the delivery system is designed to target the site of treatment in order to minimize damage to untreated cells and reduce side effects.

The data obtained from human clinical trials (see below) prove that the targeted vector of the invention functions in vivo to inhibit the progression of a neoplastic disorder. The data in Table 1 provides a treatment regimen for administration of such a vector to a patient. In addition, data obtained from cell culture assays and animal studies using alternative forms of the targeted vector (e.g., alternative targeting mechanism or alternative therapeutic agent) can be used in formulating a range of dosage for use in humans. The dosage lies preferably within a range of circulating concentrations that include the $ED_{50}$ with little or no toxicity. The dosage may vary within this range depending upon the dosage form employed and the route of administration utilized. A therapeutically effective dose can be estimated initially from cell culture assays. A dose may be formulated in animal models to achieve a circulating plasma concentration range that includes the $IC_{50}$ (ie., the concentration of the test compound which achieves a half-maximal infection or a half-maximal inhibition) as determined in cell culture. Such information can be used to more accurately determine useful doses in humans. Levels in plasma may be measured, for example, by high performance liquid chromatography.

Pharmaceutical compositions containing a targeted delivery vector can be formulated in any conventional manner by mixing an a selected amount of the vector with one or more physiologically acceptable carriers or excipients. For example, the targeted delivery vector may be suspended in a carrier such as PBS (phosphate buffered saline). The active compounds can be administered by any appropriate route, for example, orally, parenterally, intravenously, intradermally, subcutaneously, or topically, in liquid, semi-liquid or solid form and are formulated in a manner suitable for each route of administration. Preferred modes of administration include oral and parenteral modes of administration.

The targeted delivery vector and physiologically acceptable salts and solvates may be formulated for administration by inhalation or insufflation (either through the mouth or the nose) or for oral, buccal, parenteral or rectal administration. For administration by inhalation, the targeted delivery vector can be delivered in the form of an aerosol spray presentation from pressurized packs or a nebulizer, with the use of a suitable propellant, e.g. dichlorodifluoromethane, trichlorofluoromethane, dichlorotetra-fluoroetha-ne, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of a therapeutic compound and a suitable powder base such as lactose or starch.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g. magnesium stearate, talc or silica); disintegrants (e.g. potato starch or sodium starch glycolate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner.

The targeted delivery vector may be formulated for parenteral administration by injection e.g. by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder lyophilized form for constitution with a suitable vehicle, e.g., sterile pyrogen-free water, before use.

In addition to the formulations described previously, the targeted delivery vector may also be formulated as a depot preparation. Such long acting formulations may be administered by implantation (for example, subcutaneously or intramuscularly) or by intramuscular injection. Thus, for example, the therapeutic compounds may be formulated with suitable polymeric or hydrophobic materials (for example as an emulsion in an acceptable oil) or ion exchange resins, or as sparingly soluble derivatives, for example, as a sparingly soluble salt.

The active agents may be formulated for local or topical application, such as for topical application to the skin and mucous membranes, such as in the eye, in the form of gels, creams, and lotions and for application to the eye or for intracisternal or intraspinal application. Such solutions, particularly those intended for ophthalmic use, may be formulated as 0.01%-10% isotonic solutions, pH about 5-7, with appropriate salts. The compounds may be formulated as aerosols for topical application, such as by inhalation.

The concentration of active compound in the drug composition will depend on absorption, inactivation and excretion rates of the active compound, the dosage schedule, and amount administered as well as other factors known to those of skill in the art. For example, the amount that is delivered is sufficient to treat the symptoms of hypertension.

The compositions may, if desired, be presented in a pack or dispenser device which may contain one or more unit dosage forms containing the active ingredient. The pack may for example, comprise metal or plastic foil, such as a blister pack. The pack or dispenser device may be accompanied by instructions for administration.

The active agents may be packaged as articles of manufacture containing packaging material, an agent provided herein, and a label that indicates the disorder for which the agent is provided.

The targeted retroviral particle comprising the cytokine gene may be administered alone or in conjunction with other therapeutic treatments or active agents. For example, the targeted retroviral particle comprising a cytokine gene may be administered with the targeted retroviral particle comprising a cytocidal gene. The quantity of the targeted retroviral particle comprising a cytocidal gene to be administered is based on the titer of the virus particles as described herein above. By way of example, if the targeted retroviral particle comprising a cytokine gene is administered in conjunction with a targeted retroviral particle comprising a cytocidal gene the titer of the retroviral particle for each vector may be lower than if each vector is used alone. The targeted retroviral particle comprising the cytokine gene may be administered concurrently or separately from the targeted retroviral particle comprising the cytocidal gene.

The methods of the subject invention also relate to methods of treating cancer by administering a targeted retroviral particle (e.g., the targeted retroviral vector expressing a cytokine either alone or in conjunction with the targeted retroviral vector expressing a cytocidal gene) with one or more other active agents. Examples of other active agents that may be used include, but are not limited to, chemotherapeutic agents, anti-inflammatory agents, protease inhibitors, such as HIV protease inhibitors, nucleoside analogs, such as AZT. The one or more active agents may be administered concurrently or separately (e.g., before administration of the targeted retroviral particle or after administration of the targeted retroviral particle) with the one or more active agents. One of skill in the art will appreciate that the targeted retroviral particle may be administered either by the same route as the one or more agents (e.g., the targeted retroviral vector and the agent are both administered intravenously) or by different routes (e.g., the targeted retroviral vector is administered intravenously and the one or more agents are administered orally).

An effective amount or therapeutically effective of the targeted retroviral particles to be administered to a subject in need of treatment may be determined in a variety of ways. By way of example, the amount may be based on viral titer or efficacy in an animal model. Alternatively the dosing regimes used in clinical trials may be used as general guidelines. The daily dose may be administered in a single dose or in portions at various hours of the day. Initially, a higher dosage may be required and may be reduced over time when the optimal initial response is obtained. By way of example, treatment may be continuous for days, weeks, or years, or may be at intervals with intervening rest periods. The dosage may be modified in accordance with other treatments the individual may be receiving. However, the method of treatment is in no way limited to a particular concentration or range of the targeted retroviral particle and may be varied for each individual being treated and for each derivative used.

One of skill in the art will appreciate that individualization of dosage may be required to achieve the maximum effect for a given individual. It is further understood by one skilled in the art that the dosage administered to a individual being treated may vary depending on the individuals age, severity or stage of the disease and response to the course of treatment. One skilled in the art will know the clinical parameters to evaluate to determine proper dosage for the individual being treated by the methods described herein. Clinical parameters that may be assessed for determining dosage include, but are not limited to, tumor size, alteration in the level of tumor markers used in clinical testing for particular malignancies. Based on such parameters the treating physician will determine the therapeutically effective amount to be used for a given individual. Such therapies may be administered as often as necessary and for the period of time judged necessary by the treating physician.

In the present studies, exemplary protocols were designed for cancer patients. An intra-patient dose escalation regimen by intravenous infusion of Rexin-G was given daily for 8-10 days. Completion of this regimen was followed by a one-week rest period for assessment of toxicity; after which, the maximum tolerated dose of Rexin-G was administered IV for another 8-10 days. If the patient did not develop a grade 3 or 4 adverse event related to Rexin-G during the treatment periods, the dose of Rexin-G was escalated as follows:

TABLE 1

Treatment Regimen

| Treatment Day | Dose Level | Vector Dose/Day |
|---|---|---|
| Day 1-6 (Dose Escalation Regimen) | I | $4.5 \times 10^9$ Units |
| Day 7-8 | II | $9.0 \times 10^9$ Units |
| Day 9-10 | III | $1.4 \times 10^{10}$ Units |
| Day 18-27 (High Dose Regimen) | III | $1.4 \times 10^{10}$ Units |

Based on the observed safety in the first two patients, a third patient with Stage IVB pancreatic cancer with numerous liver metastases was given a frontline treatment with intravenous Rexin-G for six days, followed by 8 weekly doses of gemcitabine at 1000 mg/m² in a second clinical protocol approved by the Philippine BFAD.

Kits

Also provided are kits or drug delivery systems comprising the compositions for use in the methods described herein. All the essential materials and reagents required for administration of the targeted retroviral particle may be assembled in a kit (e.g., packaging cell construct or cell line, cytokine expression vector). The components of the kit may be provided in a variety of formulations as described above. The one or more targeted retroviral particle may be formulated with one or more agents (e.g., a chemotherapeutic agent) into a single pharmaceutically acceptable composition or separate pharmaceutically acceptable compositions.

The components of these kits or drug delivery systems may also be provided in dried or lyophilized forms. When reagents or components are provided as a dried form, reconstitution generally is by the addition of a suitable solvent, which may also be provided in another container means. The kits of the invention may also comprise instructions regarding the dosage and or administration information for the targeted retroviral particle. The kits or drug delivery systems of the present invention also will typically include a means for containing the vials in close confinement for commercial sale such as, e.g., injection or blow-molded plastic containers into which the desired vials are retained. Irrespective of the number or type of containers, the kits may also comprise, or be packaged with, an instrument for assisting with the injection/administration or placement of the ultimate complex composition within the body of a subject. Such an instrument may be an applicator, inhalant, syringe, pipette, forceps, measured spoon, eye dropper or any such medically approved delivery vehicle.

In another embodiment, a method for conducting a gene therapy business is provided. The method includes generating targeted delivery vectors and establishing a bank of vectors by harvesting and suspending the vector particles in a solution of suitable medium and storing the suspension. The method further includes providing the particles, and instructions for use of the particles, to a physician or health care provider for administration to a subject (patient) in need thereof. Such instructions for use of the vector can include the exemplary treatment regimen provided in Table 1. The method optionally includes billing the patient or the patient's insurance provider.

In yet another embodiment, a method for conducting a gene therapy business, including providing kits disclosed herein to a physician or health care provider, is provided The following examples are included for illustrative purposes only and are not intended to limit the scope of the invention. The specific methods exemplified can be practiced with other species. The examples are intended to exemplify generic processes.

EXAMPLES

Pancreatic cancer is the fourth leading cause of cancer death in the United States, and is the deadliest of all cancers. Complete surgical resection of the pancreatic tumor offers the only effective treatment for this disease. Unfortunately, such "curative" operations are only possible in 10 to 15% of patients with pancreatic cancer, typically those individuals in whom jaundice is the presenting symptom. The median survival time for patients with non-resectable pancreatic cancer is 3-6 months. Hence, the management of advanced pancreatic cancer is generally directed at palliation of symptoms. External beam radiation does not appear to prolong survival, although sufficient reduction in tumor size may lead to alleviation of pain. The addition of chemotherapy with fluorouracil (5-FU) to external beam radiation has increased the survival time for these patients (18). Recently, gemcitabine, a deoxycytidine analogue, has been shown to improve the quality of life of patients with advanced pancreatic cancer, although the duration of survival is extended by only 8-10 weeks.

Example 1

Constructs

The plasmid pBv1/CAEP contains coding sequences of the 4070A amphotropic envelope protein (GenBank accession number: M33469), that have been modified to incorporate an integral gain of collagen-binding function (Hall et al., Human Gene Therapy, 8:2183-2192, 1997). The parent expression plasmid, pCAE (Morgan et al., Journal of Virology, 67:4712-4721 ,1967) was provided by the USC Gene Therapy Laboratories. This pCAE plasmid was modified by insertion of a Pst I site (gct gca gga, encoding the amino acids AAG) near the N-terminus of the mature protein between the coding sequences of amino acids 6 and 7 (pCAEP). A synthetic oligonucleotide duplex (gga cat gta gga tgg aga gaa cca tca ttc atg gct ctg tca gct gca (SEQ ID NO: 6), encoding the amino acids GHVGWREPSFMALSAA (SEQ ID NO: 7), a minimal collagen-binding decapeptide (in bold) derived from the D2 domain of bovine von Willebrand Factor (Hall et al., Human Gene Therapy, 11:983-993, 2000) and flanked by strategic linkers (underlined), was cloned into this unique Pst I site to produce pBv1/CAEP.

The expression of the chimeric envelope protein in 293T producer cells is driven by the strong CMV i.e. promoter. The chimeric envelope is processed correctly and incorporated stably into retroviral particles, which exhibit the gain-of-function phenotype without appreciable loss of infectious titer. Correct orientation of the collagen-binding domain was confirmed by DNA sequence analysis, and plasmid quality control was confirmed by restriction digestion Pst I, which linearizes the plasmid and releases the collagen-binding domain.

The plasmid pCgpn contains the MoMuLV gag-pol coding sequences (GenBank Accession number 331934), initially derived from proviral clone 3PO as pGag-pol-gpt, (Markowitz et al., Journal of Virology, 62:1120-1124, 1988) exhibiting a 134-base-pair deletion of the T packaging signal and a truncation of env coding sequences. The construct was provided as an EcoRI fragment in pCgp in which the 5' EcoRI site corresponds to the XmaIII site upstream of Gag and the 3' EcoRI site was added adjacent to the ScaI site in env. The EcoRi fragment was excised from pCgp and ligated into the pcDNA3.1+ expression vector (Invitrogen) at the unique EcoRI cloning site.

Correct orientation was confirmed by restriction digestion with SalI and the insert was further characterized by digestion with EcoRI and HindIII. Both the 5' and 3'sequences of the gag-pol insert were confirmed by DNA squences analysis utilzing the T7 promoter binding site primer (S1) and the pcDNA3.1/BGH reverse priming site (AS1), respectively. The resulting plasmid, designated pCgpn, encodes the gag-pol polyprotein driven by the strong CMV promoter and a neomycin resistance gene driven by the SV40 early promoter. The presence of an SV40 ori in this plasmid enables episomal replication in cell lines that express the SV40 large T antigen (i.e., 293T producer cells).

The following describes the construction of the plasmid bearing the pdnG1/C-REX retroviral expression vector which contains the dominant negative cyclin G1 construct (dnG1). The plasmid is enhanced for production of vectors of high infectious titer by transient transfection protocols. The cDNA sequences (472-1098 plus stop codon) encoding aa 41 to 249 of human cyclin G1 (CYCG1 Wu et al., Oncology Reports, 1:705-11, 1994; accession number U47413) were generated from a full length cyclin G1 template by PCR, incorporating Not I/Sal I overhangs. The N-terminal deletion mutant construct was cloned initially into a TA cloning vector (Invitrogen), followed by Not I/Sal I digestion and ligation of the purified insert into a Not I/Sal I digested pG1XSvNa retroviral expression vector (Genetic Therapy, Inc.) to produce the pdnG1SvNa vector complete with 5' and 3' long terminal repeat (LTR) sequences and a Ψ retroviral packaging sequence.

A CMV i.e. promoter-enhancer was prepared by PCR from a CMV-driven pIRES template (Clontech), incorporating Sac II overhangs, and cloned into the unique Sac II site of pdnG1SvNa upstream of the 5' LTR. The neomycin resistance gene, which facilitates determination of vector titer, is driven by the Sv40 e.p. with its nested ori. The inclusion of the strong CMV promoter, in addition to the Sv40 ori, facilitate high titer retroviral vector production in 293T cells expressing the large T antigen (Soneoka et al., Nucleic Acid Research, 23:628-633, 1995). Correct orientation and sequence of the CMV promoter was confirmed by restriction digestion and DNA sequence analysis, as was the dnG1 coding sequences. Plasmid identity and quality control is confirmed by digestion with Sac II (which releases the 750 bp CMV promoter) and Bgl II (which cuts at a unique site within the dnG1 construct).

Example 2

REXIN-G

The final product, Mx-dnG1 (REXIN-G™), is a matrix (collagen)-targeted retroviral vector encoding a N-terminal deletion mutant human cyclin G1 construct under the control of a hybrid LTR/CMV promoter. The vector also contains the neomycin resistance gene which is driven by the SV40 early promoter.

The Mx-dnG1 vector is produced by transient co-transfection with 3 plasmids of 293T (human embryonic kidney 293 cells transformed with SV40 large T antigen) cells obtained from a fully validated master cell bank.

The components of the transfection system includes the pdnG1/C-REX therapeutic plasmid construct which contains the deletion mutant of the human cyclin G1 gene encoding a.a. 41 to 249 driven by the CMV immediate early promoter, packaging sequences, and the bacterial neomycin resistance gene under the control of an internal SV40 early promoter. The truncated cyclin G1 gene was initially cloned into a TA cloning vector (Invitrogen), followed by Not I/Sal I digestion and ligation of the purified insert into a Not I/Sal I digested pG1XSvNa retroviral expression vector (provided by Genetic Therapy, Inc., Gaithersburg, Md.) to produce the pdnG1SvNa vector complete with 5' and 3' LTR sequences and a Ψ sequence. The CMV i.e. promoter-enhancer was prepared by PCR from a CMV-driven pIRES template (Clontech), incorporating Sac II overhangs, and cloned into the unique SacII site of pdnG1SvNa upstream of the 5'LTR.

The system further includes the Mx (Bv1/pCAEP) envelope plasmid containing a CMV-driven modified amphotropic 4070A envelope protein wherein a collagen-binding peptide was inserted into an engineered Pst I site between a.a. 6 and 7 of the N terminal region of the 4070A envelope.

The system also includes the pCgpn plasmid which contains the MLV gag-pol elements driven by the CMV immediate early promoter. It is derived from clone 3PO as pGag-pol-gpt. The vector backbone is a pcDNA3.1+ from Invitrogen. Polyadnylation signal and transcription termination sequences from bovine growth hormone enhance RNA stability. An SV40 ori is featured along with the e.p. for episomal replication and vector rescue in cell lines expressing SV40 target T antigen.

The plasmids have been analyzed by restriction endonuclease digestion and the cell line consists of a DMEM base supplemented with 4 grams per liter glucose, 3 grams per liter sodium bicarbonate, and 10% gamma irradiated fetal bovine serum (Biowhittaker). The serum was obtained from USA sources, and has been tested free of bovine viruses in compliance with USDA regulations. The budding of the retroviral particles is enhanced by induction with sodium butyrate. The resulting viral particles are processed solely by passing the supernatant through a 0.45 micron filter or concentrated using a tangential flow/diafiltration method. The viral particles are Type C retrovirus in appearance. Retroviral particles will be harvested and suspended in a solution of 95% DMEM medium and 1.2% human serum albumin. This formulation is stored in aliquots of 150 ml in a 500 ml cryobag and kept frozen at −70 to −86° C. until used.

Preparation of the Mx-dnG1 vector for patient administration consists of thawing the vector in the vector bag in a 37° C. 80% ethanol bath. Each vector bag will be thawed one hour prior to infusion into the patient, treated with Pulmozyme (10 U/ml), and immediately infused within 1-3 hours.

Example 3

Therapeutic Efficacy of the Mx-dnG1 Vector

The efficacy of Mx-dnG1 in inhibiting cancer cell proliferation in vitro, and in arresting tumor growth in vivo in a nude mouse model of liver metastasis, was tested. A human undifferentiated cancer cell line of pancreatic origin was selected as the prototype of metastatic cancer. Retroviral transduction efficiency in these cancer cells was excellent, ranging from 26% to 85%, depending on the multiplicity of infection (4 and 250 respectively). For selection of a therapeutic gene, cell proliferation studies were conducted in transduced cells using vectors bearing various cyclin G1 constructs. Under standard conditions, the Mx-dnG1 vector consistently exhibited the greatest anti-proliferative effect, concomitant with the appearance of immunoreactive cyclin G1 at the region of 20 kDa, representing the dnG1 protein. Based on these results, the Mx-dnG1 vector was selected for subsequent in vivo efficacy studies.

To assess the performance of Mx-dnG1 in vivo, a nude mouse model of liver metastasis was established by infusion of $7 \times 10^5$ human pancreatic cancer cells into the portal vein via an indwelling catheter that was kept in place for 14 days. Vector infusions were started three days later, consisting of 200 ml/day of either Mx-dnG1 (REXIN-G™; titer: $9.5 \times 10^8$ cfu/ml) or PBS saline control for a total of 9 days. The mice were sacrificed one day after completion of the vector infusions.

Histologic and immunocytochemical evaluation of metastatic tumor foci from mice treated with either PBS or low dose Mx-dnG1 was performed and evaluated with an Optimas imaging system. The human cyclin G1 protein was highly expressed in metastatic tumor foci, as evidenced by enhanced cyclin G1 nuclear immunoreactivity (brown-staining material) in the PBS-treated animals, and in the residual tumor foci of Mx-dnG1 vector-treated animals. Histologic examination of liver sections from control animals revealed substantial tumor foci with attendant areas of angiogenesis and stroma formation; the epithelial components stained positive for cytokeratin and associated tumor stromal/endothelial cells stained positive for vimentin and FLK receptor. In contrast, the mean size of tumor foci in the low dose Mx-dnG1-treated animals was significantly reduced compared to PBS controls ($p=0.001$), simultaneously revealing a focal increase in the density of apoptotic nuclei compared to the PBS control group. Further, infiltration by PAS+, CD68+ and hemosiderin-laden macrophages was observed in the residual tumor foci of Mx-dnG1-treated animals, suggesting active clearance of degenerating tumor cells and tumor debris by the hepatic reticuloendothelial system. Taken together, these findings demonstrate the anti-tumor efficacy in vivo of a targeted injectable retroviral vector bearing a cytocidal cell cycle control gene, and represent a definitive advance in the development of targeted injectable vectors for metastatic cancer.

In a subcutaneous human pancreatic cancer model in nude mice, we demonstrated that intravenous (IV) infusion of Mx-dnG1 enhanced gene delivery and arrested growth of subcutaneous tumors when compared to the non-targeted CAE-dnG1 vector ($p=0.014$), a control matrix-targeted vector bearing a marker gene (Mx-nBg; $p=0.004$) and PBS control ($p=0.001$). Enhanced vector penetration and transduction of tumor nodules (35.7+S.D.1.4%) correlated with therapeutic efficacy without associated systemic toxicity. Kaplan-Meier survival studies were also conducted in mice treated with PBS placebo, the non-targeted CAE-dnG1 vector and Mx-dnG1 vector. Using the Tarone logrank test, the over-all p value for comparing all three groups simultaneously was 0.003, with a trend that was significant to a level of 0.004, indicating that the probability of long term control of tumor growth was significantly greater with targeted Mx-dnG1 vector than with the non-targeted CAE-dnG1 vector or PBS placebo. Taken together, the present study demonstrates that Mx-dnG1, deployed by peripheral vein injection (i) accumulated in angiogenic tumor vasculature within one hour, (ii) transduced tumor cells with high level efficiency, and (iii) enhanced therapeutic gene delivery and long term efficacy without eliciting appreciable toxicity.

Example 4

Pharmacology/Toxicology Studies

Matrix-targeted injectable retroviral vectors incorporating peptides that target extracellular matrix components (e.g. collagen) have been demonstrated to enhance therapeutic gene delivery in vivo. Additional data are presented using two mouse models of cancer and two matrix-targeted MLV-based retroviral vectors bearing a cytocidal/cytostatic dominant negative cyclin G1 construct (designated Mx-dnG1 and MxV-dnG1). Both Mx-dnG1 and MxV-dnG1 are amphotropic 4070A MLV-based retroviral vectors displaying a matrix (collagen)-targeting motif for targeting areas of pathology. The only difference between the two vectors is that MxV-dnG1 is pseudotyped with a vesicular stomatitis virus G protein.

In the subcutaneous human cancer xenograft model, $1 \times 10^7$ human MiaPaca2 pancreatic cancer cells (prototype for metastatic gastrointestinal cancer) were implanted subcutaneously into flank of nude mice. Six days later, 200 µl Mx-dnG1 vector was injected directly into the tail vein daily for one or two 10-day treatment cycles (Total vector dose: $5.6 \times 10^7$ [n=6] or $1.6 \times 10^8$ cfu [n=4] respectively). In the nude mouse model of liver metastasis, $7 \times 10^5$ MiaPaca2 cells were injected through the portal vein via an indwelling catheter which was kept in place for 10-14 days. 200 ml of MxV-dnG1 vector was infused over 10 min daily for 6 or 9 days (Total vector dose: $4.8 \times 10^6$ [n=3] or $1.1 \times 10^9$ cfu dose [n=4] respectively) starting three days after infusion of tumor cells. For biodistribution studies, a TaqManTM based assay was developed to detect the G1XSvNa-based vector containing SV40 and Neomycin (Neo) gene sequences into mouse genomic DNA background (Althea Technologies, San Diego, Calif., USA). The assay detects a 95 nt amplicon (nts. 1779-1874 of the G1XSvNa plasmid vector) in which the fluoresecently labeled probe overlaps the 3' portion of the SV40 gene and the 5' portion of the neomycin phosphotransferase resistance (Neor) gene.

There was no vector related mortality or morbidity observed with either the Mx-dnG1 or MxV-dnG1 vector. Low level positive signals were detected in the liver, lung and spleen of both low dose and high dose vector-treated animals. No PCR signal was detected in the testes, brain or heart of vector-treated animals. Histopathologic examination revealed portal vein phlebitis, pyelonephritis with focal myocarditis in two animals with indwelling catheters and no antibiotic prophylaxis. No other pathology was noted in non-target organs of Mx-dnG1- or MxV-dnG1-treated mice. Serum chemistry profiles revealed mild elevations in ALT and AST in the Mx-dnG1-treated animals compared to PBS controls. However, the levels were within normal limits for mice. No vector neutralizing antibodies were detected in the sera of vector-treated animals in a 7-week follow-up period.

The preclinical findings noted above confirm that intravenous infusion of Mx-dnG1 in two nude mouse models of human pancreatic cancer showed no appreciable damage to neighboring normal tissues nor systemic side effects. The method of targeted gene delivery via intravenous infusion offers several clinically relevant advantages. Infusion into the venous system will allow treatment of the tumor as well as occult foci of tumor. It is believed that the higher mitotic rate observed in dividing tumor cells will result in a higher transduction efficiency in tumors, while sparing hepatocytes and other normal tissues. Therefore, we propose a human clinical research protocol using intravenously administered Mx-dnG1 vector for the treatment of locally advanced or metastatic pancreatic cancer and other solid tumors refractory to standard chemotherapy.

Example 5

Clinical Reports

The objectives of the study were (1) to determine the dose-limiting toxicity and maximum tolerated dose (safety) of successive intravenous infusions of Rexin-G, and (2) to assess potential anti-tumor responses. The protocol was designed for end-stage cancer patients with an estimated survival time of at least 3 months. Three patients with Stage IV pancreatic cancer who were considered refractory to standard chemotherapy by their medical oncologists were invited to participate in the compassionate use protocol using Rexin-G as approved by the Philippine Bureau of Food and Drugs. An intrapatient dose escalation regimen by intravenous infusion of Rexin-G was given daily for 8-10 days. Completion of this regimen was followed by a one-week evaluation period for dose limiting toxicity; after which, the maximum tolerated dose of Rexin-G was administered for another 8-10 days. If the patient did not develop a grade 3 or 4 adverse event related to Rexin-G during the observation period, the dose of Rexin-G was escalated as shown in Table 1 (supra).

Tumor response was evaluated by serial determinations of the tumor volume using the formula: width$^2$×length×0.52 as measured by calipers, or by radiologic imaging (MRI or CT scan).

Patient #1, a 47 year-old Filipino female was diagnosed, by histologic examination of biopsied tumor tissue and staging studies, to have localized adenocarcinoma of the pancreatic head. She underwent a Whipples surgical procedure which included complete resection of the primary tumor. This was followed by single agent gemcitabine weekly for 7 doses, but chemotherapy was discontinued due to unacceptable toxicity. Several months later, a follow-up MRI showed recurrence of the primary tumor with metastatic spread to both the supra-clavicular and abdominal lymph nodes. In compliance with the clinical protocol, the patient received two 10-day treatment cycles of Rexin-G for a cumulative dose of 2.1×10e11 Units over 28 days, with an interim rest period of one week. In the absence of systemic toxicity, the patient received an additional 10-day treatment cycle for a total cumulative dose of 3×10e11 Units.

The sizes of two superficial supraclavicular lymph nodes were measured manually using calipers. A progressive decrease in the tumor volumes of the supraclavicular lymph nodes was observed, reaching 33% and 62% reductions in tumor size, respectively, by the end of treatment cycle #2 on Day 28 (Table 2).

TABLE 2

Patient # 1 Caliper Measurements of Supraclavicular Lymph Nodes

| Date | Caliper Measurement cm | Tumor Volume* cm³ | % Reduction in Size from Start of Rexin-G Rx |
|---|---|---|---|
| Day 1 | LN1 1.9 × 2.1 | 3.9 | |
| | LN2 1.5 × 1.8 | 2.1 | |
| Day 26 | LN1 1.8 × 1.8 | 3.0 | 23 |
| | LN2 1.3 × 1.3 | 1.1 | 48 |
| Day 27 | LN1 1.7 × 1.7 | 2.6 | 33 |
| | LN2 1.15 × 1.15 | 0.8 | 62 |

Follow-up abdominal MRI revealed (i) no new areas of tumor metastasis, (ii) discemable areas of central necrosis, involving 40-50% of the primary tumor, and (iii) a significant decrease in the size of the para-aortic abdominal lymph node (FIG. 1A-B). On Day 54, a follow-up MRI showed no interval change in the size of the primary tumor. Consistent with these findings, a progressive decrease in CA19-9 serum levels (from a peak of 1200 to a low of 584 U/ml) were noted, amounting to a 50% reduction in CA19-9 levels on Day 54 (FIG. 1C). However, a follow-up CT scan on Day 101 showed a significant increase in the size of the primary tumor and the supraclavicular lymph nodes. The patient refused further chemotherapy until Day 175 when the patient agreed to receive weekly gemcitabine, 1000 mg/m2. By RECIST criteria, Patient #1 is alive with progressive disease on Day 189 follow-up, 6.75 months from the start of Rexin-G infusions, 11 months from the time of tumor recurrence, and 20 months from the time of initial diagnosis.

Figure 2C:
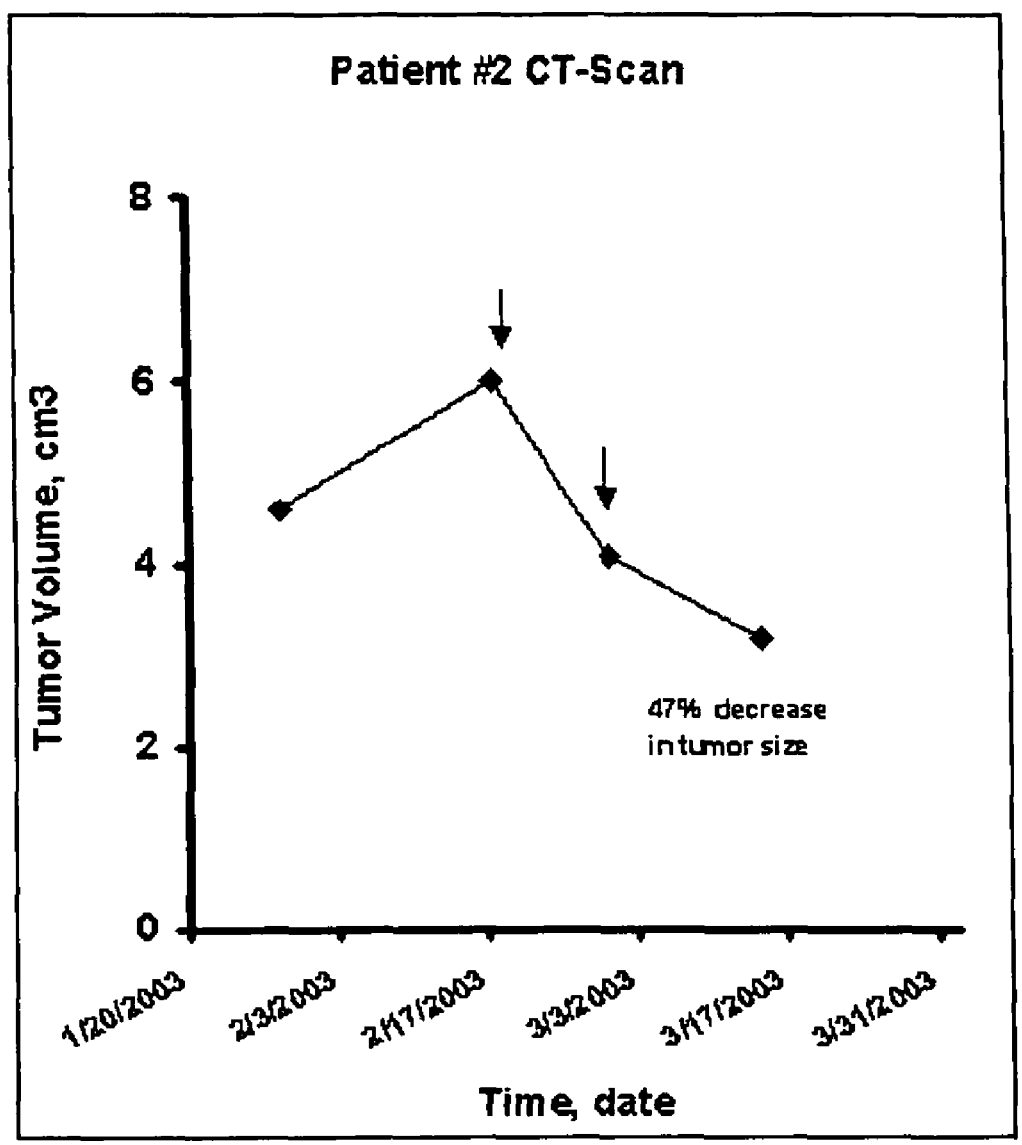
FIG. 2C is a graph showing that Rexin-G arrests primary tumor growth in Patient #2. A progressive decrease in tumor size was noted with successive treatment with Rexin-G. Tumor volume (cm$^3$) derived by using the formula: width$^2$ ×length×0.52 (O'Reilly et al. Cell 88, 277, 1997), and plotted on the vertical axis, is expressed as a function of time, plotted on the horizontal axis. The start of each treatment cycle is indicated by arrows.

Patient # 2, a 56 year-old Filipino female was diagnosed to have Stage IVA locally advanced and non-resectable carcinoma of the pancreatic head, by cytologic examination of biliary brushings. Exploratory laparotomy revealed that the tumor was wrapped around the portal vein and encroached in close proximity to the superior mesenteric artery and vein. She had received external beam radiation therapy with 5-fluorouracil, and further received single agent gemcitabine weekly for 8 doses, followed by monthly maintenance doses. However, a progressive rise in CA19-9 serum levels was noted and a follow-up CT scan revealed that the tumor had increased in size (FIG. 2A). The patient received two treatment cycles of Rexin-G as daily intravenous infusions for a total cumulative dose of $1.8 \times 10^{11}$ Units. Results: Serial abdominal CT scans showed a significant decrease in tumor volume from 6.0 cm³ at the beginning of Rexin-G infusions to 3.2 cm³, at the end of the treatment, amounting to a 47% decrease in tumor size on Day 28 (FIG. 2A-C). Follow-up CT scan on Day 103 showed no interval change in the size of the tumor, after which the patient was maintained on monthly gemcitabine. By RECIST criteria, Patient #2 is alive, asymptomatic with stable disease on Day 154 follow-up, 5.5 months from the start of Rexin-G infusions, and 14 months after initial diagnosis.

Figure 3A:
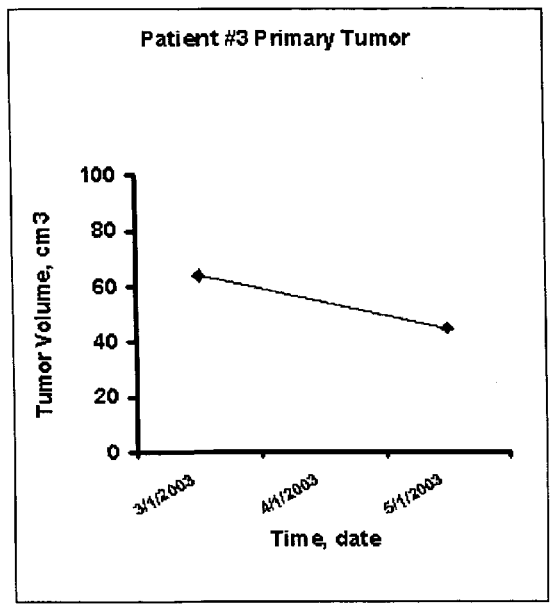
FIG. 3A depicts data indicating Rexin-G plus gemcitabine induces tumor regression in Patient #3 with metastatic pancreatic cancer. Tumor volumes (cm$^3$) of primary tumor is plotted on the Y axis and are expressed as a function of time, date. The start of Rexin-G infusions is indicated by arrows.
Figure 3B:
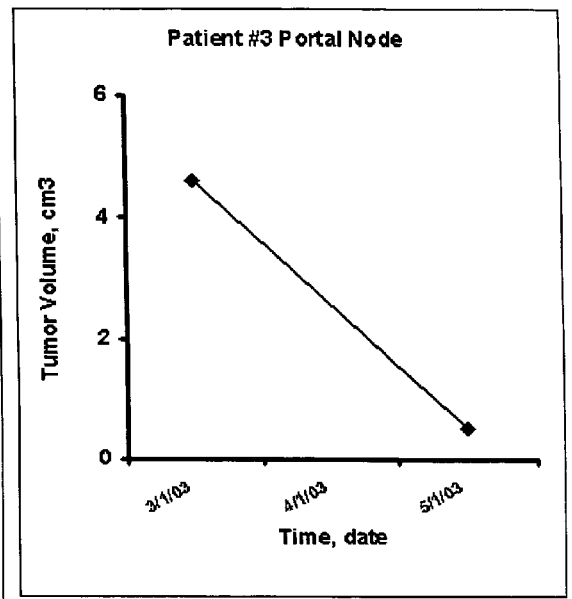
FIG. 3B depicts data indicating Rexin-G plus gemcitabine induces tumor regression in Patient #3 with metastatic pancreatic cancer. Tumor volume of portal node is plotted on the Y axis and are expressed as a function of time, date. The start of Rexin-G infusions is indicated by arrows.
Figure 3C:
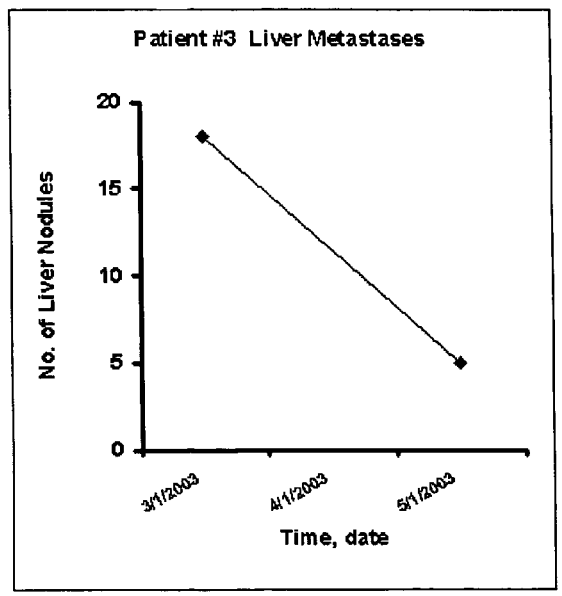
FIG. 3C depicts data indicating Rexin-G plus gemcitabine induces tumor regression in Patient #3 with metastatic pancreatic cancer. The number of liver nodules is plotted on the Y axis, are expressed as a function of time, date. The start of Rexin-G infusions is indicated by arrows.
Figure 4A:
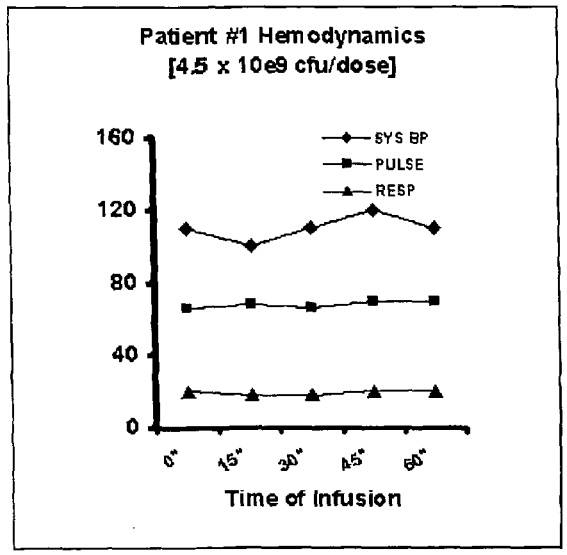
FIG. 4A the systolic blood pressure, expressed as mm Hg, plotted on the vertical axis, while time of REXIN-G infusion is plotted on the horizontal axis, for patient #1.
Figure 4B:
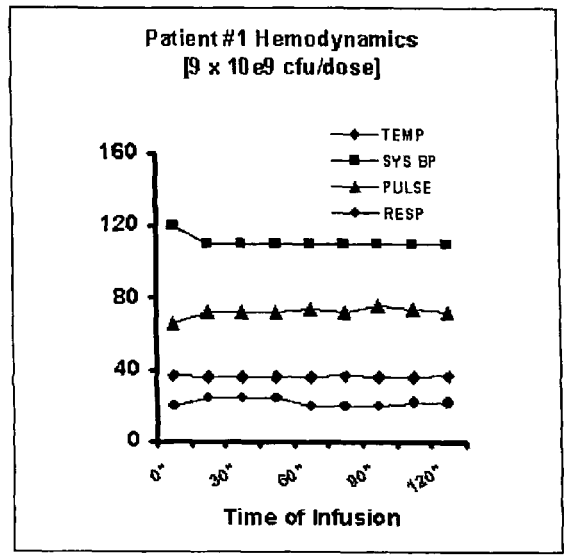
FIG. 4B pulse rate per minute plotted on the vertical axis, while time of REXIN-G infusion is plotted on the horizontal axis, for patient #1.
Figure 4C:
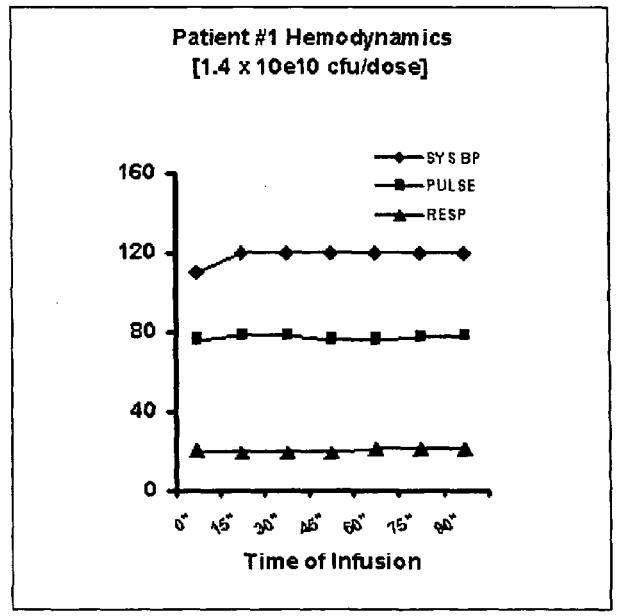
FIG. 4C respiratory rate per minute are plotted on the vertical axis, while time of REXIN-G infusion is plotted on the horizontal axis, for patient #1.
Figure 5A:
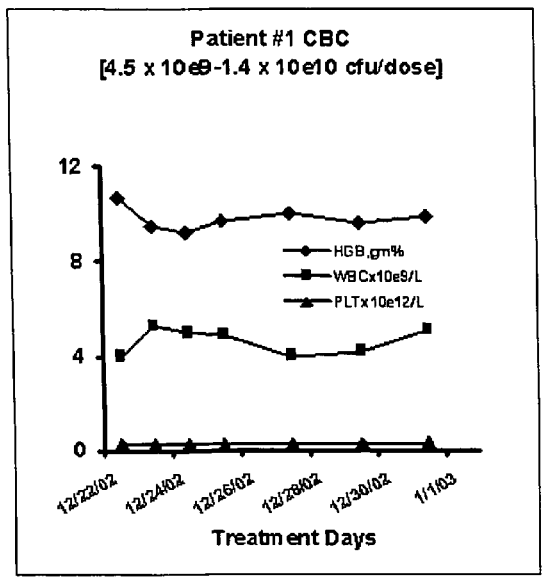
FIG. 5A depicts data indicating the hemoglobin (gms %), white blood count and platelet count for patient #1 plotted on the Y axis and expressed as a function of treatment days, plotted on the X axis.
Figure 5B:
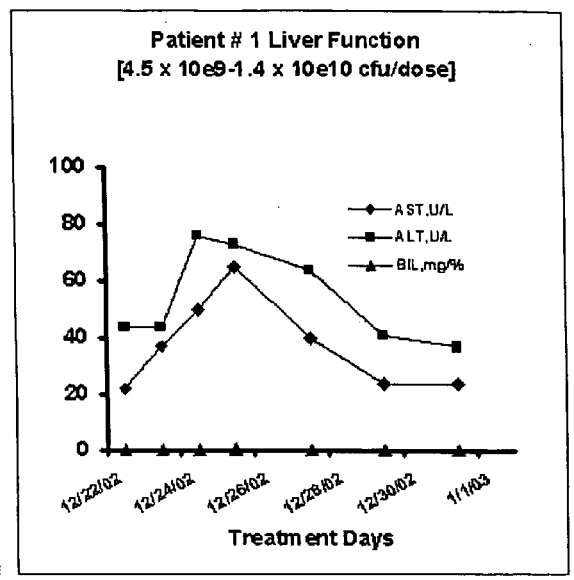
FIG. 5B depicts data indicating that Rexin-G has no adverse effects on for patient #1 liver function. AST (U/L) ALT (U/L), and bilirubin (mg %), plotted on the Y axis, are expressed as a function of treatment days, plotted on the X axis.
Figure 5C:
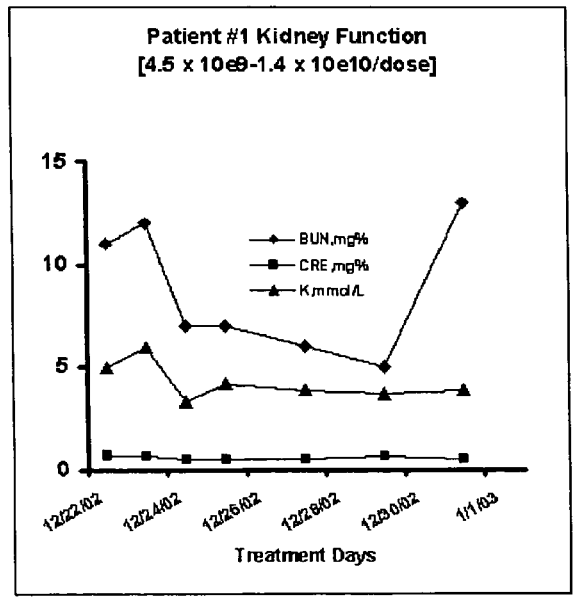
FIG. 5C depicts patient #1 Blood urea nitrogen (mg %), creatinine (mg %) and potassium (mmol/L) levels, plotted on the Y axis, expressed as a function of treatment days, plotted on the X axis. Dose Level 1 ($4.5 \times 10^9$ cfu/dose) was given for 6 consecutive days, rest period for two days, followed by Dose Level 11 ($9 \times 10^9$ cfu/dose) for 2 days, and then Dose Level III ($1.4 \times 10^{10}$ cfu/dose) for 2 days.
Figure 6A:
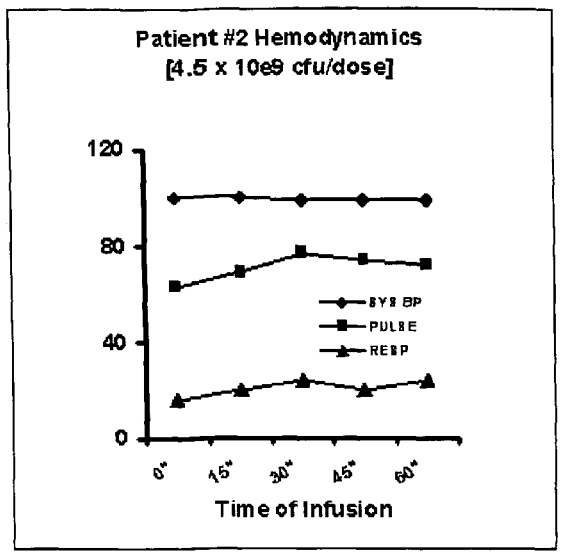
FIG. 6 provides data indicating that dose escalation of Rexin-G has no adverse effects on Patient #2's hemodynamic functions. For each dose level, the systolic blood pressure (mm Hg), pulse rate/min, and respiratory rate/per minute are plotted on the vertical axis as a function of time of infusion, plotted on the horizontal axis.
Figure 6B:
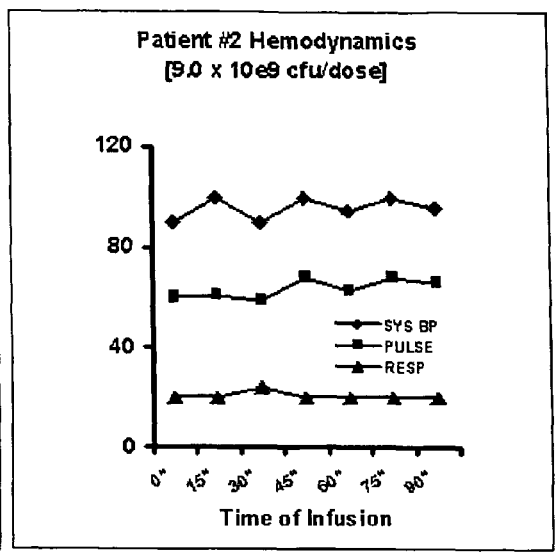
Figure 6C:
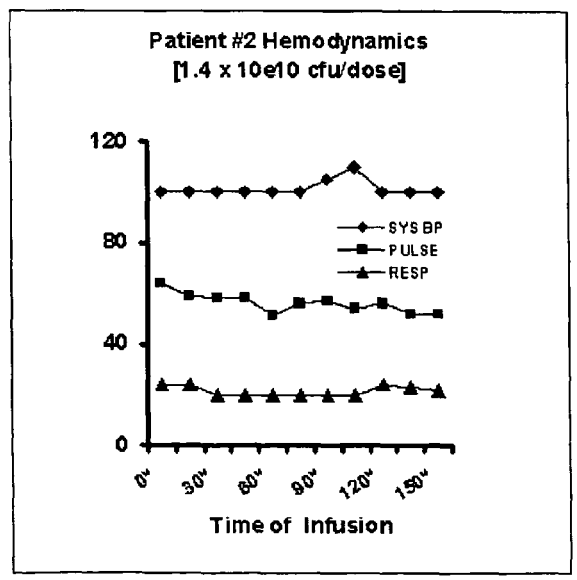
Figure 7A:
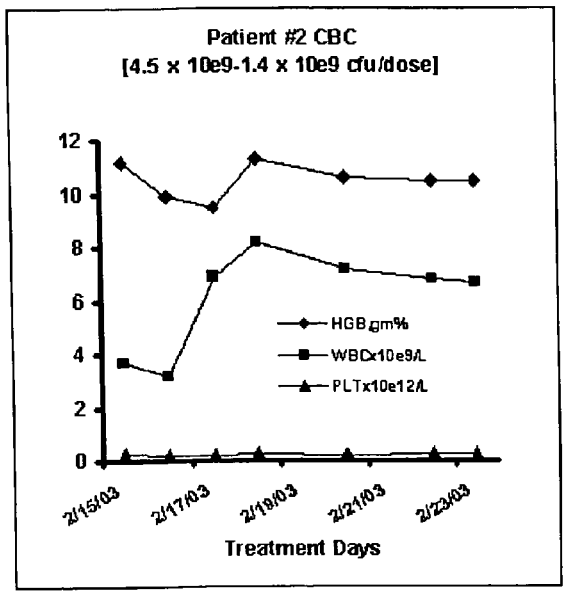
FIG. 7A depicts hemoglobin (gms %), white blood count and platelet count for patient #2 plotted on the Y axis and expressed as a function of treatment days, plotted on the X axis.
Figure 7B:
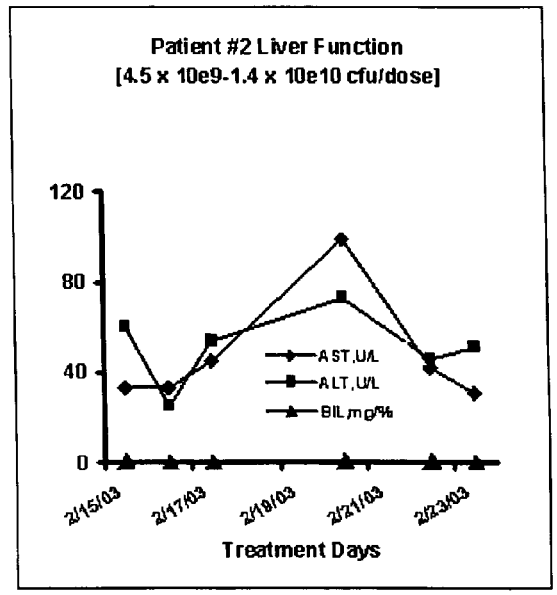
FIG. 7B depicts data indicating that Rexin-G has no adverse effects on for patient #2 liver function. AST (U/L) ALT (U/L), and bilirubin (mg %), plotted on the Y axis, are expressed as a function of treatment days, plotted on the X axis.
Figure 7C:
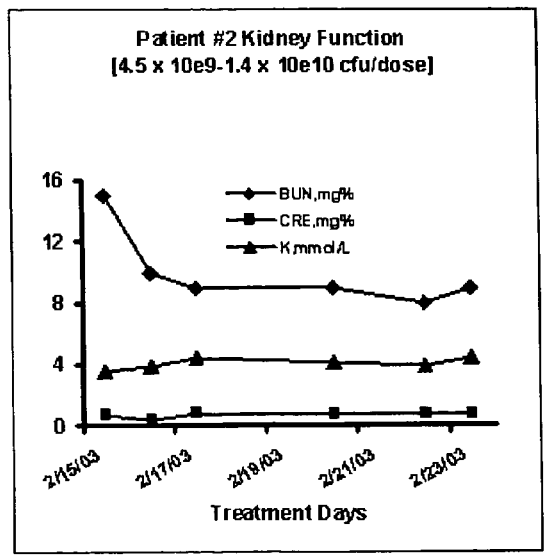
FIG. 7C depicts blood urea nitrogen (mg %), creatinine (mg %) and potassium (mmol/L) levels for patient #2, plotted on the Y axis expressed as a function of treatment days, plotted on the X axis. Dose Level 1 ($4.5 \times 10^9$ cfu/dose) was given for 5 consecutive days, followed by Dose Level II ($9 \times 10^9$ cfu/dose) for 3 days, and then Dose Level III ($1.4 \times 10^9$ cfu/dose) for 2 days.
Figure 8A:
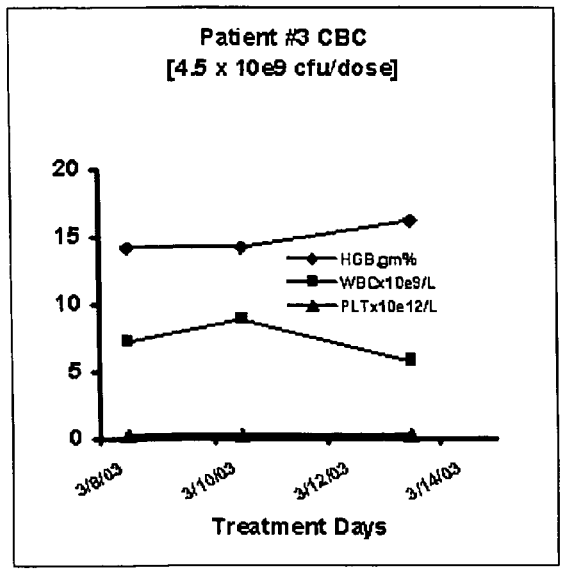
FIG. 8A depicts hemoglobin (gms %), white blood count and platelet count for patient #3 plotted on the Y axis and expressed as a function of treatment days, plotted on the X axis.
Figure 8B:
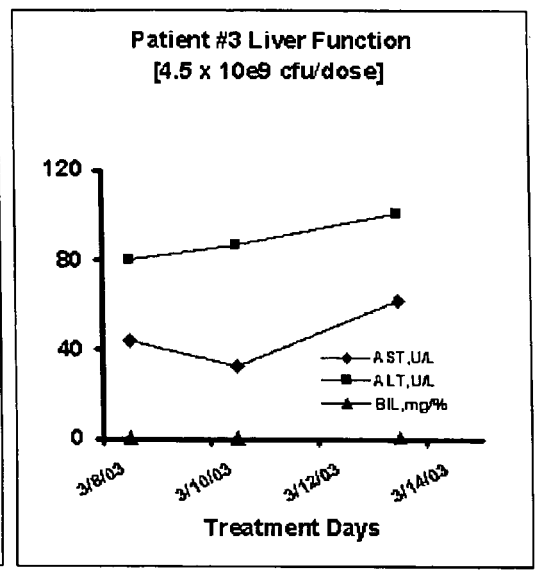
FIG. 8B depicts data indicating that Rexin-G has no adverse effects on for patient #3 liver function. AST (U/L) ALT (U/L), and bilirubin (mg %), plotted on the Y axis, are expressed as a function of treatment days, plotted on the X axis.
Figure 8C:
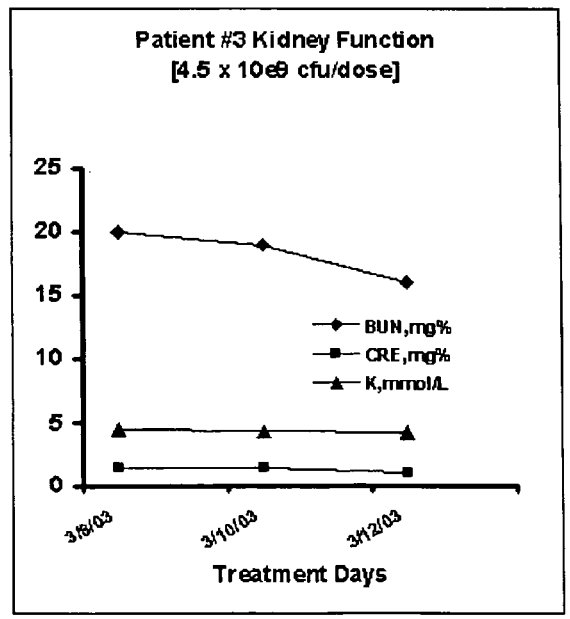
FIG. 8C depicts data indicating that Rexin-G has no adverse effects on for patient #3 kidney function. Blood urea nitrogen (mg %), creatinine (mg %) and potassium (mmol/L) levels, plotted on the Y axis, are expressed as a function of treatment days, plotted on the X axis. Dose Level 1 ($4.5 \times 10^9$ cfu/dose) was given for 6 consecutive days.
Figure 9:
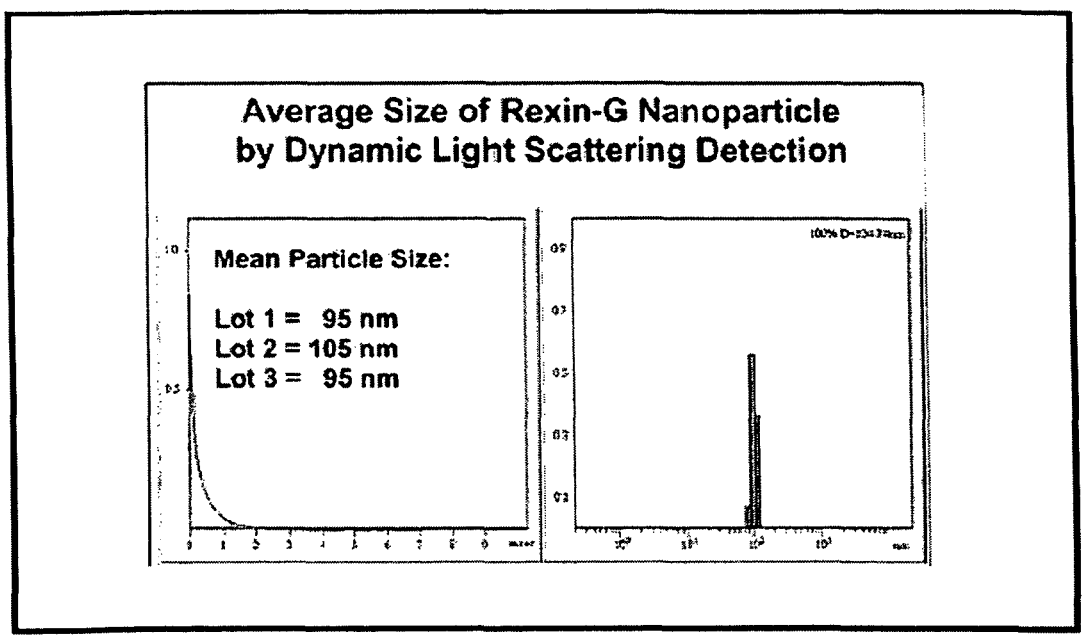
FIG. 9 depicts size measurements of Rexin-G nanoparticles. Using a Precision Detector Instrument (Franklin, Mass. 02038 U.S.A.), the vector samples were analyzed using Dynamic Light Scattering (DLS) in Batch Mode for determining molecular size as the hydrodynamic radius (rh). Precision Deconvolve software was used to mathematically determine the various size populations from the DLS data. The average particle size of 3 Rexin-G clinical lots are 95, 105 and 95 nm respectively with no detectable viral aggregation.
Figure 10:
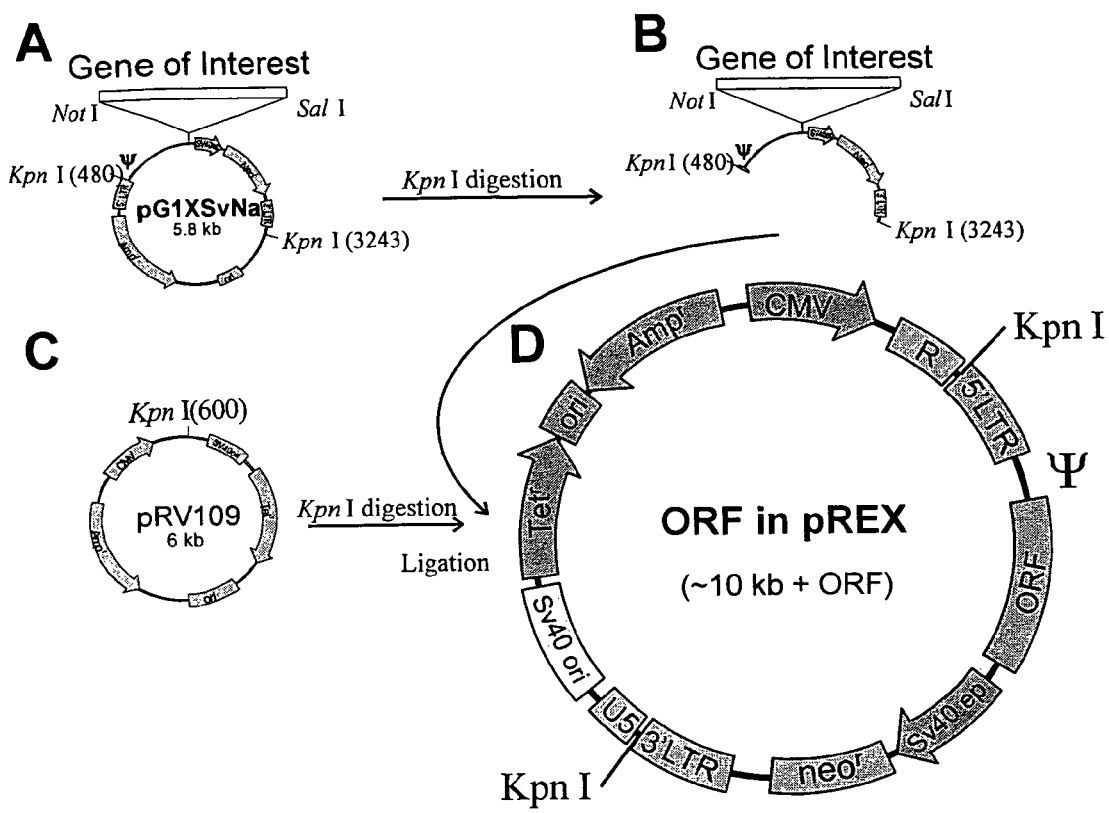
FIG. 10 depicts the High Infectious Titer (HIT) version of the GTI expression vector G1nXSvNa. The pRV109 plasmid provides the strong CMV promoter. The resulting pREX expression vector has an SV40 ori for episomal replication and plasmid rescue in producer cell lines expressing the SV40 large T antigen (293T), an ampicillin resistance gene for selection and maintenance in *E. coli*, and a neomycin resistance gene driven by the SV40 e.p. to determine vector titer. The gene of interest is initially cloned as a PCR product with Not I and Sal I overhangs. The amplified fragments are verified by DNA sequence analysis and inserted into the retroviral expression vector pREX by cloning the respective fragment into pG1XsvNa (Gene Therapy Inc.), then excising the Kpn I fragment of this plasmid followed by ligation with a linearized (Kpn I-digested) pRV109 plasmid to yield the respective HIT/pREX vector.

Patient # 3, a 47 year old Chinese diabetic male was diagnosed to have Stage IVB adenocarcinoma of the body and tail of the pancreas, with numerous metastases to the liver and portal lymph node, confirmed by CT guided liver biopsy. Based on the rapid fatal outcome of Stage IVB adenocarcinoma of the pancreas, the patient was invited to participate in a second clinical protocol using Rexin-G frontline followed by gemcitabine weekly. A priming dose of Rexin-G was administered to sensitize the tumor to chemotherapy with gemcitabine for better cytocidal efficacy. The patient received daily IV infusions of Rexin-G at a dose of $4.5 \times 10^9$ Units/dose for 6 days for a total cumulative dose of $2.7 \times 10^{10}$ Units, followed by 8 weekly doses of gemcitabine (1000 mg/m²). On Day 62, follow-up abdominal CT scan showed that the primary tumor had decreased in size from 7.0×4.2 cm (Tumor Volume: 64.2 cm³) baseline measurement to 6.0×3.8 cm (Tumor Volume: 45 cm3) (FIG. 3A). Further, there was a dramatic reduction in the number of liver nodules from 18 nodules (baseline) to 5 nodules (FIG. 3C) with regression of the largest liver nodule from baseline 2.2×2 cm (Tumor Volume: 4.6 cm³) to 1×1 cm (Tumor Volume: 0.52 cm³) on Day 62 (FIG. 3B). By the RECIST criteria, Patient #3 is alive with stable disease on Day 133 follow-up, 4.7 months from the start of Rexin-G infusions and ~5 months from the time of diagnosis.

Table 3 illustrates the comparative evaluation of over-all tumor responses in the three patients. Using the RECIST criteria, Rexin-G induced tumor growth stabilization in all three patients.

TABLE 3

Evaluation of Over-all Tumor Responses by RECIST

| | Patient No. | | |
|---|---|---|---|
| | 1 | 2 | 3 |
| Stage of Disease | Recurrent IVB | IVA | IVB |
| Previous Rx | Whipples Procedure Ext. Beam Radiation Gemcitabine | Ext. Beam Radiation 5 Fluorouracil Gemcitabine | None |
| Karnofsky score before Treatment | 0 | 0 | 0 |
| Treatment/s & Dose | Rexin-G IV (3.0 × 10e11 U) | Rexin-G IV (1.8 × 10e11 U) | Rexin-G IV (2.7 × 10e10 U) Gemcitabine IV [1000 mg/m² × 8] |
| Response | Tumor growth stabilization | Tumor growth stabilization | Tumor growth stabilization |
| Duration of Response | 3.4 months | >5.5 months | >4.7 months |
| Survival Status | Alive, with progressive disease, 20 months from diagnosis | Alive, with stable disease, 14 months from diagnosis | Alive, with stable disease, 5 months from diagnosis |

In this study, two methods were used to evaluate tumor responses to intravenous infusions of Rexin-G. Using the NCI-RECIST criteria that measures the sum of the longest diameters of target lesions that are greater than 2 cm, and the disappearance vs persistence of all non-target lesions as points of comparison, 3 of 3 (100%) patients treated with Rexin-G had tumor growth stabilization for longer than 100 days (3 months) (Table 3). Evaluation of response by tumor volume measurement (formula: width$^2$×length×0.52) (16), revealed that Rexin-G induced tumor regression in 3 of 3 (100%) patients, i.e., a 33-62% regression of metastatic lymphadenopathy in Patient #1 (Table 2), a 47% regression of the primary tumor in Patient #2 (FIG. 2C), and a 30% regression of the primary tumor, eradication of 72% (13/18) of metastatic liver foci, and an 89% regression of a metastatic portal node in Patient #3 as documented by imaging studies (MRI or CT scan) and caliper measurements (FIG. 3). Further, evaluation of safety showed that no dose-limiting toxicity occurred up to a cumulative vector dose of $3\times10^{11}$ Units, indicating that more vector may be given to achieve greater therapeutic efficacy. The Rexin-G vector infusions were not associated with nausea or vomiting, diarrhea, neuropathy, hair loss, hemodynamic instability, bone marrow suppression, liver or kidney damage.

The practice of the present invention will employ, unless otherwise indicated, conventional techniques of cell biology, cell culture, molecular biology, transgenic biology, microbiology, recombinant DNA, and immunology, which are within the skill of the art. Such techniques are described in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor. N.Y., 1986).

What is claimed is:

1. A method of inhibiting tumor metastasis in a human patient having a tumor that has metastasized, said method comprising:
    intravenously administering to the patient a therapeutically effective amount of retroviral particles at a cumulative dose of at least $1.8 \times 10^{11}$ colony forming units (cfu), wherein each of the retroviral particles comprises:
    i) a modified retroviral envelope protein wherein the retroviral envelope protein includes a receptor binding region which has been modified to contain a collagen binding domain comprising a peptide comprising the amino acid sequence Gly-His-Val-Gly-Trp-Arg-Glu-Pro-Ser-Phe-Met-Ala-Leu-Ser-Ala-Ala (SEQ ID NO:1), and
    ii) encodes a heterologous therapeutic polypeptide.

2. The method of claim 1, wherein the retroviral particles accumulate in the patient in areas of exposed collagen.

3. The method of claim 2, wherein the areas of exposed collagen include neoplastic lesions, areas of active angiogenesis, metastatic tumor invasion lesions, cancerous lesions, areas of vascular injury, surgical sites, inflammatory sites or areas of tissue destruction.

4. The method of claim 1, wherein the therapeutic polypeptide is an N-terminal deletion mutant of cyclin G1 consisting of amino acid 41 to 249 of human cyclin G1.

5. The method of claim 1, wherein the therapeutic polypeptide is interleukin-2 (IL-2).

6. The method of claim 1, wherein the therapeutic polypeptide is granulocyte macrophage-colony stimulating factor (GM-CSF).

7. The method of claim 1, wherein the therapeutic polypeptide is thymidine kinase.

8. The method of claim 1, wherein the retroviral envelope protein is a modified 4070A amphotropic envelope protein.

9. The method of claim 1, wherein the receptor binding region is modified by inserting the peptide comprising the amino acid sequence Gly-His-Val-Gly-Trp-Arg-Glu-Pro-Ser-Phe-Met-Ala-Leu-Ser-Ala-Ala (SEQ ID NO:1) between two consecutively numbered amino acid residues of the native gp70 portion of the 4070A amphotropic envelope protein.

10. The method of claim 9, wherein the peptide is inserted between amino acids 6 and 7 of the native gp70 portion of the 4070A amphotropic envelope protein.

11. The method of claim 8, wherein the peptide is contained in the gp70 portion of the modified 4070A amphotropic envelope protein.

* * * * *